United States Patent [19]

Beach et al.

[11] Patent Number: 5,441,880
[45] Date of Patent: Aug. 15, 1995

[54] HUMAN CDC25 GENES, ENCODED PRODUCTS AND USES THEREOF

[75] Inventors: David H. Beach, Huntington Bay; Konstantin Galaktionov, Cold Spring Harbor, both of N.Y.

[73] Assignee: Cold Spring Harbor Laboratory, Cold Spring Harbor, N.Y.

[21] Appl. No.: 124,569

[22] Filed: Sep. 20, 1993

Related U.S. Application Data

[63] Continuation of Ser. No. 793,601, Nov. 18, 1991, abandoned.

[51] Int. Cl.$^6$ .................. C12N 9/10; C12N 15/00; C12Q 1/68; C07H 19/00
[52] U.S. Cl. .................. 435/193; 435/69.1; 435/69.3; 435/172.3; 435/194; 435/320.1; 530/350; 530/387.1; 536/22.1; 536/23.1; 536/23.2; 536/23.5
[58] Field of Search .................. 435/69.1, 69.3, 172.3, 435/193, 194, 320.1; 530/350, 387.1; 536/22.1, 23.1, 23.2, 23.5

[56] References Cited

PUBLICATIONS

Gautier, J. et al., *Cell*, 67:197–211 (Oct. 4, 1991).
Dunphy, W. G. and A. Kumagai, *Cell*, 67:189–196 (Oct. 4, 1991).
Sadhu et al. "Human homolog of fission yeast . . . "PNAS 87, pp. 5139–5143 Jul. 1990.
Lerner "Tapping the immunological . . . "Nature 299, pp. 592–596 14 Oct. 1982.
Nagata et al. "An additional homolog . . . "The New Biolgist 3, pp. 959–968 Oct. 1991.
Galaktionov et al. "Specific activation of cdc25 . . . "Cell 67, pp. 1181–1194 Dec. 20, 1991.

*Primary Examiner*—Keith C. Furman
*Assistant Examiner*—Hyosuk Kim
*Attorney, Agent, or Firm*—Matthew P. Vincent; Giulio A. DeConti, Jr.; Lahive & Cockfield

[57] ABSTRACT

Two previously undescribed human cdc25 genes, designated cdc25 A and cdc25 B, which have been shown to have an endogenous tyrosine phosphatase activity that can be specifically activated by B-type cyclin, in the complete absence of cdc2.

As a result of the work described herein, new approaches to regulating the cell cycle in eukaryotic cells and, particularly, to regulating the activity of tyrosine specific phosphatases which play a key role in the cell cycle are available. Applicant's invention relates to methods of regulating the cell cycle and, specifically, to regulating activation of cdc2-kinase, through alteration of the activity and/or levels of tyrosine phosphatases, particularly cdc25 phosphatase, and B-type cyclin or through alteration of the interaction of components of MPF, particularly the association of cdc25 with cyclin, cdc2 or the cdc2/cyclin B complex. The present invention also relates to agents or compositions useful in the method of regulating (inhibiting or enhancing) the cell cycle. Such agents or compositions are, for example, inhibitors (such as low molecular weight peptides or compounds, either organic or inorganic) of the catalytic activity of tyrosine specific PTPases (particularly cdc25), blocking agents which interfere with interaction or binding of the tyrosine specific PTPase with cyclin or the cyclin/cdc2 complex, or agents which interfere directly with the catalytic activity of the PTPases.

22 Claims, 21 Drawing Sheets

Figure 1A

Panel A

```
CGA AAG GCC GGC CTT GGC TGC GAC AGC CTG GGT AAG AGG TGT AGG TCG GCT TGG TTT
TCT GCT ACC CGG AGC TGG GCA AGC GGG TTG GGA GAA CAG CGA AGA CAG CGT GAG CCT
GGG CCG TTG CCT CGA GGC TCT CGC CCG GCT TCT CTT GCC GAC CCG CCA CGT TTG TTT
GGA TTT AAT CTT ACA GCT GGT TGC CGG CGC CCG CCC GCC CGC TGG CCT CGC GGT GTG
AGA GGG AAG CAC CCG TGC CTG TGG CTG GTG GCT GGC GCC TGG AGG GTC CGC ACA CCC
GCC CGG CCG CGC CGC TTT GCC CGC GGC AGC CGC GTC CCT GAA CCG CGG AGT CGT GTT
TGT GTT TGA CCC GCG GGC GCC GGT GGC GCG CGG CCG AGG CCG GTG TCG GCG GGG CGG
GGC GGT CGC GGC GGA GGC AGA GGA AGA GGG AGC GGG AGC TCT GCG AGG CCG GGC GCC
GCC ATG GAA CTG GGC CCG AGC CCC GCA CCG CGC CGC CTG CTC TTC GCC TGC AGC CCC
     M   E   L   G   P   S   P   A   P   R   R   L   L   F   A   C   S   P
CCT CCC GCG TCG CAG CCC GTC GTG AAG GCG CTA TTT GGC GCT TCA GCC GCC GGG GGA
 P   P   A   S   Q   P   V   V   K   A   L   F   G   A   S   A   A   G   G
CTG TCG CCT GTC ACC AAC CTG ACC GTC ACT ATG GAC CAG CTG CAG GGT CTG GGC AGT
 L   S   P   V   T   N   L   T   V   T   M   D   Q   L   Q   G   L   G   S
GAT TAT GAG CAA CCA CTG GAG GTG AAG AAC AAC AGT AAT CTG CAG AGA ATG GGC TCC
 D   Y   E   Q   P   L   E   V   K   N   N   S   N   L   Q   R   M   G   S
TCC GAG TCA ACA GAT TCA GGT TTC TGT CTA GAT TCT CCT GGG CCA TTG GAC AGT AAA
 S   E   S   T   D   S   G   F   C   L   D   S   P   G   P   L   D   S   K
GAA AAC CTT GAA AAT CCT ATG AGA AGA ATA CAT TCC CTA CCT CAA AAG CTG TTG GGA
 E   N   L   E   N   P   M   R   R   I   H   S   L   P   Q   K   L   L   G
TGT AGT CCA GCT CTG AAG AGG AGC CAT TCT GAT TCT CTT GAC CAT GAC ATC TTT CAG
 C   S   P   A   L   K   R   S   H   S   D   S   L   D   H   D   I   F   Q
CTC ATC GAC CCA GAT GAG AAC AAG GAA AAT GAA GCC TTT GAG TTT AAG AAG CCA GTA
 L   I   D   P   D   E   N   K   E   N   E   A   F   E   F   K   K   P   V
AGA CCT GTA TCT CGT GGC TGC CTG CAC TCT CAT GGA CTC CAG GAG GGT AAA GAT CTC
 R   P   V   S   R   G   C   L   H   S   H   G   L   Q   E   G   K   D   L
TTC ACA CAG AGG CAG AAC TCT GCC CAG CTC GGA ATG CTT TCC TCA AAT GAA AGA GAT
 F   T   Q   R   Q   N   S   A   Q   L   G   M   L   S   S   N   E   R   D
AGC AGT GAA CCA GGG AAT TTC ATT CCT CTT TTT ACA CCC CAG TCA CCT GTG ACA GCC
 S   S   E   P   G   N   F   I   P   L   F   T   P   Q   S   P   V   T   A
ACT TTG TCT GAT GAG GAT GAT GGC TTC GTG GAC CTT CTC GAT GGA GAG AAT CTG AAG
 T   L   S   D   E   D   D   G   F   V   D   L   L   D   G   E   N   L   K
AAT GAG GAG GAG ACC CCC TCG TGC ATG GCA AGC CTC TGG ACA GCT CCT CTC GTC ATG
 N   E   E   E   T   P   S   C   M   A   S   L   W   T   A   P   L   V   M
AGA ACT ACA AAC CTT GAC AAC CGA TGC AAG CTG TTT GAC TCC CCT TCC CTG TGT AGC
 R   T   T   N   L   D   N   R   C   K   L   F   D   S   P   S   L   C   S
TCC AGC ACT CGG TCA GTG TTG AAG AGA CCA GAA CGT TCT CAA GAG GAG TCT CCA CCT
 S   S   T   R   S   V   L   K   R   P   E   R   S   Q   E   E   S   P   P
GGA AGT ACA AAG AGG AGG AAG AGC ATG TCT GGG GCC AGC CCC AAA GAG TCA ACT AAT
 G   S   T   K   R   R   K   S   M   S   G   A   S   P   K   E   S   T   N
CCA GAG AAG GCC CAT GAG ACT CTT CAT CAG TCT TTA TCC CTG GCA TCT TCC CCC AAA
 P   E   K   A   H   E   T   L   H   Q   S   L   S   L   A   S   S   P   K
GGA ACC ATT GAG AAC ATT TTG GAC AAT GAC CCA AGG GAC CTT ATA GGA GAC TTC TCC
 G   T   I   E   N   I   L   D   N   D   P   R   D   L   I   G   D   F   S
AAG GGT TAT CTC TTT CAT ACA GTT GCT GGG AAA CAT CAG GAT TTA AAA TAC ATC TCT
 K   G   Y   L   F   H   T   V   A   G   K   H   Q   D   L   K   Y   I   S
```

*Figure 1B*

Panel A (con't)

```
CCA GAA ATT ATG GCA TCT GTT TTG AAT GGC AAG TTT GCC AAC CTC ATT AAA GAG TTT
 P   E   I   M   A   S   V   L   N   G   K   F   A   N   L   I   K   E   F
GTT ATC ATC GAC TGT CGA TAC CCA TAT GAA TAC GAG GGA GGC CAC ATC AAG GGT GCA
 V   I   I   D   C   R   Y   P   Y   E   Y   E   G   G   H   I   K   G   A
GTG AAC TTG CAC ATG GAA GAA GAG GTT GAA GAC TTC TTA TTG AAG AAG CCC ATT GTA
 V   N   L   H   M   E   E   E   V   E   D   F   L   L   K   K   P   I   V
CCT ACT GAT GGC AAG CGT GTC ATT GTT GTG TTT CAC TGC GAG TTT TCT TCT GAG AGA
 P   T   D   G   K   R   V   I   V   V   F   H   C   E   F   S   S   E   R
GGT CCC CGC ATG TGC CGG TAT GTG AGA GAG AGA GAT CGC CTG GGT AAT GAA TAC CCC
 G   P   R   M   C   R   Y   V   R   E   R   D   R   L   G   N   E   Y   P
AAA CTC CAC TAC CCT GAG CTG TAT GTC CTG AAG GGG GGA TAC AAG GAG TTC TTT ATG
 K   L   H   Y   P   E   L   Y   V   L   K   G   G   Y   K   E   F   F   M
AAA TGC CAG TCT TAC TGT GAG CCC CCT AGC TAC CGG CCC ATG CAC CAC GAG GAC TTT
 K   C   Q   S   Y   C   E   P   P   S   Y   R   P   M   H   H   E   D   F
AAA GAA GAC CTG AAG AAG TTC CGC ACC AAG AGC CGG ACC TGG GCA GGG GAG AAG AGC
 K   E   D   L   K   K   F   R   T   K   S   R   T   W   A   G   E   K   S
AAG AGG GAG ATG TAC AGT CGT CTG AAG AAG CTC TGA GGG CGG CAG GAC CAG CCA GCA
 K   R   E   M   Y   S   R   L   K   K   L   *
GCA GCC CAA GCT TCC CTC CAT CCC CCT TTA CCC TCT TTC CTG CAG AGA AAC TTA AGC
AAA GGG GAC AGC TGT GTG ACA TTT GGA GAG GGG GCC TGG GAC TTC ATG CCT TAA ACC
CTA CCT CCC ACA CTC CCA AGG TTG GAG CCC AGG GCA TCT TGC TGG CTA CGC CTC TTC
TGT CCC TGT TAG ACG TCC TCC GTC CAT ATC AGA ACT GTG CCA CAA TGC AGT TCT GAG
CAC CGT GTC AAG CTG CTC TGA GCC ACA GTG GGA TGA ACC AGC CGG GGC CTT ATC GGG
CTC CAG CAT CTC ATG AGG GGA GAG GAG ACG GAG GGG AGT AGA GAA GTT TAC ACA GAA
ATG CTG CTG GCC AAA TAG CAA AGA G
```

*Figure 1C*

Panel B

```
CTG CCC TGC GCC CGG CCC TCC AGC CAG CCT GCC AGC TGT GCC GGC GTT TGT TGG
TCT GCC GGC CCC GCC GCG ATG GAG GTG CCC CAG CCG GAG CCC GCG CCA GGC TCG
                        M   E   V   P   Q   P   E   P   A   P   G   S
GCT CTC AGT CCA GCA GGC GTG TGC GGT GGC GCC CAG CGT CCG GGC CAC CTC CCG
 A   L   S   P   A   G   V   C   G   G   A   Q   R   P   G   H   L   P
GGC CTC CTG CTG GGA TCT CAT GGC CTC CTG GGG TCC CCG GTG CGG GCG GCC GCT
 G   L   L   L   G   S   H   G   L   L   G   S   P   V   R   A   A   A
TCC TCG CCG GTC ACC ACC CTC ACC CAG ACC ATG CAC GAC CTC GCC GGG CTC GGC
 S   S   P   V   T   T   L   T   Q   T   M   H   D   L   A   G   L   G
AGC CGC AGC CGC CTG ACG CAC CTA TCC CTG TCT CGA CGG GCA TCC GAA TCC TCC
 S   R   S   R   L   T   H   L   S   L   S   R   R   A   S   E   S   S
CTG TCG TCT GAA TCC TCC GAA TCT TCT GAT GCA GGT CTC TGC ATG GAT TCC CCC
 L   S   S   E   S   S   E   S   S   D   A   G   L   C   M   D   S   P
AGC CCT ATG GAC CCC CAC ATG GCG GAG CAG ACG TTT GAA CAG GCC ATC CAG GCA
 S   P   M   D   P   H   M   A   E   Q   T   F   E   Q   A   I   Q   A
GCC AGC CGG ATC ATT CGA AAC GAG CAG TTT GCC ATC AGA CGC TTC CAG TCT ATG
 A   S   R   I   I   R   N   E   Q   F   A   I   R   R   F   Q   S   M
CCG GTG AGG CTG CTG GGC CAC AGC CCC GTG CTT CGG AAC ATC ACC AAC TCC CAG
 P   V   R   L   L   G   H   S   P   V   L   R   N   I   T   N   S   Q
GCG CCC GAC GGC CGG AGG AAG AGC GAG GCG GGC AGT GGA GCT GCC AGC AGC TCT
 A   P   D   G   R   R   K   S   E   A   G   S   G   A   A   S   S   S
GGG GAA GAC AAG GAG AAT GAT GGA TTT GTC TTC AAG ATG CCA TGG AAG CCC ACA
 G   E   D   K   E   N   D   G   F   V   F   K   M   P   W   K   P   T
CAT CCC AGC TCC ACC CAT GCT CTG GCA GAG TGG GCC AGC CGC AGG GAA GCC TTT
 H   P   S   S   T   H   A   L   A   E   W   A   S   R   R   E   A   F
GCC CAG AGA CCC AGC TCG GCC CCC GAC CTG ATG TGT CTC AGT CCT GAC CGG AAG
 A   Q   R   P   S   S   A   P   D   L   M   C   L   S   P   D   R   K
ATG GAA GTG GAG GAG CTC AGC CCC CTG GCC CTA GGT CGC TTC TCT CTG ACC CCT
 M   E   V   E   E   L   S   P   L   A   L   G   R   F   S   L   T   P
GCA GAG GGG GAT ACT GAG GAA GAT GAT GGA TTT GTG GAC ATC CTA GAG AGT GAC
 A   E   G   D   T   E   E   D   D   G   F   V   D   I   L   E   S   D
TTA AAG GAT GAT GAT GCA GTT CCC CCA GGC ATG GAG AGT CTC ATT AGT GCC CCA
 L   K   D   D   D   A   V   P   P   G   M   E   S   L   I   S   A   P
CTG GTC AAG ACC TTG GAA AAG GAA GAG GAA AAG GAC CTC GTC ATG TAC AGC AAG
 L   V   K   T   L   E   K   E   E   E   K   D   L   V   M   Y   S   K
TGC CAG CGG CTC TTC CGC TCT CCG TCC ATG CCC TGC AGC GTG ATC CGG CCC ATC
 C   Q   R   L   F   R   S   P   S   M   P   C   S   V   I   R   P   I
CTC AAG AGG CTG GAG CGG CCC CAG GAC AGG GAC ACG CCC GTG CAG AAT AAG CGG
 L   K   R   L   E   R   P   Q   D   R   D   T   P   V   Q   N   K   R
AGG CGG AGC GTG ACC CCT CCT GAG GAG CAG CAG GAG GCT GAG GAA CCT AAA GCC
 R   R   S   V   T   P   P   E   E   Q   Q   E   A   E   E   P   K   A
CGC GTC CTC CGC TCA AAA TCA CTG TGT CAC GAT GAG ATC GAG AAC CTC CTG GAC
 R   V   L   R   S   K   S   L   C   H   D   E   I   E   N   L   L   D
AGT GAC CAC CGA GAG CTG ATT GGA GAT TAC TCT AAG GCC TTC CTC CTA CAG ACA
 S   D   H   R   E   L   I   G   D   Y   S   K   A   F   L   L   Q   T
```

*Figure 1C*

Panel B (con't)

```
GTA GAC GGA AAG CAC CAA GAC CTC AAG TAC ATC TCA CCA GAA ACG ATG GTG GCC
 V   D   G   K   H   Q   D   L   K   Y   I   S   P   E   T   M   V   A
CTA TTG ACG GGC AAG TTC AGC AAC ATC GTG GAT AAG TTT GTG ATT GTA GAC TGC
 L   L   T   G   K   F   S   N   I   V   D   K   F   V   I   V   D   C
AGA TAC CCC TAT GAA TAT GAA GGC GGG CAC ATC AAG ACT GCG GTG AAC TTG CCC
 R   Y   P   Y   E   Y   E   G   G   H   I   K   T   A   V   N   L   P
CTG GAA CGC GAC GCC GAG AGC TTC CTA CTG AAG AGC CCC ATC GCG CCC TGT AGC
 L   E   R   D   A   E   S   F   L   L   K   S   P   I   A   P   C   S
CTG GAC AAG AGA GTC ATC CTC ATT TTC CAC TGT GAA TTC TCA TCT GAG CGT GGG
 L   D   K   R   V   I   L   I   F   H   C   E   F   S   S   E   R   G
CCC CGC ATG TGC CGT TTC ATC AGG GAA CGA GAC CGT GCT GTC AAC GAC TAC CCC
 P   R   M   C   R   F   I   R   E   R   D   R   A   V   N   D   Y   P
AGC CTC TAC TAC CCT GAG ATG TAT ATC CTG AAA GGC GGC TAC AAG GAG TTC TTC
 S   L   Y   Y   P   E   M   Y   I   L   K   G   G   Y   K   E   F   F
CCT CAG CAC CCG AAC TTC TGT GAA CCC CAG GAC TAC CGG CCC ATG AAC CAC GAG
 P   Q   H   P   N   F   C   E   P   Q   D   Y   R   P   M   N   H   E
GCC TTC AAG GAT GAG CTA AAG ACC TTC CGC CTC AAG ACT CGC AGC TGG GCT GGG
 A   F   K   D   E   L   K   T   F   R   L   K   T   R   S   W   A   G
GAG CGG AGC CGG CGG GAG CTC TGT AGC CGG CTG CAG GAC CAG TGA GGG GCC TGC
 E   R   S   R   R   E   L   C   S   R   L   Q   D   Q   *
GCC AGT CCT GCT ACC TCC CTT GCC TTT CGA GGC CTG AAG CCA GCT GCC CTA TGG
GCC TGC CGG GCT GAG GGC CTG CTG GAG GCC TCA GGT GCT GTC CAT GGG AAA GAT
GGT GTG GTG TCC TGC CTG TCT GCC CCA GCC CAG ATT CCC CTG TGT CAT CCC ATC
ATT TTC CAT ATC CTG GTG CCC CCC ACC CCT GGA AGA GCC CAG TCT GTT GAG TTA
GTT AAG TTG GGT TAA TAC CAG CTT AAA GGC AGT ATT TTG TGT CCT CCA GGA GCT
TCT TGT TTC CTT GTT AGG GTT AAC CCT TCA TCT TCC TGT GTC CTG AAA CGC TCC
TTT GTG TGT GTG TCA GCT GAG GCT GGG GAG AGC CGT GGT CCC TGA GGA TGG GTC
AGA GCT AAA CTC CTT CCT GGC CTG AGA GTC AGC TCT CTG CCC TGT GTA CTT CCC
GGG CCA GGG CTG CCC CTA ATC TCT GTA GGA ACC GTG GTA TGT CTG CCA TGT TGC
CCC TTT CTC TTT TCC CCT TTC CTG TCC CAC CAT ACG AGC ACC TCC AGC TGA ACA
AGA AGC TCT TAC TCT TTC CTA TTT CAG TGT TAC CTG TGT GCT TGG TCT GTT TGA
CTT TAC GCC CAT CTC AGG ACA CTT CCG TAG ACT GTT TAG GTT CCC CTG TCA AAT
ATC AGT TAC CCA CTC GGT CCC AGT TTT GTT GCC CCA GAA AGG GAT GTT ATT ATC
CTT GGG GGC TCC CAG GGC AAG GGT TAA GGC CTG AAT CAT GAG CCT GCT GGA AGC
CCA GCC CCT ACT GCT GTG AAC CCT GGG GCC TGA CTG CTC AGA ACT TGC TGC TGT
CTT GTT GCG GAT GGA TGG AAG GTT GGA TGG ATG GGT GGA TGG CCG TGG ATG GCC
GTG GAT GCG CAG TGC CTT GCA TAC CCA AAC CAG GTG GGA GCG TTT TGT TGA GCA
TGA CAC TGC AGC AGG AAT ATG TGT GCC TAT TTG TGT GGA CAA AAA TAT TTA
CAC TTA GGG TTT GGA GCT ATT CAA GAG GAA ATG TCA CAG AAG CAG CTA AAC CAA
GGA CTG AGC ACC CTC TGG ATT CTG AAT CTC AAG ATG GGG GCA GGG CTG TGC TTG
AAG GCC CTG CTG AGT CAT CTG TTA GGG CCT TGG TTC AAT AAA GCA CTG AGC AAG
TTG AGA AAA AAA AAA AAA AAA AAA
```

Figure 2

```
cdc25A   1-318
cdc25B   1-361
cdc25C   1-276
stg      1-269
25Sp     1-382
```

(sequence alignment)

```
cdc25A   523
cdc25B   566
cdc25C   474
stg      479
25Sp     580
```

αcdc25A
MW    −    +    1   2   3   4
(kD)
200 —
93 —
67 —
45 —
30 —
21 —
*Figure 3A*

*Figure 8A*

```
              CA
           V  HC                                                                                   R
           I
consensus                                                                                          
cdc25A     TDGKRVIIVFHCEFSSERGPRMCRYVRERDRLIGNE--YPKEHYPELYVLKGGYKEFFMKCQSYCEPPSYRPMHHE
cdc25B     SLDKRVILLFHCEFSSERGPRMCRFIRERDRAVND--YPSLYYPEMYILKGGYKEFFPQHPNFCEPQDYRPMNHE
cdc25C     DTQKRIIVFHCEFSSERGPRMCRCLREEDRSLNQ--YPALYYPELYILKGGYVRDFFPETMELCEPQSYCPMHHQ
stg        SGHKRNIIFHCEFSSERGPKMSRGLRNLDRERNTNAYPAIHYPEIYLLHNGYKEFFESHVELCEPHAYRTMLDP
25sp       --HVRA-LVFHCEHSAHRAPHLALHFRNTDRRMNSHRYPFLYYPEVYILHGGYKSFYENHKNRCDPINYVPMNDR VH-1       ----NEPVLVHCAAGVNRSGAMILA----YIMSKNKESLPMLYFLYVHSMRDLR-GAFVENPSFKR----QIIELAVIE
RPTP       LSPENGPIVHCSAGIGRSCTFCLADTCLLEMDKRKDPSSVD-IKKVLLEMRRFRMG-LIQTADQLRFSYLAVIE
HPTP       LSPEHGPIVHCSAGIGRSCTFCLADTCLLEMDKRKDPSSVD-IKKVLLEMRKFRMG-LIQTADQLRFSYLAVIE
TPTP       LNPDHGPAVIHCSAGIGRSGTFSLVDTCLVEMEKGDDIN----IKQVLENMRKYRMG-LIQTPDQLRFSYMAIIE HCYCB1     LAVNDVDAEDGADPNLCSEYVKDIYAYLRQLEEEQAVRPKYLLGREVTGNMRAILIDWLVQ----VQMKFRLIQ----E
XCYCB1     IHVKDVDADDDGNPMLCSEYVKDIYAYLRSLEDAQAVRQNYLHGQEVTGNMRAILIDWLVQ----VQMRFRLLQ----E
XCYCB2     TSVEDIDADDGGNPQLCSDYVMDIYNYLKQLEVQQSVHPCYLEGKEINERMRAILVDWLVQ----VHSRFQLLQ----E
HCYCD1     LCCEVETIRRAYPDANLLNDRVLRAMLKAEETCAPSVSYFKCVQKEVLPSMRKIVATWMLE----VCEEQKCEE----E
HCYCA      MSIVLEDEKPVSVNEVPDYHEDIHTYLREMEVKCKPKVGYMKKQPDLITNSMRAILVDWLVE----VGEEYKLQN----E consensus     V    SMR                 LVQ      RF          E
              I    N                   IE
                                     CR
                                cyclin box →
```

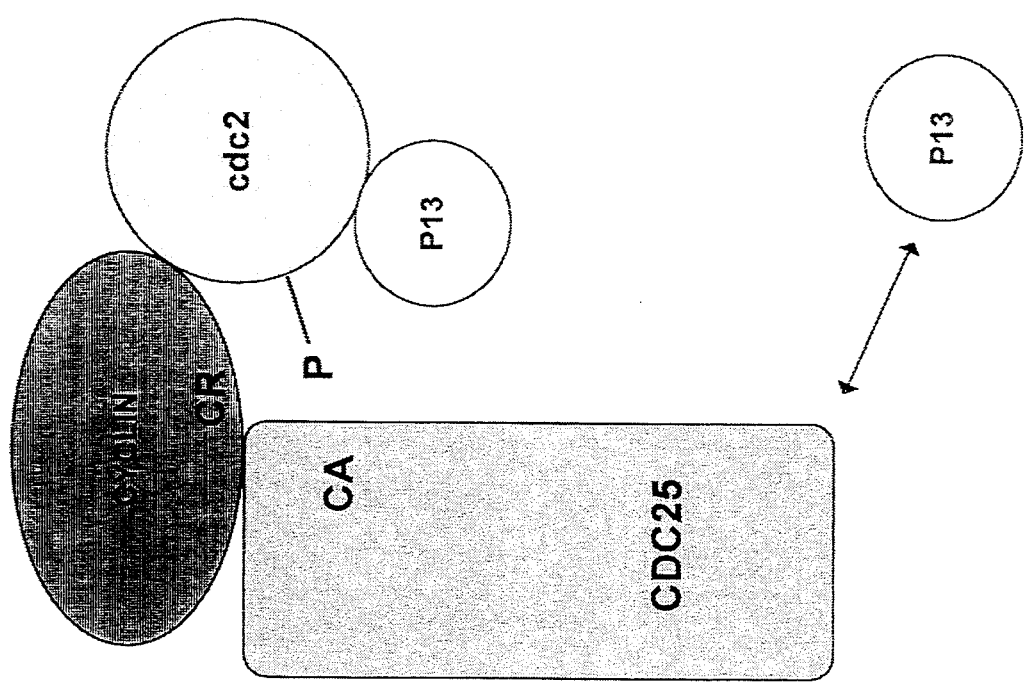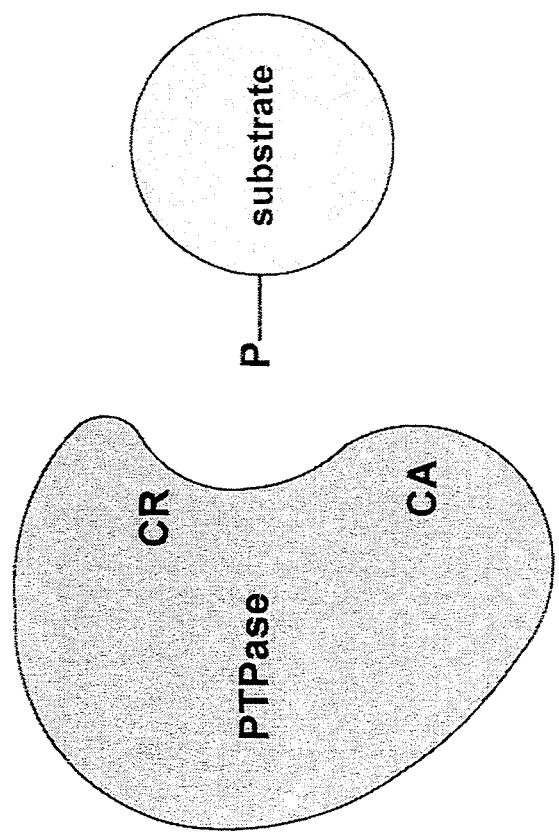
Figure 8B

43 —

34kD →
30 —

20 —
   1  2  3

94 —

72kD →
67

43 —

1  2  3

43 —

34kD →
30 —

20 —
   1  2  3

43 —

34kD →
30 —

1  2  3

HUMAN CDC25 GENES, ENCODED PRODUCTS AND USES THEREOF

DESCRIPTION

Funding

Work described herein was funded by the National Institutes of Health (GM 69620) and the Howard Hughes Medical Institute. The United States government has certain rights in the invention.

This application is a continuation of application Ser. No. 07/793,601, filed on Nov. 18, 1991, now abandoned.

BACKGROUND OF THE INVENTION

In eukaryotic cells, mitosis is initiated following the activation of a protein kinase known as MPF, the M-phase specific histone kinase or more simply as the M-phase kinase (for review see Murray and Kirshner, 1989). This kinase consists of at least three subunits; the catalytic subunit (cdc2), a regulatory subunit (cyclin B) and a low molecular weight subunit (p13-Sucl) (Brizuela, L. et al., *EMBO J.* 6:3507-3514 (1987); Dunphy, W. et al., *Cell* 54:423-431 (1988); Gautier, J. et al., *Cell* 54:433-439 (1988); Arion, D. et al., *Cell* 55:371-378 (1988); Draetta, G. et al., *Cell* 56:829-838 (1989)Booher, R. et al., *Cell* 58:485-497 (1989); Labbe, J. -C. et al., *EMBO J.* 83053-3058 (1989); Meijer, L. et al., *EMBO J.* 8:2275-2282 (1989); Gautier, J. et al., *Cell* 60:487-494 (1990); Gautier, J. and J. Maller, *EMBO J.* 10:177-182 (1991)). cdc2 and related kinases, also associate with other cyclins (Giordana, A. et al., *Cell* 58:981-990 (1989); Draetta, G. et al., *Cell* 56:829-838 (1989); Richardson, H. E. et al., *Cell* 59:1127-1133 (1989)) and comprise a family of related enzymes that act at various stages of the division cycle (Paris, J. et al., *Proc. Natl. Acad. Sci. USA* 88:1039-1043 (1990); Elledge, S. J. and M. R. Spottswood, *EMBO J.* 10:2653-2659 (1991); Tsai, L. -H. et al., *Nature* 353:174-177 (1991)).

The cdc2/cyclin B enzyme is subject to multiple levels of control. Among these, the regulation of the catalytic subunit by tyrosine phosphorylation is the best understood. In a variety of eukaryotic cell types, cdc2 is one of the most heavily tyrosine phosphorylated proteins (Draetta, G. et al., *Nature* 336:738-744 (1988); Dunphy, W. G. and J. W. Newport, *Cell* 58:181-431 (1989); Morla, A. O et al., *Cell* 58:193-203 (1989)). Phosphorylation of the tyrosine15 and also threonine14 residues of cdc2 is regulated, in part, by the accumulation of cyclin above a threshhold level at which association with cdc2 occurs (Solomon, M. J. et al., *Cell* 63:1013-1024 (1990)). Tyrosine phosphorylation inhibits the cdc2/cyclin B enzyme and tyrosine dephosphorylation, which occurs at the onset of mitosis, directly activates the pre-MPF complex (Gautier J. et al., *Nature* 339:626-629 (1989); Labbe, J. C. et al., *EMBO J.* 8:3053-3058 (1989); Morla, A. O. et al., *Cell* 58:193-203 (1989); Dunphy, W. G. and J. W. Newport, *Cell* 58:181-431 (1989); Morla, A. O. et al., *Cell* 58:193-203 (1989); Gould, K. and P. Nurse, *Nature* 342:39-45 (1989); Jessus, C. et al., *FEBS LETTERS* 266:4-8 (1990)):

Given the role of cdc2 dephosphorylation in activation of MPF, there is much interest in the regulation of the cdc2 phosphatase. Genetic studies in fission yeast have established that the cdc25 gene function is essential for the initiation of mitosis (Nurse, P. et al., *Mol. Gen. Genet.* 146:167-178 (1976). The cdc25 gene product serves as a rate-determining activator of the cdc2 protein kinase (Russell, P. and P. Nurse, *Cell* 45:145-153 (1986); Ducommun, B. et al., Biochem. Biophys. Res. Common. 167:301-309 (1990); Moreno, S. et al., *Nature* 344:549-552 (1990)). Moreover, the mutant cdc2-F15, whose product cannot be phosphorylated on tyrosine, bypasses the requirement for cdc25 protein function (Gould, K. and P. Nurse, *Nature* 342:39-45 (1989)). Additional work has suggested that cdc25 is the cdc2 phosphatase. (Kumagai, A. and W. G. Dunphy, *Cell* 64:903-914 (1991); Strausfeld, U. et al., *Nature* 351:242-245 (1991)) and that cdc25 is the cdc2 phosphatase which dephosphorylates tyrosine and possibly threonine residues on p34$^{cdc2}$ and regulates MPF activation. (Dunphy, W. G. and A. Kumagai, *Cell* 67:189-196 (1991); Gautier, J. et al., *Cell* 67:197-211 (1991)).

Because the signals that control dephosphorylation of ede2 on tyrosine and threonine play a key role in controlling timing of MPF activation and entry into mitosis, there is great interest in the proteins which control cdc2 dephosphorylation. Further knowledge of these proteins and their regulatory functions would be useful because it would provide a basis for a better understanding of cell division and, possibly, an approach to altering how it occurs.

SUMMARY OF THE INVENTION

For the first time, a key aspect of control of MPF activation and, thus, entry into mitosis, has been demonstrated. That is, B-type cyclins have been shown to activate cdc25 PTPase and a cdc25 protein has been shown to be able to directly stimulate the kinase activity of pre-MPF, resulting in activation of the M-phase kinase. As a result, it is now possible to design approaches to regulating entry into mitosis and, thus, regulate the cell cycle.

As described herein, Applicant has isolated two previously undescribed human cdc25 genes, designated cdc25 A and cdc25 B, and established that human cdc25 is a multigene family, consisting of at least three members. As further described herein, cdc25 A and cdc25 B have been shown to have an endogenous tyrosine phosphatase activity that can be specifically activated by B-type cyclin, in the complete absence of cdc2. It has also been shown for the first time that cdc25 phosphatases and B-type cyclins interact directly and that cyclin B is a multifunctional class of proteins which serve, in addition to their recognized role as regulatory subunits for M-phase cdc2, a previously unknown and surprising role as activators of the cdc25 phosphatase. In addition, Applicant has shown that, in Xenopus, cdc25 levels do not change, either during meiotic maturation or early embryonic division cycles, that cdc25 physically associates with a cdc2/cyclin B complex in a cell cycle dependent manner, that the maximal association between cdc25 and the cdc2/cyclin B complex occurs just before or at the time of maximal kinase activity (of cdc2) and that the cdc2 associated with cdc25 is tyrosine dephosphorylated and active as a kinase. In addition, as a result of the work described herein, it is now evident that in Xenopus, cyclin is the only protein that must be synthesized during each round of activation and inactivation of MPF. It had previously been proposed that cyclin must accumulate to a critical threshhold before pre-MPF is activated. However, it is reasonable, based on the work described herein, to suggest that this threshhold marks the point at which sufficient cyclin B has accumulated to allow activation of the continuously present cdc25 phosphatase (which, in turn, stimulates kinase activity of pre-MPF).

As also described herein, a surprising observation has been made as a result of comparison of the amino acid sequences of newly discovered cdc25 A and cdc25 B gene products with known tyrosine protein phosphatases (PTPases) and other proteins involved in the cell cycle. That is, it has been shown that the region of cdc25 immediately C-terminal to the putative catalytic domain is not highly related to that of other known PTPases. Particularly interesting is the fact that this region within PTPases includes sequence similarity to cyclins, particularly B-type cyclins, and that cdc25 proteins have no equivalent "cyclin region". The newly found cyclin region is almost immediately adjacent to the domain implicated in the catalytic function of the PTPases and cdc25 protein. As a result of these findings, particularly the observation that cdc25 protein lacks a motif, shared by cyclin and other PTPases, that may be an activating domain, it is reasonable to suggest that in the case of cdc25, the activating domain is provided "in trans" by intermolecular interaction with cyclin.

As a result of the work described herein, new approaches to regulating the cell cycle in eukaryotic cells and, particularly, to regulating the activity of tyrosine specific phosphatases which play a key role in relates to methods of regulating the cell cycle and, specifically, to regulating activation of cdc2-kinase, through alteration of the activity and/or levels of tyrosine phosphatases, particularly cdc25 phosphatase, and B-type cyclin or through alteration of the interaction of components of MPF, particularly the association of cdc25 with cyclin, cdc2 or the cdc2/cyclin B complex. The present invention also relates to agents or compositions useful in the method of regulating (inhibiting or enhancing) the cell cycle. Such agents or compositions are, for example, inhibitors (such as low molecular weight peptides or compounds, either organic or inorganic) of the catalytic activity of tyrosine specific PTPases (particularly cdc25), blocking agents which interfere with interaction or binding of the tyrosine specific PTPase with cyclin or the cyclin/cdc2 complex, or agents which interfere directly with the catalytic activity of the PTPases.

Applicant's invention also relates to cdc25 A, cdc25 B and additional members of the cdc25 multigene family and to methods and reagents (e.g., nucleic acid probes, antibodies) useful for identifying other members of the cdc25 family, particularly those of mammalian (e.g., human) origin.

BRIEF DESCRIPTION OF THE DRAWINGS

FIG. 1 is the nucleotide sequence of cdc25 A (SEQ ID #1) and the nucleotide sequence of cdc25 B (SEQ ID #3). Left panel, sequence of cdc25 A cDNA. Right panel, sequence of cdc25 B. Below the nucleotide sequence is the translation in standard single letter amino acid code (amino acid sequence encoded by cdc25 A cDNA, SEQ ID #2 and amino acid sequence encoded by cdc25 B cDNA, SEQ ID #4). In each sequence, the presumed initiating methionine is underlined. An in-frame stop codon upstream of the initiating AUG codon in the cdc25 A sequence is in bold and in each sequence, the terminating codon is marked by an asterisk.

FIG. 2 shows the homology of cdc25 proteins. The amino acid sequences of cdc25 A (SEQ ID #5) and cdc25 B (SEQ ID #6) were aligned with human cdc25 C (SEQ ID #7)(formerly CDC25Hs), string (Stg) (SEQ ID #8) and S.pombe cdc25 (25Sp) (SEQ ID #9) using the FASTA program. Identical amino acids are boxed. In cases of only two alternative amino acids at a particular site a box is also used. Dashes within the sequences indicate individual amino acid gaps created by the computer to generate optimal alignment.

FIG. 3 provides proof that human cdc25 A is essential for mitosis.

FIG. 3A, left panel. Immunoprecipitation of the S-labeled HeLa proteins with the anti-cdc25 A antiserum, in the absence (−) or presence (+) of antigenic peptide. The molecular weight of standards is given in kilodaltons (kD). Right panel, lane 1, histone H1 kinase activity of p13-bound p34$^{cdc2}$ kinase isolated as described in the text; lane 2, activity after addition of anti-cdc25 A eluate, following precipitation in the presence of excess antigenic peptide; lane 3, activity after addition of anti-cdc25 A eluate prepared in the absence of antigenic peptide; and lane 4, activity of the cdc25 A eluate.

FIG. 8 shows the alignment of the cdc25 proteins, PTPases and cyclins (Panel A) and a model of a proposed relationship between PTPases and the M-phase kinase and cdc25 phosphatase (Panel B). Panel A. Tyrosine phosphatases were aligned with each other as described in Guan, K. et al., *Nature* 350:359-362 (1991)) and cdc25 proteins as described in Gautier, J. et al., *Cell* 67:197-211 (1991)). The cyclin alignment was done by visual inspection. Only identity or similarity (V or I) within at least three members of one gene family and a minimal of two members of other family is boxed. CA indicates the puative catalytic domain of the cdc25 and cytoplasmic tyrosine phosphatases, and CR indicates the cyclin related domain, present in tyrosine phosphatases but absent in cdc25 proteins. Panel B. Schematic representation of a hypothetical relationship between PTPases, and the M-phase kinase and cdc25 phosphatase. The association between cdc2 and p13, and between cyclin and cdc2, is well documented. The interaction of cdc25 and cyclin is proposed here. p13 is proposed to have a low affinity interaction with cdc25. CA is the catalytic domain of PTPases and CR is a region of similarity between PTPases and cyclins. (cdc25 A, SEQ ID #10; cdc25 B, SEQ ID #11; cdc25 C, SEQ ID #12; Stg, SEQ ID #13 ; 25sp, SEQ ID #14; VH-1, SEQ ID #15; RPTP, SEQ ID #16; HPTP, SEQ ID #17, TPTP, SEQ ID #18; HCYCB1, SEQ ID #19; XCYCB1, SEQ ID #20; XCYCB2, SEQ ID #21; HCYCD1, SEQ ID #22; HCYCA, SEQ ID #23) FIG. 9 provides evidence of cdc25 protein in Xenopus Oocytes.

Figure 3B:
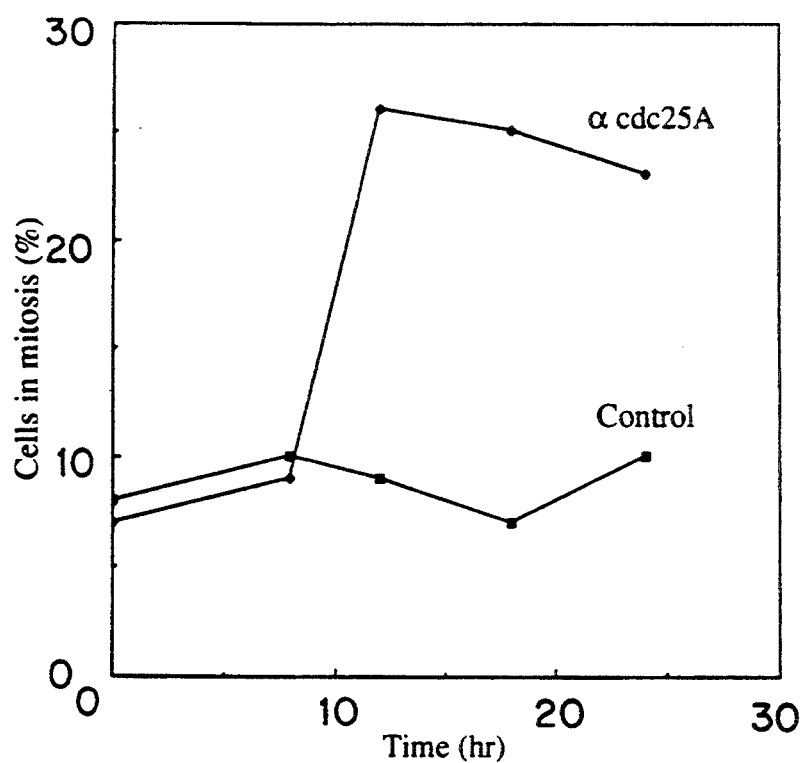
FIG. 3B. Mitotic index of a population of the HeLa cells microinjected with the affinity-purified anti-cdc25 A antibodies at time zero. Control cells were microinjected with the IgG fraction of the preimmune serum.

Panel A: Western blot with purified anti-cdc25 antibody (lanes 1 to 4) or with purified anti-cdc25 antibody blocked with an excess of yeast cdc25 (lanes 5 to 8). Lanes 1 and 5, prophase oocytes; lanes 2 and 6, metaphase unfertilized eggs; lanes 3 and 7, 40 min-activated eggs in the presence of cycloheximide; lanes 4 and 8, activated eggs 120 min after activation. Each lane contains the equivalent of 10 oocytes.

Panel B: Western blot with purified anti-cdc25 antibody. Lanes 1 to 4: anti-cdc25 immunoprecipitates of prophase oocytes (lane 1), of metaphase unfertilized eggs (lane 2), of 40 min-activated eggs in the presence of cycloheximide (lane 3) and without cellular extract (lane 4). Lanes 5 to 8: soluble proteins eluted from anti-cdc25 immunoprecipitates from prophase oocytes (lane 5), from metaphase unfertilized eggs (lane 6), from 40 min-activated eggs in the presence of cycloheximide (lane 7) and from activated eggs 120 min after activation (lane 8). Except lane 4, each lane contains the equivalent of 50 oocytes.

Panel C: p13-Sepharose precipitates corresponding to 100 prophase oocytes (lanes 1, 2 and 3) or 100 cycloheximide activated-eggs (lanes 4, 5 and 6) or 100 metaphase unfertilized eggs (lanes 7, 8 and 9) were incubated for 30 min at 30° C. in the absence (lanes 1, 4 and 7) or in the presence of the material eluted from anti-cdc25 immunoprecipitates of 200 prophase oocytes (lanes 2, 5 and 8) or of 200 metaphase unfertilized eggs (lanes 3, 6 and 9), further washed in kinase buffer and assayed for histone H2 kinase activity as described in experimental procedures. Shown below is quantitation of histone H1 kinase activity expressed as pmoles of phosphate incorporated per mg of histone H1 per min.

Figure 10:
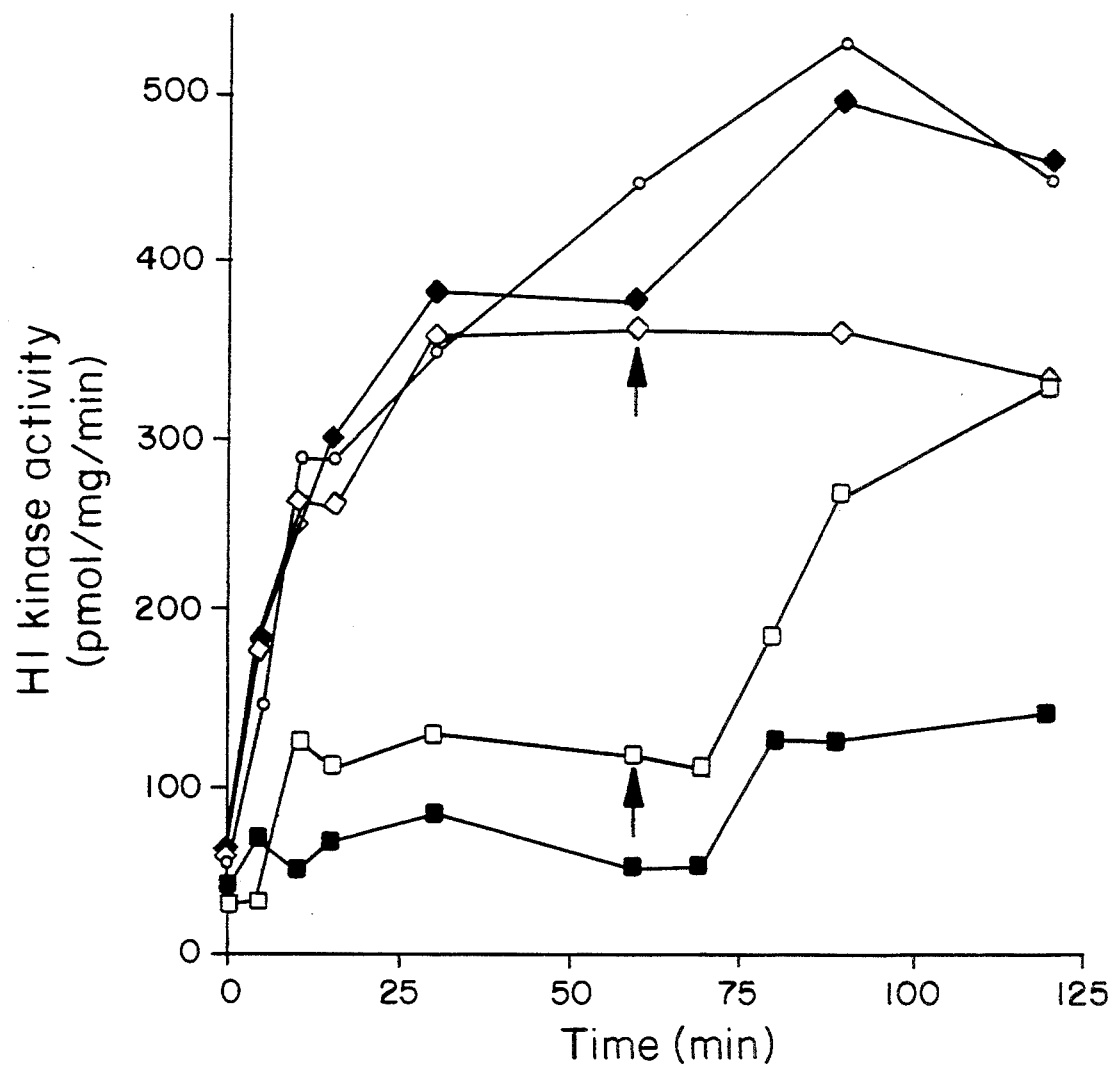

FIG. 10 is a graphic representation demonstrating that Xenopus cdc25 is required for activation of M-phase kinase. 200 ml of the 0–33% ammonium sulfate fraction of high speed extract of prophase oocytes was incubated for 15 min at 4° C. in the presence of 4 ml of either PBS-2% BSA (♦-♦) or preimmune anti-cdc25 serum (○-○;◇-◇) or purified anti-cdc25 antibody (■-■;□-□). At 0 min, samples were transferred at room temperature and 1 mM ATP, 10 mM creatine phosphate and 50 mg/ml creatine phosphokinase were added. In two cases (◇-◇;□-□), soluble bacterially expressed yeast cdc25 protein (100 mg/ml) was added at 60 min (indicated by arrows). Aliquots of the reactions were taken at the indicated times and assayed for histone Hi kinase activity as described in Experimental Procedures for Examples 7-13.

FIG. 11 provides evidence that cdc25 associates with cdc2 at M-phase. Extracts from prophase oocytes (lanes 1), metaphase unfertilized eggs (lanes 2) and cycloheximide-treated activated eggs (lanes 3) were prepared and analyzed as indicated below.

Panel A: Western blot with anti-cdc2 antibody of anti-cdc2 immunoprecipitates. Each lane contains the equivalent of 10 oocytes.

Panel B: Western blot with anti-cdc25 antibody of anti-cdc2 immunoprecipitates. Each lane contains the equivalent of 50 oocytes.

Panel C: Western blot with anti-cdc2 antibody of anti-cdc25 immunoprecipitates. Each lane contains the equivalent of 100 oocytes.

Panel D: Extracts were first depleted of cdc2/cyclin B complex by p13-Sepharose precipitation and then immunoprecipitated with purified anti-cdc25 antibody. Immunoprecipitates were subjected to Western blotting with anti-cdc2 antibody. Each lane contains the equivalent of 100 oocytes.

FIG. 12 provides evidence that cyclin B is associated with cdc2 and cdc25 at M-phase. Extracts from prophase oocytes (lanes 1), metaphase unfertilized eggs (lanes 2) and cycloheximide-treated activated eggs (lanes 3) were prepared and analyzed as indicated below.

Panel A: Western blot with anti-cyclin B2 antibody of p13-Sepharose precipitates. Each lane contains the equivalent of 10 oocytes.

Panel B: Western blot with anti-cdc25 antibody of anti-cyclin B2 immunoprecipitates. Each lane contains the equivalent of 50 oocytes.

Panel C: Western blot with anti-cyclin B2 antibody of anti-cdc25 immunoprecipitates. Each lane contains the equivalent of 50 oocytes.

Panel D: Extracts were first depleted of cdc2/cyclin B complex by p13-Sepharose precipitation and then immunoprecipitated with purified anti-cdc25 antibody. Immunoprecipitats were subjected to Western blotting with anti-cyclin B2 antibody. Each lane contains the equivalent of 50 oocytes.

Figure 13:
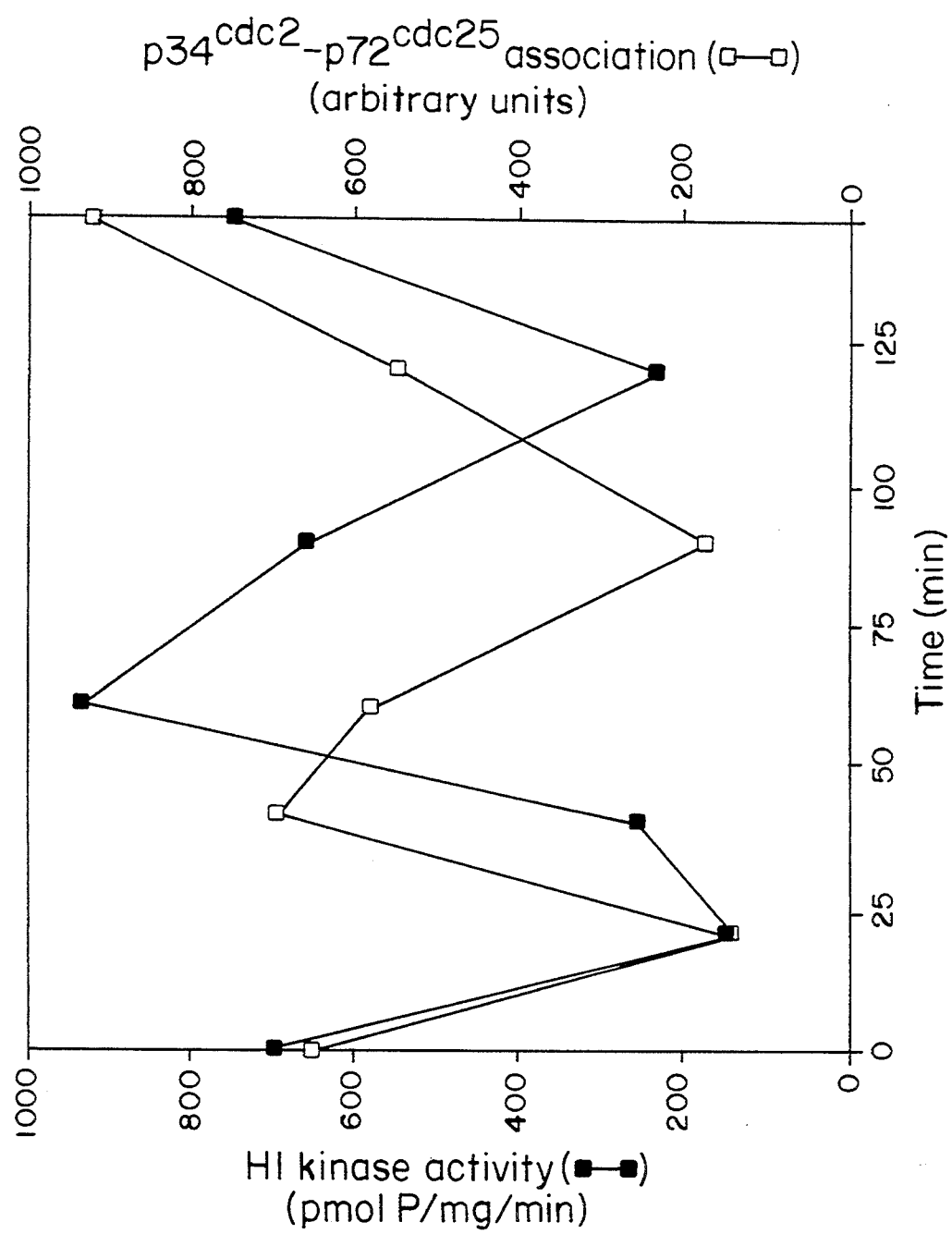

FIG. 13 is a graphic representation evidencing periodic physical association of cdc25 and cdc2/cyclin B. In vitro matured oocytes were activated at time 0 min by addition of $Ca^{2+}$-ionophore and $CaCl^2$ as described in Experimental procedures. At the indicated times, 100 eggs were homogenized, centrifuged and then either precipitated on p13-Sepharose beads or immunoprecipitated with anti-cdc25 antibody (■-■): histone H1 kinase activity of p13-Sepharose precipitates; (□-□): amounts of cdc2 found in anti-cdc25 immunocomplexes by blotting with anti-cdc2 antibody. Relative amounts of cdc2 present in the anti-cdc25 immunoprecipitates were quantified by Phosphor-Imager.

DETAILED DESCRIPTION OF THE INVENTION

The present invention relates to a method of regulating (inhibiting or enhancing) cell division and to agents or compositions useful for regulating the cell cycle. It further relates to two human genes encoding tyrosine-specific phosphatases, referred to as cdc25 A and cdc25 B, the encoded tyrosine-specific phosphatases and additional members of the cdc25 multigene family, particularly additional human cdc25 genes, and their encoded products. Applicant's invention is based on identification of new cdc25 genes and the discovery that cdc25 proteins interact directly with and are specifically activated by B-type cyclins and activate cdc2 kinase.

Applicant has isolated two human cdc25 genes, designated cdc25 A and cdc25 B, thus establishing that human cdc25 is a multigene family of at least three members. The three human cdc25 proteins (cdc25 A, cdc25 B and the previously identified cdc25 protein) have been shown to have approximately 40% identity in the most conserved C-terminal region. The cdc25 A and cdc25 B proteins can be classified as cdc25 proteins by a variety of independent criteria.

As shown herein, the cdc25 A gene product and cdc25 B gene product have endogenous tyrosine phosphatase activity in vitro which is stimulated severalfold, in the absence of cdc2, by cyclin B1 or cyclin B2. As is also shown herein, stable association occurs between cdc25 A and cyclin B1/cdc2 in human cells, specifically HeLa cells. These findings indicate that B-type cyclins are multi-functional proteins which not only are M-phase regulatory subunits, but also activate the cdc25 tyrosine phosphatase which, in turn, acts upon cdc2.

A region of amino acid similarity between cyclins and cytoplasmic tyrosine phosphatases has been identified and shown not to be present in cdc25 phosphatases, suggesting that the common motif represents an activating domain which must be provided to cdc25 by cdc25-cyclin B intramolecular interaction. Specifically, visual comparison of cdc25 A and cdc25 B with known tyrosine phosphatases (PTPases) and other proteins involved in cell cycle control resulted in the unexpected observation that a region of cdc25 immediately C-terminal to the putative cdc25 catalytic domain is not highly related to other known PTPases and that this newly found motif within the PTPases includes sequence similarity to cyclins, particularly of the B-type. Alignment of amino acid sequences of the cdc25 homologs and a diverse group of protein tyrosine phosphatases (PTPs) demonstrated that a C-terminal fragment of approximately 200 amino acid residues is a conserved protein motif which resembles the proposed catalytic center of viral and mammalian PTPases.

Applicant has shown that the two new human cdc25 genes encode proteins functionally related to that encoded by the fission yeast cdc25 (Example 2). One of the human cdc25 genes (cdc25 A) has been shown to act in mitosis in human cells (Example 3), which arrest in a "rounded up" mitotic state after microinjection of anti-cdc25 A antibodies. Thus, Applicant has shown for the first time that the PTPase is necessary for cell division; Applicant has also shown that cell division is inhibited by anti-cdc25 A antibodies, which are, thus, a cytotoxic agent.

Surprisingly, it has also been shown that the endogenous phosphatase activity of cdc25 A and cdc25 B proteins purified from *E. coli* is directly activated by stoichiometric addition of B-type cyclin, in the absence of cdc2 (Examples 4 and 5), thus showing that B-type cyclins have a multifunctional role in this stage of cell division. This clearly demonstrates specificity between cyclins in their role as activators of cdc25. Until this finding, it has proved difficult to demonstrate differences in substrate specificity among members of the cdc2/cyclin family, although a variety of lines of evidence have suggested that cyclins of different classes have specific roles at particular stages of cell division. The cdc25 A protein has been shown to be present in a complex with both cyclin B1 and cdc2 (Example 5).

Applicant has also determined that Xenopus oocytes contain a relative of cdc25, designated p72, which can directly stimulate the M-phase kinase in vitro and is essential for activation of the M-phase kinase in cell-free lysates. As described herein, the abundance of p72 does not change in Xenopus embryos during the cell cycle. p72 has been shown to directly associate with cdc2/cyclin B in a cell cycle dependent manner, reaching a peak at M-phase. The M-phase kinase which associates with p72 has been shown to be tyrosine dephosphorylated and catalytically active. As a result, it is reasonable to conclude that cdc25 triggers cdc2 activation by a mechanism which involves periodic physical association between cdc25 and the cyclin B/cdc2 complex and that it is the association between cdc2/cyclin B and cdc25 which is required. It is also reasonable to conclude that mitotic control can be effected by mechanisms other than transcriptional regulation of the cdc25 gene.

The following describes Applicant's isolation and characterization of two new human cdc25 genes; demonstration of the multifunctional role of B-type cyclin in mitosis; unexpected observation of a common amino acid sequence or motif present in PTPases and cyclins but absent in cdc25 and determination that the motif resembles the proposed catalytic center of viral and mammalian PTPs; demonstration of a specific interaction between cdc25 phosphatases and B-type cyclins; and demonstration that the level of cdc25 in Xenopus oocytes does not change during the cell cycle. As a result of the work described, novel methods and compositions for cell cycle regulation are available. These methods and compositions are also described below.

Isolation and Characterization of Two New Human cdc25 Genes Which Are Members of a Multigene Family Two new human cdc25 genes have been isolated, establishing the fact that in man, cdc25 is a multigene family that consists of at least three members. The three human cdc25 proteins share approximately 40% identity in the most conserved C-terminal region. The two newly discovered cdc25 genes, cdc25 A and cdc25 B, can be classified as cdc25 proteins by a variety of quite independent criteria. First, they share sequence similarity with other members of the family. Second, cdc25 A and cdc25 B can each rescue a mutant cdc25-22 strain of fission yeast. Third, injection of antibodies prepared against a peptide comprising part of the cdc25 A protein into proliferating HeLa cells causes their arrest in mitosis. Fourth, cdc25 A protein eluted from immunocomplexes can activate the latent histone kinase activity of cdc2. Fifth, both cdc25 A and cdc25 B purified from *E. coli* display an endogenous tyrosine phosphatase activity.

cdc25 Multigene Family

As described, it has now been shown that in humans, there are at least three cdc25 genes and possibly more.

In fission yeast, only one essential cdc25 gene has been identified to date (Russell, P. and P. Nurse, *Cell*

45:145–153 (1986)). Likewise, a single essential mitotic B-type cyclin has been described in this yeast (Booher, R. and D. Beach, *EMBO J.* 7:2321–2327 (1988)). Two mitotic B-type cyclins have been found both in frog and man (Minshull, J. et al., *Cell* 56:947–956 (1989)). Presumably, there is some differentiation of function between different members of the cdc25 and B-type cyclin families in vivo. Genetic studies in budding yeast, in which multiple B-type cyclins have been found, give some general hint that this is the case (Surana, U. et al., *Cell* 65:145–161 (1991); Ghiara, J. B. et al., *Cell* 65:163–174 (1991)). However, both cyclin B1 and B2 could activate cdc25 A in vitro. One might postulate that different human cdc25 genes activate different cyclin B/cdc2 complexes in vivo and this may explain why injection of anti-cdc25 A serum into HeLa cells causes arrest in mid-mitosis, rather than in interphase.

It should be noted that regulation of cdc2 by tyrosine phosphorylation has currently only been described with respect to the cdc2/cyclin B enzyme. However, in certain contexts, it has been possible to substitute cyclin B with cyclin A (Swenson, K. I., et al., *Cell* 47:861–870 (1986)); Pines, J. and T. Hunt, *EMBO J.* 6:2987–2995 (1987); Westendorf, et al., 1990), and indeed human cyclin B2 was isolated by virtue of its ability to rescue a cn-deficient strain of budding yeast (Xiong, Y. et al., *Cell* 65:691–699 (1991)). In the work described herein, cyclin A could not activate cdc25 A or cdc25 B (not shown). This does not preclude, however, the existence of undiscovered cdc25-related phosphatases, that might be specifically activated by cyclin A. It is also presently unknown whether relatives of cdc2, such as cdk2 (formerly egl, Paris, J. et al., *Proc. Natl. Acad. Sci. USA* 88:1039–1043 (1991); Elledge, S. J. and M. R. Scottswood, *EMBO J.* 10:2653–2659 (1991)), that can bind cyclin A (Tsai, L. -H. et al., *Nature* 353:174–177 (1991)), are subject to regulation by tyrosine phosphorylation and, hence, might require a cdc25 relative for activation.

Multifunctional Role of B-type Cyclin in Mitosis

A particularly striking observation described herein is the demonstration that the endogenous phosphatase activity of cdc25 A and cdc25 B proteins purified from *E. coli* can be directly activated by stoichiometric addition of B type cyclins. Specificity of this effect is shown by the inability of either cyclin A or cyclin D1 to display any such stimulation. A variety of lines of evidence (Booher, R. and D. Beach, *EMBO J.* 6:3441–3447 (1987); Booher, R. and D. Beach, *EMBO J.* 7:2321–2327 (1988); Nash, R. et al., *EBMO J.* 7:4335–4346 (1988); Hadwiger, J. A. et al., *Proc. Natl. Acad. Sci. USA* 86:6255–6259 (1989); Richardson, H. E. et al., *Cell* 59:1127–1133 (1989); Cross, F., *Mol. Cell. Biol.* 8:4675–4684 (1980); Wittenberg, C. et al., *Cell* 61:225–237 (1990); Minshull, et al. 1990; Draetta, G. et al., *Cell* 56:829–838 (1989); Giordano, A. et al., *Cell* 58:981–990 (1989); Pines, J. and T. Hunter, *Nature* 346:760–763 (1990); Xiong, Y. et al., *Cell* 65:691–699 (1991); Lew, D. J. et al., *Cell* 66:1–10 (1991); Koff, A. et al., *Cell* 88:1–20 (1991)) suggest that cyclins of different classes have specific roles at particular stages of the division cycle. However, it has proved difficult to demonstrate differences in substrate specificity between members of the cdc2/cyclin family in vitro and all known cyclins can rescue a CLN-deficient strain of budding yeast. The present experiments, vividly demonstrate specificity between different cyclins, in their role as activators of cdc25.

Certain evidence, both genetic and biochemical (Gould, K. and P. Nurse, *Nature* 342:39–45 (1989); Kumagai, A. and W. G. Dunphy, *Cell* 64:903–914 (1991); Strausfeld, U. et al., *Nature* 351:242–245 (1991); Gautier, J. et al., *Cell* 67:197–211 (1991)) suggests that cdc2 is a physiological substrate of cdc25 phosphatases. cdc2 was not used as a substrate in the present study because it binds to cyclins and, thus, potentially becomes altered as a phosphatase substrate. Therefore, the issue of cdc25 substrate specificity has not been addressed directly. However, the finding of activation of cdc25, specifically by B-type cyclins, strengthens the conclusion that cdc2/cyclin B is the relevant substrate in vivo. Demonstration of activation of cdc25 when artificial PTPase substrates were used leads to the conclusion that cyclins are able to interact with cdc25 in the total absence of cdc2 protein. In vivo, it is expected that this interaction occurs in the context of the cdc2/cyclin B pre-MPF complex. The above-described work demonstrates that B-type cyclins have at least two roles. First, they bind stoichiometrically with cdc2 to regulate the substrate specificity (Draetta, G. et al., *Nature* 336:738–744 (1989); Brizuela, L. et al., *Proc. Natl. Acad. Sci. USA* 86:4362–4366 (1989)) and the intracellular localization of the catalytic subunit (Booher, R. N. et al., *Cell* 58:485–497 (1989)). Second, they appear to have an independent function: the activation of cdc25 PTPase.

Genetic studies in fission yeast and Drosophila indicate that cdc25 is a dose-dependent activator of mitosis (Russell, P. and P. Nurse, *Cell* 45:145–153 (1986); Edgar, B. A. and P. H. O'Farrell, *Cell* 57:177–187 (1989)), whereas the cdc13 encoded B-type cyclin is essential for M-phase, but does not serve as a dose-dependent activator. Indeed, in many cell types, including the fission yeast, B-type cyclins accumulate and associate with cdc2 long before the tyrosine dephosphorylation event at the onset of M-phase (Booher, R. N. et al., *Cell* 58:485–497 (1989)). In some somatic cell types, the cdc25 gene is under transcriptional control, and very probably the cdc25 protein itself is regulated in a variety of ways that are not presently understood. In the early embryos of Xenopus, a somewhat different situation holds. As shown herein, the abundance of cdc25 is invariant during the cell cycle. Cyclin is the only protein that has to be synthesized during each round of activation and inactivation of MPF (Murray, W. W. et al., *Nature* 339:280–286 (1989)). It has been proposed that, in this context, cyclin must accumulate to a critical threshhold before pre-MPF is activated (Evans, T. et al., *Cell* 33:389–396 (1983); Pines, J. and T. Hunt, *EMBO J.* 6:2987–2995 (1987); Minshull, J. et al., *Cell* 56:947–956 (1989); Murray, A. W. and M. W. Kirshner, *Nature* 339:280–286 (1989)). Based on work described herein, it appears that this threshhold marks the point at which sufficient cyclin has accumulated to allow activation of the continuously present cdc25 phosphatase.

The present findings may throw light on the long obscure phenomenon of MPF autoactivation. If a small amount of MPF is injected into a frog oocyte, a much larger amount can subsequently be retrieved (Masui, Y. and C. L. Markert, *J. Exp. Zool.* 177:129–146 (1971); Smith, L. D. and R. E. Ecker, *Dev. Biol.* 25:232–247 (1971)). The present work shows that in this situation, the abundance of cdc2, cyclin B and cdc25 do not change (Gautier, J. and J. Mailer, *EMBO J.* 10:177–182

(1991); Example 11). It has been implicitly assumed that active cdc2/cyclin B phosphorylates some protein (possibly cdc25 itself), causing the activation of cdc25 and, thus leading to further activation of pre-MPF. This may be correct, but if cyclin B directly activates cdc25, in the absence of cdc2, as shown herein, all of the elements needed for an autoactivation loop exist among the cdc2, cyclin B and cdc25 proteins themselves.

A Common Motif in PTPases and Cyclins

Visual comparison of cdc25 A and B with known tyrosine PTPases, and also other proteins involved in cell cycle control, resulted in the following unexpected observations. First, the region of cdc25 that is immediately C-terminal to the putative catalytic domain (CA) is not highly related to other known PTPases, such as cytoplasmic PTPases from higher eukaryotes and the vaccinia virus serine-tyrosine phosphatase (VH-1, Guan, et al., 1991, FIG. 8A). Second and more interestingly, this region within the PTPases was found to contain sequence similarity to cyclins, particularly of the B-type (FIG. 8A). The similarity is detected immediately at the junction of the so-called cyclin-box and included some nearly invariable residues among cyclins (NB, the alignment in FIG. 8A optimizes the similarities between cdc25 proteins and PTPases, and also between PTPases and cyclins, but ignores the much greater homology within each of the three groups of proteins). In the region of similarity between PTPases and cyclins, referred to as the cyclin region (CR), there is no equivalent in the cdc25 proteins.

The newly found motif lies almost immediately adjacent to the domain (V/IXHCXXXXR), that has been directly implicated in the catalytic function of the PTPases and cdc25 protein (Krueger, N. S. et al., *EMBO J.* 9:3241–3252 (1990); Guan, K. and J. E. Dixon, *Science* 249:553–556 (1990); Guan, K. et al., *Anal. Biochemistry* 192:262–267 (1991); Gautier, J. et al., *Cell* 67:197–211 (1991)). This finding allows the following speculation. The catalytic activity of the other PTPases is considerably greater than that of cdc25, at least as determined in this study. cdc25 lacks the motif that is shared by cyclins and other PTPases. This motif may be an activating domain which, in the case of cde25, is provided in "trans" by intermolecular interaction with cyclin (FIG. 8), although in most PTPases it functions in "cis".

There is some similarity between PTPases and all of the classes of cyclin, whereas only B-type cyclins can activate cdc25. It is apparent, however, that the similarity is greatest between PTPases and cyclins of the B class. The differences between the various classes of cyclins within this region might be related to the specific ability of B but not A or D-type cyclins to activate cdc25 A.

Specific Interaction of cdc25 with Cyclin B

Figure 6:
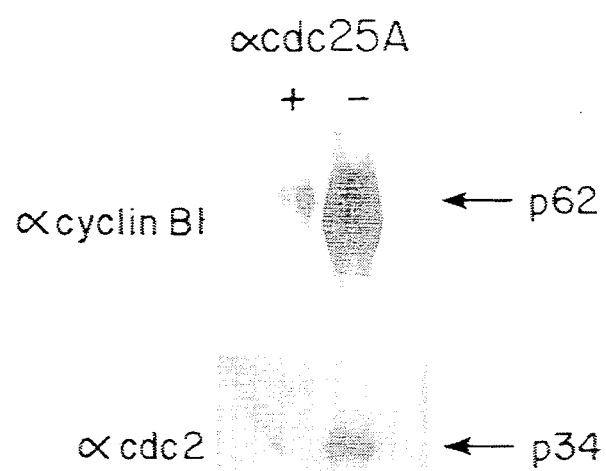
FIG. 6 shows the association between cdc25A and cyclin B1. Immunoprecipitation of the human cdc25 A protein complexes were performed as described in the Experimental procedures. Immunoblotting of the cdc25 A immunoprecipitates were done with the anti-cyclin B1 (kindly provided by J. Pines) or anti-cdc2 antibody (G6). − and + indicate presence or absence of the antigenic peptide in the immunoprecipitation reaction. Positions of the p62 (cyclin B1) and p34 (cdc2) are indicated.

As shown in Example 13, cdc25 stably associates with a cdc2 complex and this interaction is periodic during the division cycle of Xenopus embryos. Human cyclin B1 is found in the complex with cdc25 A (FIG. 6). It seems likely that the periodicity of the interaction between cdc25 and cdc2 is mediated at least in part by periodic accumulation and degradation of cyclin during the cell cycle.

As described herein, it has been established that cdc25 can function as an enzyme with respect to RCML, PNPP and cdc2 derived peptide substrates. A low observed catalytic rate was evident and may reflect the use of RCML or peptide as an artificial substrate. However, it is not clear what catalytic rate is required in vivo. If cdc25 does indeed associate with cdc2/cyclin B as suggested herein (Example 9 and FIGS. 6 and 8), the PTPase may not function in a conventional catalytic reaction, but rather only after formation of a cdc25/cyclin B/cdc2 complex. Under such conditions, the catalytic reaction is essentially intramolecular and Michaelis/Menten kinetics do not pertain.

Inhibition by p13 of Human cdc25 Phosphatase Activity

The p13 protein encoded by the sucl gene is an essential subunit of the cdc2 protein kinase. The gene was isolated by virtue of its ability to rescue a fission yeast cdc2-33 allele on a multicopy plasmid (Hayles, J. et al., *EMBO J.* 5:3373–3379 (1986)). However, overexpression of the gene is inhibitory for mitosis (Hindley, J. et al., *Mol. Cell. Biol.* 7:504–511 (1987); Hayles, J. et al., *Mol Gen. Genet.* 202:291–293 (1986)). In vitro, p13 can inhibit activation of pre-MPF (Dunphy, W. et al., *Cell* 54:423–431 (1988); Dunphy, W. and J. W. Newport, *Cell* 58:181–431 (1989)).

The present work may clarify two previously confusing issues related to these observations. First, p13 can bind to cdc2 in the absence of cyclins (Brizuela, L. et al., *EMBO J.* 6:3507–3514 (1987); Example 6), but activation of cdc2/cyclin B that is pre-bound to p13-sepharose can be inhibited by excess exogenous p13 (Jessus, C. et al., *FEBS LETTERS* 266:4–8 (1990)). By contrast, fully activated cyclin B/cdc2 is not inhibited by excess p13 (Dunphy, W. et al., *Cell* 54:423–431 (1988); Arion, D. et al., *Cell* 55:371–378 (1988); Maijer, L. et al., *EMBO J.* 8:2275–2282 (1989)). This suggests, as previously proposed (Jessus, C. et al., *FEBS LETTERS* 266:4–8 (1990)), that there are at least two binding sites for p13. One is presumably a high affinity binding site on cdc2 itself, that accounts for the extraordinary efficiency of p13-sepharose chromatography (FIG. 8B). The other site, of lower affinity requiring p13 in the 20 micromolar range, does not affect fully activated cdc2/cyclin B, but can inhibit activation of pre-MPF. Because direct inhibition of cdc25 A endogenous phosphatase activity by p13, in the total absence of cdc2, has been observed (Example 6), it is reasonable to attribute the second binding site not to cdc2, but to cdc25 (FIG. 10b). This is probably an unstable interaction, quite unlike that between p13 and cdc2.

Second, there has been some dispute concerning the inhibition of cdc25 by p13 in different experimental contexts. In some cases, p13 has been inhibitory (Gautier, J. et al., *Cell* 67:197–211 (1991)) and in other not (Kumagai, A. and W. G. Dunphy, *Cell* 64:903–914 (1991)). As described herein under the conditions used, cdc25 A is inhibited by p13 and cdc25 B is not. The two proteins have many regions of structural dissimilarity, that could readily account for this effect.

cdc25 Does Not Change in Abundance During Cell Cycle

Figure 11A:
Figure 11B:
Figure 11C:

Surprisingly, the Xenopus cdc25 does not oscillate in abundance, either during meiotic maturation, or during the early embryonic division cycles. The protein does, however, physically associate with the cdc2/cyclin B complex in a cell cycle dependent manner (see Examples 5 and 10). Maximal association is found just before or at the time of maximal kinase activity (FIG. 11C, FIG. 12G and FIG. 13). The cdc2 that is associated with cdc25 is tyrosine dephosphorylated and active as a histone H2 kinase. The association between cdc25 and the cdc2/cyclin B complex could be mediated either by cdc2 or by cyclin B. As described herein, B-type cyclins were shown to be able to directly activate the intrinsic PTPase activity of cdc25 proteins in the absence of cdc2. This suggests that the interaction between cdc25 and the cdc2/cyclin B complex is probably mediated by cyclin.

These results bear upon the mechanism by which cdc2 becomes activated at M-phase. cdc25 acts in mitosis to cause the tyrosine dephosphorylation of cdc2, as described herein. The demonstration of direct physical association between cdc25 and the cdc2/cyclin B complex is entirely consistent with this hypothesis. The finding that approximately 5% of cdc2 associates with cdc25 at M-phase raises certain questions. It is possible that one molecule of cdc25 binds to cdc2/cyclin B, activates the kinase and then dissociates to repeat the process in a conventional catalytic mechanism. Alternatively, a single molecule of cdc25 might activate only a single molecule of pre-MPF in a stoichiometric mechanism. Only a fraction of the total amount of cdc2 (10% of the cellular cdc2 content, Kobayashi A. H. et al., *J. Cell Biol.* 114:755–765 (1991)) is bound to cyclin B and activated at M-phase in Xenopus eggs. The finding that only 5% of total cdc2 is associated with cdc25 at mitosis might reflect the relatively low abundance of cyclin B compared to cdc2, if the interaction is mediated by cyclin B. This is confirmed by the fact that, in comparison to the 5% cdc25-associated cdc2, a larger amount of cyclin B2 is found in association with cdc25 (17% of the full cellular amount of cyclin B2). Moreover, a considerable fraction of cdc25 is involved in this association (20% of the cellular content).

Identification of Additional cdc25 Genes and Cell Cycle Regulation by the Present Invention Using methods described herein, such as in Examples 1 and 7, additional members of the human cdc25 gene family and cdc25 genes in other organisms can be identified and isolated, as well as the encoded products. For example, all or a portion of the nucleotide sequence of the cdc25 A gene or the cdc25 B gene (see FIG. 1) can be used, in hybridization methods or amplification methods known to those of skill in the art, (Sambrook, et al., *Molecular Cloning: A Laboratory Manual*, Cold Spring Harbor Laboratory, New.York (1989). For example, a nucleotide sequence which is all or a portion of the cdc25 A gene or the cdc25 B gene can be used to screen a DNA library of human or nonhuman origin for additional cdc25 genes. DNA sequences identified in this manner can be expressed and their products analyzed for tyrosine specific phosphatase activity, such as by the methods described herein (see Experimental Procedures and Example 2). Hybridization conditions used can be varied as desired. If a nucleotide sequence which is exactly complementary to the probe used is to be isolated, conditions of either high or low stringency can be used; if a nucleic acid sequence less related to those of the probe is to be identified, conditions of lower stringency are used. The present invention includes the cdc25 A and cdc25 B genes and equivalent cdc genes, which are nucleic acid sequences which hybridize to all or a portion of the cdc25 A or cdc25 B gene or a complement of either gene and encode a tyrosine PTPase which has substantially the same catalytic function as the cdc25 A or cdc25 B gene product. The polymerase chain reaction and appropriately designed primers can also be used to identify other cdc25 genes. Alternatively, an anti-cdc25 A or anti-cdc25 B antibody can be used to detect other (recombinant) cdc25 gene products expressed in appropriate host cells transformed with a vector or DNA construct thought to encode a cdc25 product. The cdc25 A gene, cdc25 B gene and equivalent cdc genes which are the subject of the present invention include those obtained from naturally occurring sources and those produced by genetic engineering (cloning) methods or by synthetic methods. These genes can be used to produce the encoded cdc25 A, cdc25 B or other cdc25 gene product, which can, in turn, be used to produce antibodies specific for the product or to regulate cell cycle activation (cdc2 kinase activation), as described below.

The present invention also includes PTPase genes which encode PTPases which are related to cdc25 PTPases but are specifically activated by a non-B type cyclin (e.g., by cyclin A, cyclin D). These PTPases are referred to herein as cdc25-related PTPases and their activation by a cyclin, their ability to activate cdc2 or another molecule and their role in regulation of the cell cycle can be assessed using the methods described for determining the role of cdc25.

The present invention also provides a method by which the level of expression or activity of cdc25 PTPases in a cell can be determined and assessed (i.e., to determine if they increased, decreased or within normal limits). Because the cdc25 gene is increased (over expressed) in certain tumor types, the present invention also provides a method of diagnosing or detecting over expression related to those tumor cell types. In the method, a gene probe can be used to detect and quantify the cdc25 gene in cells or antibodies specific for the cdc25 PTPase can be used.

A method of inhibiting activation of cdc25 PTPases, activation of cdc2 kinase(s) and, thus, initiation of mitosis (cell division) is also possible. For example, activation of cdc25 PTPase is inhibited (reduced or prevented) by introducing into cells a drug or other agent which can block, directly or indirectly, complexing of cdc25 with cyclin B or the cyclin B/cdc2 complex and, thus, directly block activation of the cdc25 and indirectly block activation of the cdc2 kinase. In one embodiment, complex formation is prevented in an indirect manner, such as by preventing transcription and/or translation of the cdc25 DNA and/or RNA. This can be carried out by introducing antisense oligonucleotides into cells, in which they hybridize to the cdc25-encoding nucleic acid sequences, preventing their further processing. It is also possible to inhibit expression of the cdc25 product by interfering with an essential cdc25 transcription factor. Alternatively, complex formation can be prevented indirectly be degrading the cdc25 gene product(s), such as by introducing a protease or substance which enhances their breakdown into cells. In either case, the effect is indirect in that a reduced quantity of cdc25 is available than would otherwise be the case. In another embodiment, activation of cdc25 PTPase is inhibited by interfering with the newly identified region of cyclin which has been shown to share sequence similarity with a region present in other PTPases, but not present in cdc25, and which appears to be provided to cdc25 in trans, by intermolecular interaction with cyclin.

In another embodiment, activation of cdc25 PTPase is inhibited in a more direct manner by, for example, introducing into cells a drug or other agent which binds the PTPase and prevents complex formation with cyclin (and, thus, prevents PTPase activation). Alternatively, a drug or other agent which interferes in another manner with the physical association between cyclin and the PTPase (e.g., by intercalation) or disrupts the catalytic activity of the enzyme can be introduced into cells. This can be effected, for example, by use of antibodies which bind the PTPase or the cyclin or a peptide or low molecular weight organic or inorganic compound which, like the endogenous type B cyclin, binds the cdc25 PTPase, but, unlike type B cyclin does not result in activation of the enzyme or results in its being disabled or degraded. Peptides and small organic compounds to be used for this purpose can be designed, based on analysis of the amino acid sequences of B type cyclins or of the amino acid sequences of the cdc PTPase(s) involved. They can be designed, for example, to include residues necessary for binding and to exclude residues whose presence results in activation. This can be done, for example, by systematically mapping the binding site(s) and designing molecules which recognize or otherwise associate with the site(s) necessary for activation, but do not cause activation. One site of particular interest for this purpose is the region which, as described above, is missing in cdc25 PTPases and appears to be provided in trans by intermolecular binding of the cdc25 product and type B cyclin. At least three possible approaches are possible in this instance. First, a molecule (e.g., a peptide which mimics the binding site on type B cyclin for cdc25 can be introduced into cells, in which it binds cdc25 and blocks its interaction with cyclin. Second, a molecule which mimics the region of cdc25 which binds the type B cyclin molecule can be introduced into cells, in which it binds cyclin and blocks the cdc25-cyclin complex formation. Third, a molecule which inhibits or inactivates the putative activating domain on type B cyclin, can be introduced into cells, thus preventing activation of the cdc PTPase.

In another embodiment, inhibitors of the catalytic activity of cdc25 PTPase are introduced into cells. Such inhibitors are low molecular weight agents, such as peptides and inorganic or organic compounds.

The present invention also includes a method of screening compounds or molecules for their ability to inhibit the function of cdc25 protein or binding of the cdc25 protein with the cyclin/cdc2 complex. For example, cells as described herein, in which a cdc25 gene is expressed, can be used. A compound or molecule to be assessed for its ability to inhibit cdc25 protein function or binding to the cyclin/cdc2 complex is contacted with the cells, under conditions appropriate for entry of the compound or molecule into the cells. Inhibition of the cdc25 protein or of complex formation will result in arrest of the cells or a reduced rate of cell division. Comparison with cell division of an appropriate control (e.g., the same type of cells without added test drug) will demonstrae the ability or inability of the compound or molecule to inhibit the cyclin. Alternatively, an in vitro assay can be used to test for compounds or molecules able to inhibit cdc25 PTPases or their binding to the cyclin/cdc25 complex. In this in vitro assay, the three components (cdc25 PTPase, cyclin and cdc2 (the latter two either individually or as a cyclin/cdc2 complex such as inactive cyclin/cdc2 complex from interphase cells) are combined with a potential cdc25 inhibitor. The activity of the potential inhibitor is assessed by determining whether cdc25 binds cyclin or a cyclin/cdc2 complex or whether cdc2 is activated, as evidenced by histone kinase activity. This method can make use of the teachings of Jessus et al. (*FEBS Letters* 266:4–8 (1990)) and DuCommun and Beach (*Annal. Biochem.* 187:94–97 (1990)), the teachings of which are incorporated herein by reference. For example, in an assay for cdc25 inhibitors, inactive cyclin/cdc2 complex can be placed in the wells, cdc25 and a test compound or molecule added to wells and cdc2 activation assessed. In the presence of a cdc25 inhibitor, cdc2 activation will be prevented or reduced (less than would occur in the absence of the test compound or molecule).

Existing compounds or molecules (e.g., those present in fermentation broth or a chemical "library") or those developed to inhibit the cyclin activation of its protein kinase can be screened for their effectiveness using this method. Drugs which inhibit cdc25 protein catalytic activity, inhibit complex formation or degrade or otherwise inactivate cdc25 are also the subject of this invention.

The present invention will now be illustrated by the following examples, which are not intended to be limiting in any way.

EXPERIMENTAL PROCEDURES

The following experimental procedures were used in carrying out the work described in Examples 1–6.

Molecular Cloning of the Human cdc25 Homologues cDNA

Three highly degenerate primers corresponding to the consensus cdc25 protein sequence were designed taking into account homology between the S. pombe cdc25, Drosophila string and *S. cerevisiae* mihl gene products. 5' degenerate primers corresponding to the amino acid sequence IIDCRT/FP (or E) Y E (SEQ ID #24) SIC-1: ATIATIGATTGCCGITA/TC-CCITAC/TGA (SEQ ID #25) and SIC-2; ATIATI-GATTGCCGITA/TCGAITAC/TGA) (SEQ ID #26) and a 3' primer corresponding to the amino-acid sequence I/V F H C E F (ST-C: A/TA/GAAC/TT-CA/GCAA/GTGA/GAAA/G/TA) (SEQ ID #29), where I corresponds to inosine, were prepared. The 50 ml PCR reaction mixture contained 50 mM KCl; 10 mM TrisHCl(pH 8.3); 1.5 mM MgCl$_2$; 0.01% gelatin; 0.2 mM each of dATP, dCTP, dGTP and dTTP; 0.5 unit of *Thermus uaticus* (AmpliTaq DNA polymerase (Perkin-Elmer/Cetus), 2 mM each of the 5' primers (SIC-1 and SIC-2) and 5 mM of the 3' primer (ST-C) and 100 ng of human N-Tera cells cDNA library made in ggt10 by Jacek Skowronski (Cold Spring Harbor Laboratory). Forth cycles of 94° C. for 1 min, 40° C. for 3 min and 72° C. for 1 min were performed in a DNA thermal cycler (Perkin-Elmer/Cetus). The reaction products were separated on the 2% agarose gel and the expected size approximately 160 bp) fragments were subcloned into Smaldigested pBluescript SK(−) vector (Stratagene, La Jolla, Calif.). Nine clones were sequenced with the sequence clearly indicating cloning of cdc25 homologues. Two different PCR products were detected. One of them was almost identical to recently cloned human cdc25 homologue (CDC25Hs, Sadhu, K. et al., *Proc. Natl. Acad. Sci. USA* 87:5139–5143 (1990)) and another correspond to a previously uncharacterized cDNA here called cdc25 A. The N-Tera cdc25 A PCR-derived clone (p5w1) was used to screen the human N-Tera cell library at low stringency. After plaque purification inserts of nine positive clones were subcloned into the EcoRI site of the pBluescript SK(−) plasmid. Inserts from two phages containing the entire open reading frame of the cdc25 A cDNA were analysed by restriction mapping (plasmids 4g1.3 and 211.1, containing inserts of 2.4 and 3.9 kb). Plasmid 4g1.3 contained a deletion of 1.4 kb at the 3′ untranslated region of the cDNA and was chosen for complete sequencing. Sequence analysis was performed on both strands using a chain termination method (Sanger, et al., 1977) on an automated sequencing system (Applied Biosystems 373A).

Further analysis indicated that one of the original nine phage clones corresponds to a different cdc25 homolog; this is designated cdc25 B. This phage gave rise to two EcoRI fragments (0.9 and 1.5 kb) but did not represent a whole open reading frame. In order to obtain a complete cDNA, the same library was screened with the 0.9 kb EcoRI fragment and an insert representing a complete cDNA (3.0 kb) was subcloned via partial digestion with EcoRI into the pBluescript SK(−) vector. This was used for sequencing.

Production of Antipeptide Antiserum to Human cdc25 A and CDC25Hs

Peptides corresponding to the amino acid sequence CQGALNLYSQEELF-NH$_2$ (SEQ ID #28) (CDC25Hs or cdc25 C) and CKGAVNLHMEEEVE-NH$_2$ (SEQ ID #29)(cdc25 A) were synthesized at the Cold Spring Harbor Laboratory protein core facility, HPLC-purified and coupled to keyhole limpet hemocyanine (KLH) and bovine serum albumin essentially as described (Draetta, G. et al., Nature 336:738-744 (1988)). Rabbits were injected with 200 mg of KLH-peptide conjugate every three weeks. Positive sera were obtained after three booster injections. Antigody (K143 and K144) were affinity purified on the BSA-peptide conjugates coupled to the CNBr-Sepharose (Pharmacia, Sweden) according to the manufacturers instructions. No crossreactivity between peptide #134 and K144 antiserum with the other peptide was detected.

Rescue of the Fission Yeast cdc25 Temperature Sensitive Mutant

A 2.0 kb NcoI-BamHI fragment encoding amino acids 1-526 of human cdc25 A from the p4g1.3 plasmid were subcloned into NcoI-BamHI digested pARTN, resulting in the pARTN-cdc25 A construct harboring human cdc25 A cDNA in sense orientation to the constitutive adh promoter. pARTN is derived from the pART3 (McLeod, et al., 1987) by ligation of an NcoI linker (New England Biolabs) into the SmaI site. An 2.4 kb SmaI fragment from the p4×1.2 plasmid encoding amino acids 32-566 was subcloned into SmaI digested pART3 vector (containing LEU2 marker) resulting in pARTN-cdc25 B cDNA. Both plasmids were transformed into S.pombe H+cdc25-22 leu1-32 (SP 532) strain. Leu+transformants were obtained at 26° C.

Cell Culture,Immnoprecipitation

HeLa cells (obtained from the ATCC) were grown at 37° C. in Dulbecco modified Eagle's media (DMDM) supplemented with 10% fetal calf serum. For labelling, cells were washed with methionine minus media (Gibco) and supplemented with 1 mci/ml $^{35}$S.methionine (Translabel, ICN) for 6-8 hours. Cells were lysed essentially as described (Draetta, G. et al., Nature 336:738-744 (1988)) or in the EB buffer (80 mM glycerophosphate, 15 mM MgCl$_2$ 20 mM EGTA, 1 mM DTT), supplemented with protease inhibitors (0.5 mM PMSF, 1 mg/ml of aprotinin, pepstatin, chymostatin, leupeptine, 30 mg/ml of TPCK, 15 mg/ml benzimidine). Lysates were precleared with protein A-Sepharose beads (Pharmacia) (20 ml of the 1:1 slurry), anti-human cdc25 A antiserum (K144) were added (1–5 ml) and after 8–10 hours immune complexes were precipitated with protein A-beads (20 ml of the 1:1 slurry). Beads were washed four times with the lysis buffer and resuspended in 20 ml 2×sample buffer (Laemmli, U.K. Nature 227:680-685 (1970)). Immunoprecipitated proteins were resolved on the 10% polyacrylamide gels, containing SDS and visualized by the autoradiography of the dried gel slabs (Anderson, S. J. et al., J. Virol. 51:730–741 (1984)). p13 beads were prepared and used to precipitate p34$^{cdc2}$ from HeLa as described earlier (Brizuela, L. et al., EMBO J. 6:3507–3514 (1987)).

Bacterial Expression of the cdc25 A and cdc25 B Phosphatase Assay

A plasmid containing the entire open reading frame of human cdc25 A was digested with Nco1 (at amino acid 1), blunt ended with T4 DNA polymerase, heat inactivated, extracted with phenolchlorophorm, ethanol precipitated and digested with EcoRI. The resultant 2.0 kb fragment was gel-purified and ligated into pGEX-2T SmaI/EcoRI digested vector. Resultant plasmid upon transformation into bacteria gave rise to a 90 kd IPTG-inducible protein. Expressed fusion protein was recovered as described (Smith, D. B. and K. S. Johnson, Gene 67:31-40 (1988)) on glutathione-Sepharose beads (Pharmacia), and eluted with 5 mM freshly prepared glutathione in 50 mM TrisHCl, 50 mM NAGl, 0.1 mMEDTA, 1 mM DTT, pH 8.0. For expression of cdc25 B, plasmid p4×1.2 was cut with XbaI, then with SmaI (partially) and the 2.4 kb fragment was subcloned into SmaI/XbaI cut pGEX-KG vector (Guan, K. and J. E. Dixon, Science 249:553–556 (1991)). Expression of this construct resulted in IPTG-dependent synthesis of the 88 kD GST-cdc25 B fusion protein. Phosphatase activity of the purified cdc25 A protein (4.5 mg or 50 pmoles) was assayed in 0.5 ml 20 mM Tris HCl, pH 8.0, 1 mM EDTA, 0.1% b-mercaptoethanol, 20 mM p-nitrophenylphosphate (PNPP). Absorbance at 410 nm was determined using a molar absorptivity of $1.78 \times 10^4 M^{-1} cm^{-1}$ to calculate the concentration of the p-nitrophenolate ion generated in the assay. For cdc25 B the assay was performed in the same buffer except at pH 8.8.

Reduced carboxamidomethylated and maleylated lysozyme (RCML) was obtained from N. Tonks in a $^{32}$P-tyrosine phosphorylated form. Approximately 50% of the protein was phosphorylated. $^{32}$P-labeled RCML was used in the phosphatase assay in 50 mM Tris HCl, pH 8.0, 50 mM NaCl, 0.1 mm EDTA, 1 mM DTT at a final phosphate concentration of 10–30 mM. Reactions (30–50 ml) were performed at 30° C. for 10 or 20 min, and after addition of the fatty acid free bovine serum albumin (BSA, Sigma) to 2 mg/ml, proteins were precipitated with 200 ml of 20% trichloroacetic acid, vortexed, incubated at −70° C. for 5 min, thawed, spun in an Eppendorf centrifuge for 5–10 min at the maximal speed and 200 ml supernatants were counted in 2 ml Aquasol (NEN) for 10 min.

Peptide, corresponding to region of p34$^{cdc2}$ undergoing inhibitory tyrosine phosphorylation (NH$_2$-CKKKVEKIGEGTYGVVYK) (SEQ ID #30) (peptide sequence which is additional to cdc2 and added for the reasons of coupling the peptide to the beads and/or proteins is underlined) was phosphorylated in vitro using bacterially produced v-Abl (Oncogene Sciences) at conditions described by manufacturer and purified on the Seppak column (Millipore). Final activity incorporated into peptide was 0.7×10$^5$ cpm/mg. Phosphatase activity of the cdc25 A protein against peptide (1 mg of peptide were used in each sample) was assayed at the same conditions as for RCML. Reaction mixture was incubated with acid charcoal as described (Streuli, M. et al., Natl. Acad. Sci. USA 86:8698–8702 (1989)) and 200 ml from total supernatant of 700 ml were counted as described above.

Expression of Cyclin Proteins

In order to express human cyclins in bacteria we prepared modified pGEX-3X vector (pGEX-Nco) first by digesting it with SmaI, followed by ligation of the Nco1 linker (described earlier in Experimental procedures), resulting in a vector where cloning into Nco1 site resulted in the proper expression of the foreign cDNA. Human cyclin B1 and A were synthesized by PCR and their sequence was fully confirmed. cyclin B1 cDNA in the pBluescript SK(−) was cut with Nco1/-Sma1 and the resultant 1.3 kb fragment was ligated into pGEX-Nco, digested with EcoRI, filled in with Klenow fragment and cut with Nco1. The sequence of cyclin A, including the first ATG codon was changed to an nco1 site by PCR. To express cyclin A, plasmid contained complete open reading frame for cyclin A (p4f1.1) were digested with Nco1 and EcoRI and resultant 1.4 kb insert was subcloned into pGEX-Nco, cut with Nco1/EcoRI. Human cDNA, encoding human cyclin B2 was obtained from Y.Xiong, unpublished, with the first ATG codon changed by PCR to Nco1 site, digested with BamHI, blunt ended with T4 DNA polymerase, digested with the Nco1 and the resultant 1.3 kb fragment was ligated in the pGEX3X-Nco vector prepared as described above for the ligation of cyclinB1 cDNA. Mouse CYL1 (cyclinD1) cDNA in the pGEX3X vector was generous gift from Dr. C. Sherr. Purification of the expressed cyclins were performed essentially as described (Smith, D. B. and K. S. Johnson, Gene 67:31–40 (1988); Solomon, M. J. et al., Cell 63:1013–1024 (1991)), except that after the first extraction, the cell pellets were resuspended in the 50 mM TrisHCl, pH 8.0, 50 mM NAGl, 1 mM EDTA, 1 mM DTT, 1% glycerol, 2M urea and extracted for 10 min on ice. After centrifugation for 30–60 min at 15000 rpm on the RC-5B centrifuge (Beckman) the supernatant was filtered through 0.22 mm filter (Millipore) and applied on the 2 ml glutathione-Sepharose column (Pharmacia), equilibrated with the extraction buffer. columns were washed subsequently with the extraction buffer (10 ml), then with the same buffer lacking urea (10 ml) and fusion proteins were eleuted in the same buffer supplemented with the 10 mM glutathione. Eluted proteins were dialized into phosphatase assay buffer and concentrated by repeated dilution-concentration on the Amicon microconcentrators. Protease inhibitors (PMSF and benzimidine) were added to 0.5 and 5 mM subsequently and the proteins were stored at 4° C. for 2–3 days or used immediately on the same day.

The Bradford assay was used to determine protein concentration.

Microinjection of Antibodies

For microinjection experiments HeLa cells wre grown to 20–30 cells in an "island" and injected at time 0 with affinity purified K144 (1 mg/ml) further depleted on the #143 peptide conjugated BSA sepharose. The injection was done in buffer F (20 mM Tris Hcl, pH 7.6, 20 mM NaCl, 50 mM KCl, 0.5 mM b-mercaptoethanol, 0.1 mM ATP). All cells in the particular "island" were microinjected and photographs were taken 8, 18, 24 and 36 hours after microinjection. In a separate set of experiments cells were photographed at 8, 12, 18 and 24 hours after injection. Microinjection of the protein A-Sepharose purified rabbit IgG from the preimmune serum served as a control.

Protein Kinase Assays

For protein kinase assays, p13 beads with bound p34$^{cdc2}$ kinase isolated from the HeLa cells (incubated in the presence of hydroxyurea (10 mM) for 22 hours followed by 4 hour release) were washed twice in the buffer containing 50 mM Tris HCl, pH 8.0, 1 mM EDTA, 1 mM DTT and incubated for 5 min at 30° C. with the additives. These included buffer alone or material eluted with the 0.1M glycine/HCl, pH 2.5 from the cdc25 A immunoprecipitates, done in the presence or absence of the 1 mg of an antigenic peptide (before addition material was neutralized with 1M Tris HCl, pH 8.0). The precipitates were washed twice with 50 mM Tris HCl, pH 8.0, 10 mM MgCl$_2$, 1 mM DTT (PK-buffer) and finally resuspended in 2 volumes of PK buffer supplemented with 5 mM ATP, 10 mCi of [q−$^{32}$P] ATP (3000 Ci/mmol), 50 mg/ml of histone H1. After incubation for 15 min at 30° C. the reaction was stopped by polyacrylamide gel sample buffer containing SDS. Labeled proteins were separated on 10% polyacrilamide gels and detected by autoradiography.

EXAMPLE 1

ISOLATION OF cdc25 A AND cdc25 B cDNA

A human cdc25 gene has previously been described (Sadhu, K. et al., Proc. Natl. Acad. Sci. USA 87:5139–5143 (1990)). Further members of what is now shown to be the human cdc25 family have been isolated by means of a PCR-based strategy. This strategy made use of three degenerate oligonucleotide primers designed to correspond to amino-acid regions of consensus between Drosophila melanogaster string (Edgar, B. A. and P. H. O'Farrell, Cell 57:177–187 (1989)), S. pombe cdc25 (Russell, P. and P. Nurse, Cell 45:145–153 (1986)) and S. cerevisiae mihl (Russell, P. et al., Cell 57:295–303 (1989), see experimental procedures). Amplification of cDNA from a human N-Tera teratocarcinoma library, followed by cloning of the PCR products into phagemid vector, allowed nucleotide sequencing of the fragments. This established that a cdc25-related fragment different from that previously described (Sadhu, K. et al., Proc. Natl. Acad. Sci. USA 87:5139–5143 (1990)) had been cloned.

The insert from one PCR-derived clone (p5w1) was used to screen a human cDNA library in the ggt10 vector. From approximately 10 plaques screened, nine positive clones were obtained. Eight corresponded to the originally cloned PCR product used as the hybridization probe. This is referred to as cdc25 A. A second cdc25 clone, isolated by using low stringency hybridization with p5w1, is called cdc25 B (see experimental procedures). The longest cDNA clones of cdc25 A and B were subjected to nucleotide sequencing. The region of each that contains the open reading frame is shown (FIG. 1). cdc25 A and cdc25 B are predicted to encode proteins of 526 and 566 amino acids respectively. The calculated isoelectric point for cdc25 A is 6.3 and for cdc25 B is 5.9. Both genes have an initiation codon flanked by a Kozak consensus sequence (PuCC-/GATGG) (Kozak, M. Cell 44:283–292 (1986)).

Comparison of the amino acid sequence of cdc25 A and cdc25 B and the GenBank data base (release 67) revealed homology to the previously described human cdc25 (Sadhu, K. et al., Proc. Natl. Acad. Sci. USA 87:5139–5143 (1990)), referred to herein as cdc25 C. This comparison showed that there is 48% identity in the 273 C-terminal region between cdc25 C and A, and 43% identity between C and B. (FIG. 2) Drosophila string shares 34.5% identity to cdc25 A in a 362 amino acid region and 43.9% in a 269 amino acid region with cdc25 B (FIG. 2). *S. pombe* cdc25+ is also related to both cdc25 A and B, though at a lesser level (FIG. 2). Human cdc25 A and cdc25 B proteins also contain conserved amino acids that characterize the "cdc25-box", particularly those in the region potentially involved in cdc25 catalytic activity (L/VFHCEXXXXR) (SEQ ID #30) (Moreno, S. and P. Nurse, Nature 351:194 (1991); Gautier, J. and J. Maller, EMBO J. 10:177–182 (1991)). All known human cdc25 homologues contain a stretch of 15 identical amino acids in this region (FIG. 2). Interestingly, the overall similarity between different human cdc25 proteins does not greatly exceed that between humans and such evolutionary distinct species as Drosophila.

EXAMPLE 2

Assessment of the Functional Relationship Between Proteins Encoded by Human cdc25 A, cdc25 B and Fission Yeast cdc25

To test whether the human cdc25 A and B genes do indeed encode proteins that are functionally related to fission yeast cdc25, the human genes were subcloned into the *S. pombe* autonomously-replicating expression vector, pARTN (carrying the LEU2 marker under the control of the constitutive alcohol dehydrogenase promoter, described in experimental procedures). After introduction of the plasmids into an H+ cdc25-22 leu1-32 strain, transformants were plated on media either lacking or containing leucine at a permissive (26° C.) or restrictive temperature (36° C.). Both human cDNAs could efficiently rescue the temperature-sensitive mutation of the cdc25 gene. Cells bearing human cDNAs were able to form single colonies with a growth rate similar to wild-type cells. Microscopic examination revealed that cells transformed with either gene were slightly wee, a phenotype previously observed in fission yeast transformed with the wild-type cdc25+ gene on the same type of vector (Russell, P. and P. Nurse, Cell 45:145–153 (1986)).

EXAMPLE 3

Demonstration That cdc25 A Acts in Mitosis

In order to test the role of cdc25 A, we prepared polyclonal antibodies against a peptide corresponding to an internal region of the cdc25 A protein (see experimental procedures). This serum was used to precipitate $^{35}$S-methionine labeled HeLa proteins. A protein of 75 kD was specifically precipitated in the absence, but not the presence, of competing antigenic peptide (FIG. 3A, left panel, note that stringent detergent conditions were used that abolish interactions with cdc2 and cyclin). This molecular weight is higher than predicted from the amino acid sequence of the gene. However, in vitro translation of the cdc25 A clone also yielded a protein of 75 kD (not shown). To test whether this protein might activate inactive cyclin B/cdc2, as described in the case of the Drosophila string protein (Kumagai, A. and W. G. Dunphy, Cell 64:903–914 (1991)) and also human cdc25 C (Strausfeld, U. et al., Nature 351:242–245 (1991)), HeLa cell cdc25 A was eluted from an immunocomplex under conditions of low pH (see experimental procedures). The eluted protein did not possess any histone kinase activity (FIG. 3A, right panel, lane 4). This protein was mixed with cdc2/cyclin B, prepared by p13-Sepharose precipitation of an extract of HeLa cells that had been arrested in hydroxyurea and released for four hours (see experimental procedures). Under these conditions, the cdc2/cyclin B is relatively inactive as a histone kinase (FIG. 3A, right panel, lane 1), unless the eluted cdc25 A protein is added (lane 3).

Figure 3C:
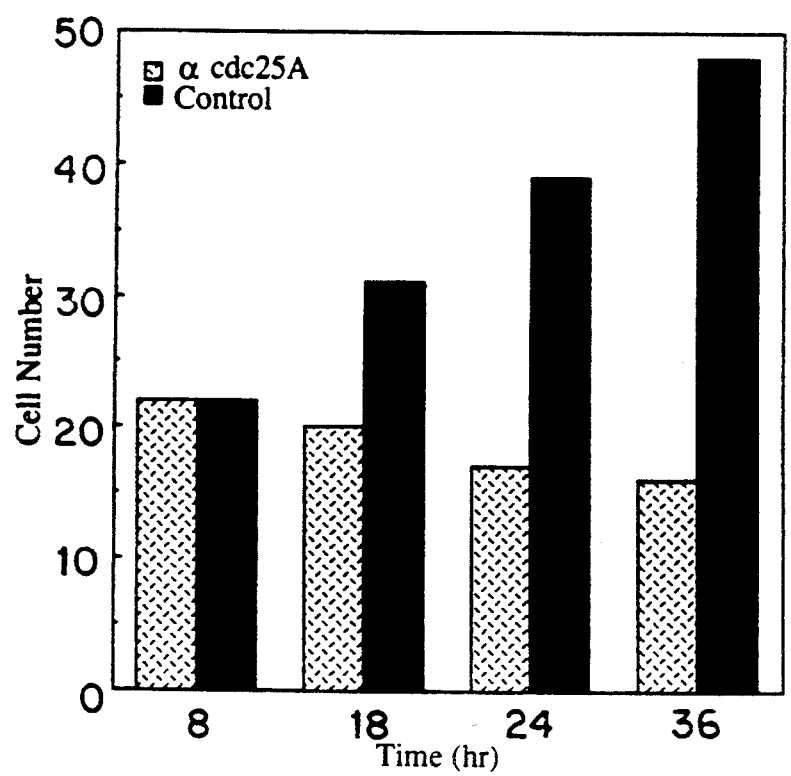
FIG. 3C. Estimation of cell numbers in islands of HeLa cells injected with control or experimental anti-cdc25 A affinity purified antibodies at time zero.

To address the function of cdc25 A protein in human cells, affinity-purified anti-peptide antibodies were microinjected into actively proliferating HeLa cells (see experimental procedures). Islands of injected cells were photographed at 8, 12, 18 and 24 hours, and in another set of experiments at 8, 12, 18, 24 and 36 hours later. In some cases, cells were stained with anti-rabbit IgG to confirm the success of the anti-cdc25 antibody microinjection. Analysis of the photographs in such three independent experiments led to the conclusion that the antibodies prevent cells from dividing (FIGS. 3B, 3C). Following microinjection of anti-cdc25 A, but not a control serum, the percentage of cells in mitosis (defined as rounded-up mitotic figures) increased progressively (FIG. 3B). The cell number in each injected island increased in the case of control serum, but gradually declined in the experimental. This is attributed to the failure of cells to divide, coupled with their eventual death (visualized as shrivelled rounded cells) and their dissociation from the surface of the culture plate. In fission yeast, loss of cdc25 function causes cells to arrest in G2, rather than in mid-mitosis as in the present experiment. This difference is discussed below. On the basis of sequence homology, function in fission yeast, and, in the case of cdc25 A, functional studies in human cells, the newly-identified human proteins can be classified as relatives of cdc25.

EXAMPLE 4

Activation of cdc25 by B-type Cyclin

In order to study the regulation of the cdc25 phosphatase activity in vitro, human cdc25 A and B were expressed in bacteria as fusion proteins with glutathione-S-transferase (GST, Smith, D. B. and K. S. Johnson, Gene 67:31–40 (1988)). Fusion proteins with a relative molecular weight of 90 kD (cdc25 A) and 88 kD (cdc25 B) were isolated by affinity chromatography on glutathione-Sepharose beads as described (see experimental procedures, Smith D. B. and K. S. Johnson, Gene 67:31–40 (1988)). Human cyclins A, B1, B2 and murine D1 (CYL1, Matsushime, H. et al., Cell 65:701–713 (1991)) were expressed as fusion proteins with GST; purified proteins were obtained by the same method.

To investigate the potential regulation of cdc25 activity by cyclin, it was necessary to find a substrate that bore no conceivable relationship to cdc2, the presumed physiological substrate of the phosphatase. cdc2 binds to cyclin (Draetta, G. et al., *Cell* 829–838 (1989)) and thus addition of cyclin to a reaction containing cdc2 as the substrate would probably result in alteration of the target substrate and confuse the interpretation of any observed effect. For this reason a substrate much used in tyrosine phosphatase studies, namely reduced, carboxamidomethylated and maleylated lysozyme (RCML, Tonks, N. K. et al., *J. Biol. Chem.* 263:6731–6737 (1988)) was used. This substrate was labelled on tyrosine residues with $^{32}p$ and kindly provided by N. Tonks.

Figure 4A:
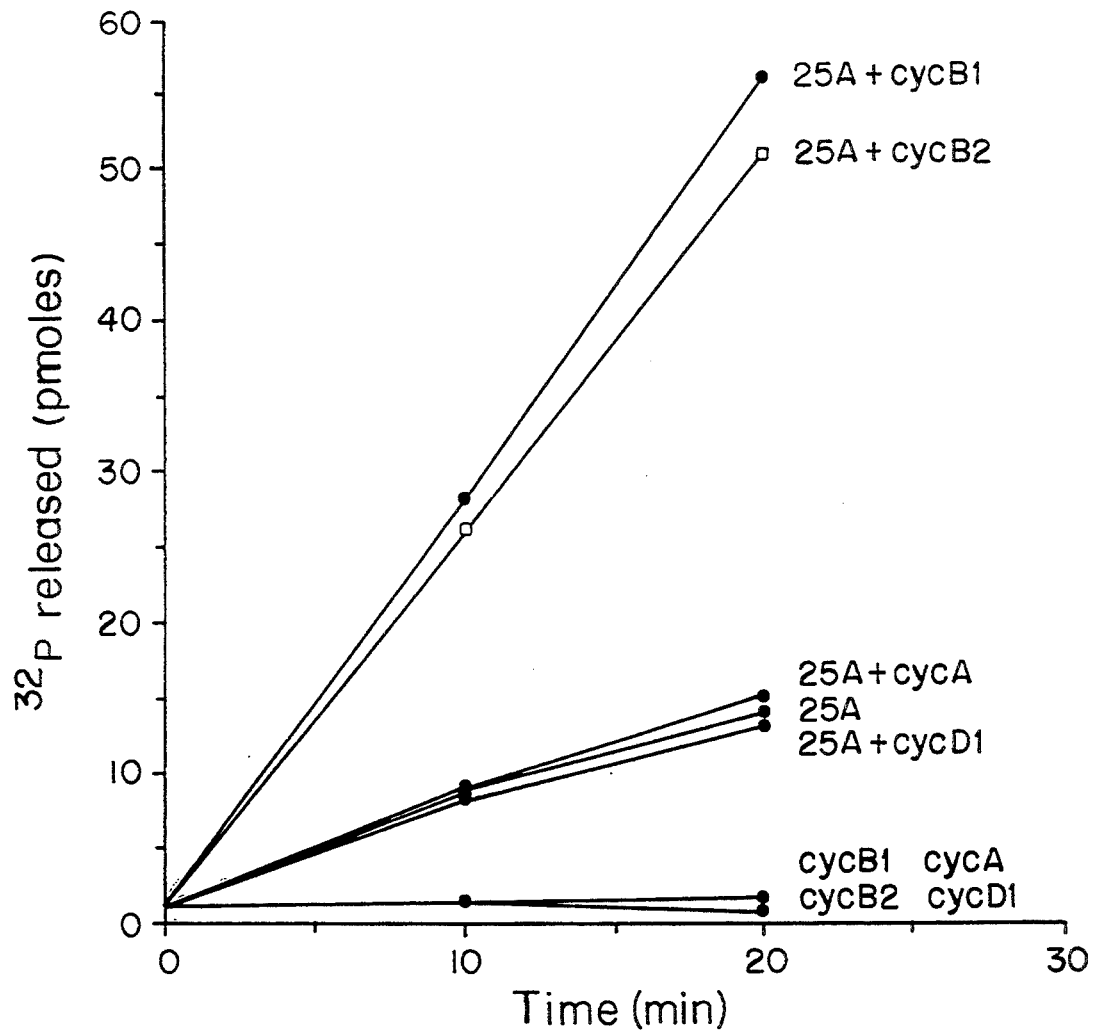
FIG. 4 shows activation of cdc25 A phosphatase by mitotic cyclins. Human GST-cdc25 A fusion protein was used to assay release of $^{32}$P from tyrosine phosphorylated, reduced carboxamidomethylated, maleylated lyzosyme (RCML, see experimental procedures) (A), cdc2-derived peptide (B) or PNPP hydrolysis (C). Cyclin fusion proteins were also purified in essentially the same way (see experimental procedures). In each case, 10 pmoles of cyclin and cdc25 protein were used in A and B, 50 pmoles in C. $A_{410}$ indicates adsorbance at 410 nm.
Figure 5:
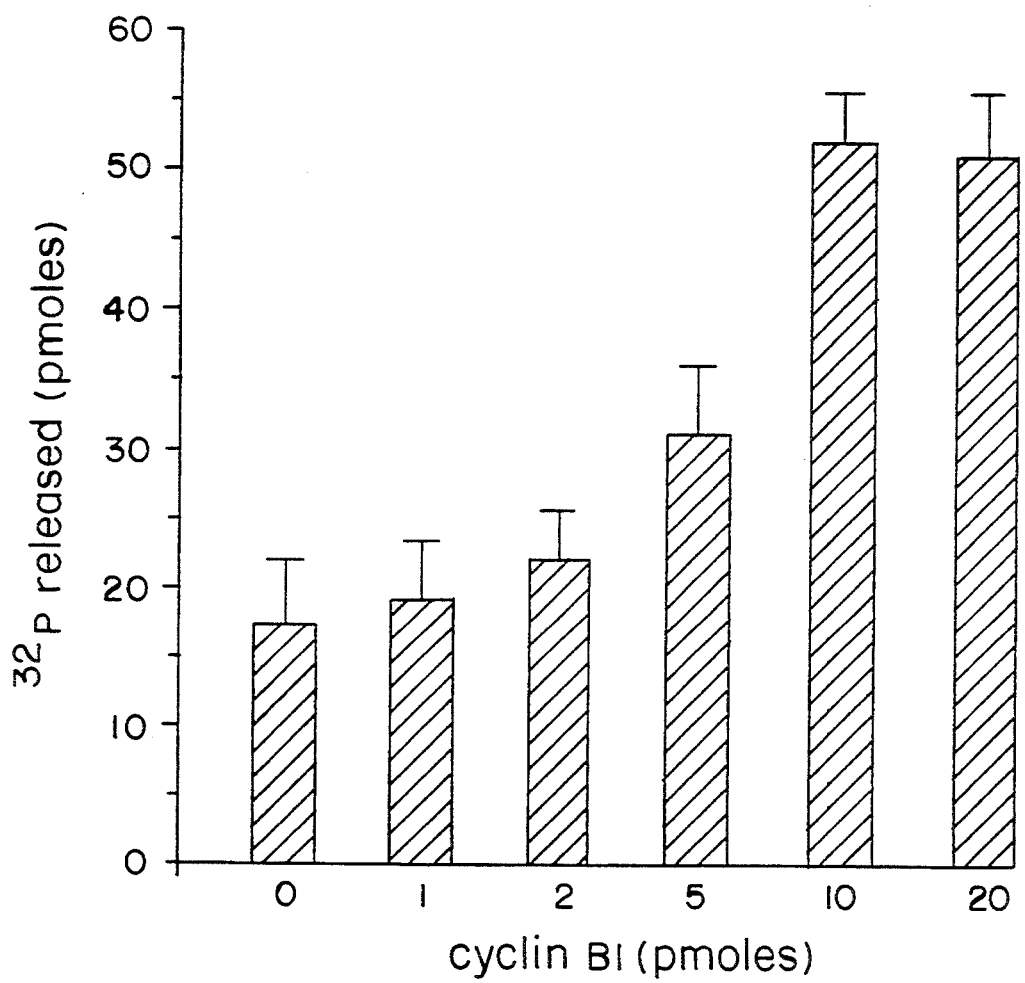
FIG. 5 is a graphic representation of dose-dependent activation of the cdc25 A by cyclin B1. The assay was performed as in [FIG. 7A], either without cyclin or with the addition of 1, 2, 5, 10 or 20 pmoles of the cyclin B1. The reaction was performed for 20 min and terminates by the addition of the trichloroacetic acid (TCA). Bars indicate the standard error in three experiments.

Cyclins purified from bacteria displayed no phosphatase activity against RCML (FIG. 4A). However, cdc25 A had an endogenous tyrosine phosphatase activity (FIG. 4A, see experimental procedures), that is linear for at least 30 minutes (not shown). If it is assumed that all the bacterial cdc25 protein is equally catalytically active, we can calculate that each molecule of cdc25 releases approximately one phosphate per 10 minutes. Addition of cyclin A or D to the reaction mixture had neither stimulatory nor inhibitory effect on the endogenous activity of cdc25 A (FIG. 4A), at any concentration tested. However, similar addition of either cyclin B1 or B2 had an approximately four-fold stimulatory effect (FIG. 4A). In the preceding experiments, 10 pmoles of each protein were used in the reaction mixture. The dependency of the activation of cdc25 on the amount of added cyclin B1 was also investigated. Activation was observed to plateau at 10 pmoles of added cyclin B1 and no further effect was detected at higher concentrations (FIG. 5). Thus, under these experimental conditions, maximal activation of cdc25 is achieved by stoichiometric addition of cyclin B.

Figure 4B:
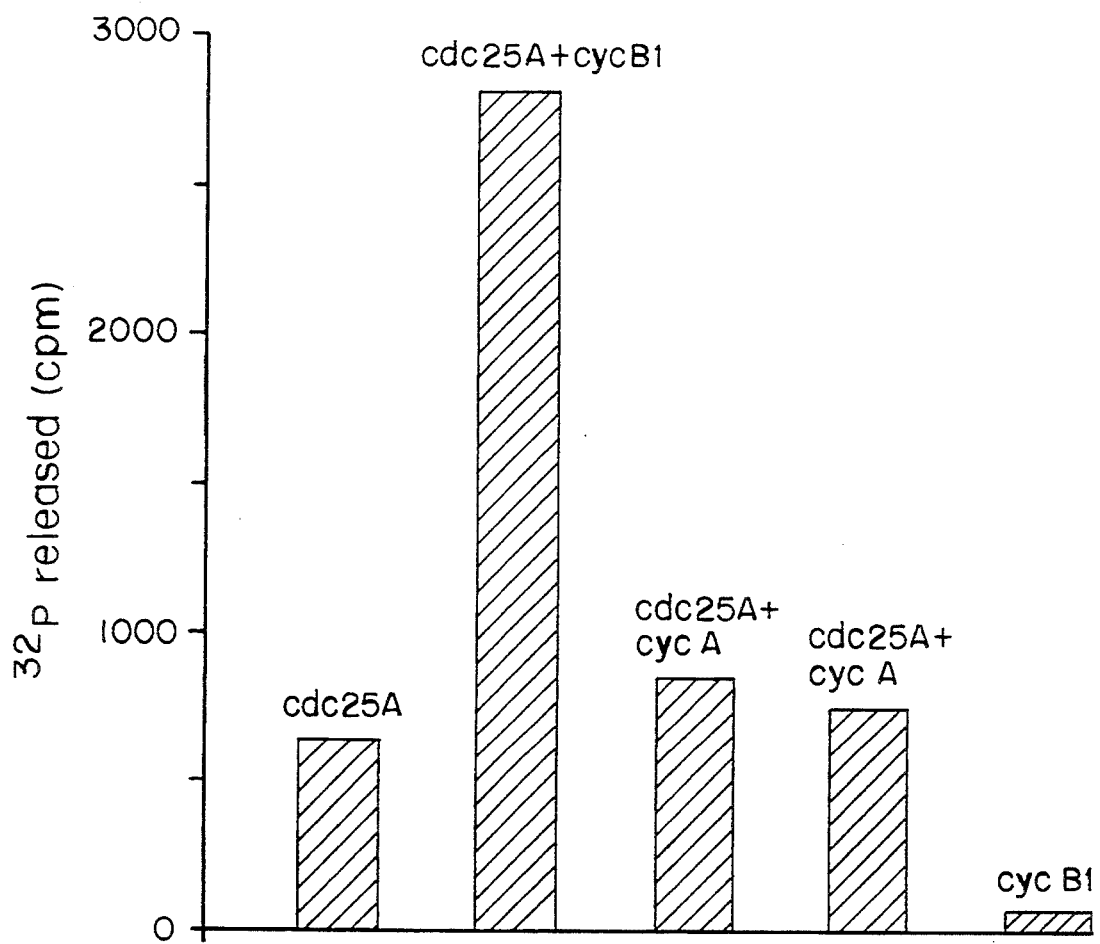
Figure 4C:
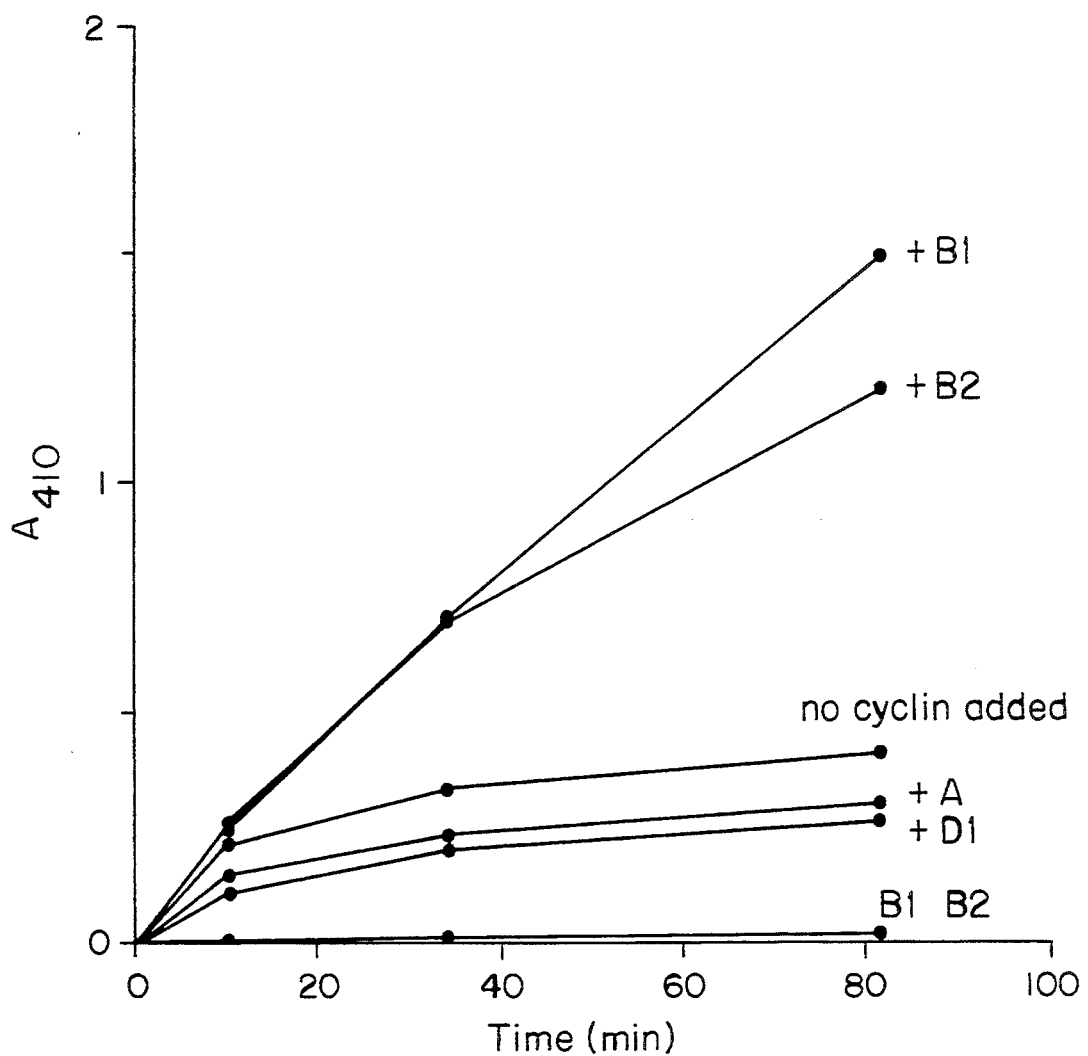

Whether the same stimulatory effect of B-type cyclins on the catalytic activity of cdc25 A could be detected was tested using other substrates: p-nitrophenylphosphate (PNPP), another frequently used PTPase substrate (Tonks, N. K. et al., *J. Biol. Chem.* 263:6731–6737 (1988); Guan, K. et al., *Nature* 350:359–362 (1991); Dunphy, W. G. and A. Kumagai, *Cell* 67189–196 (1991)) and the 18-mer peptide corresponding to the N-terminal region of the cdc2 protein surrounding Tyr15 (see Experimental Procedures). In the first case, the catalytic rate for cdc25 A was activated four to five-fold, specifically in the presence of cyclin B (FIG. 4C). When the 18-mer peptide was used similar levels of cdc25 A activation by B cyclins were detected (FIG. 4B).

EXAMPLE 5

Cyclin B1/cdc2 Interacts with cdc25 A

To investigate the possibility of stable interaction between cdc25 and cyclin, predicted from the data on the activation of the cdc25 A phosphatase activity and additional work described in Examples  , immunoprecipitates with the cdc25 A anti-peptide antibody described above were prepared. In this case, immunoprecipitations were performed under conditions favorable for retention of cdc25 protein complexes (see Experimental procedures). Immunoprecipitates were probed with anti-cyclin B1 antibody or G6 (prepared against C-terminal peptide of the cdc2, Draetta, G. et al., *Nature* 336:738–744 (1988)). Clear signals were detected in both cases, indicating that human cdc25 protein is present in a complex with both cyclin B1 and cdc2 (FIG. 6).

EXAMPLE 6

Figure 7:
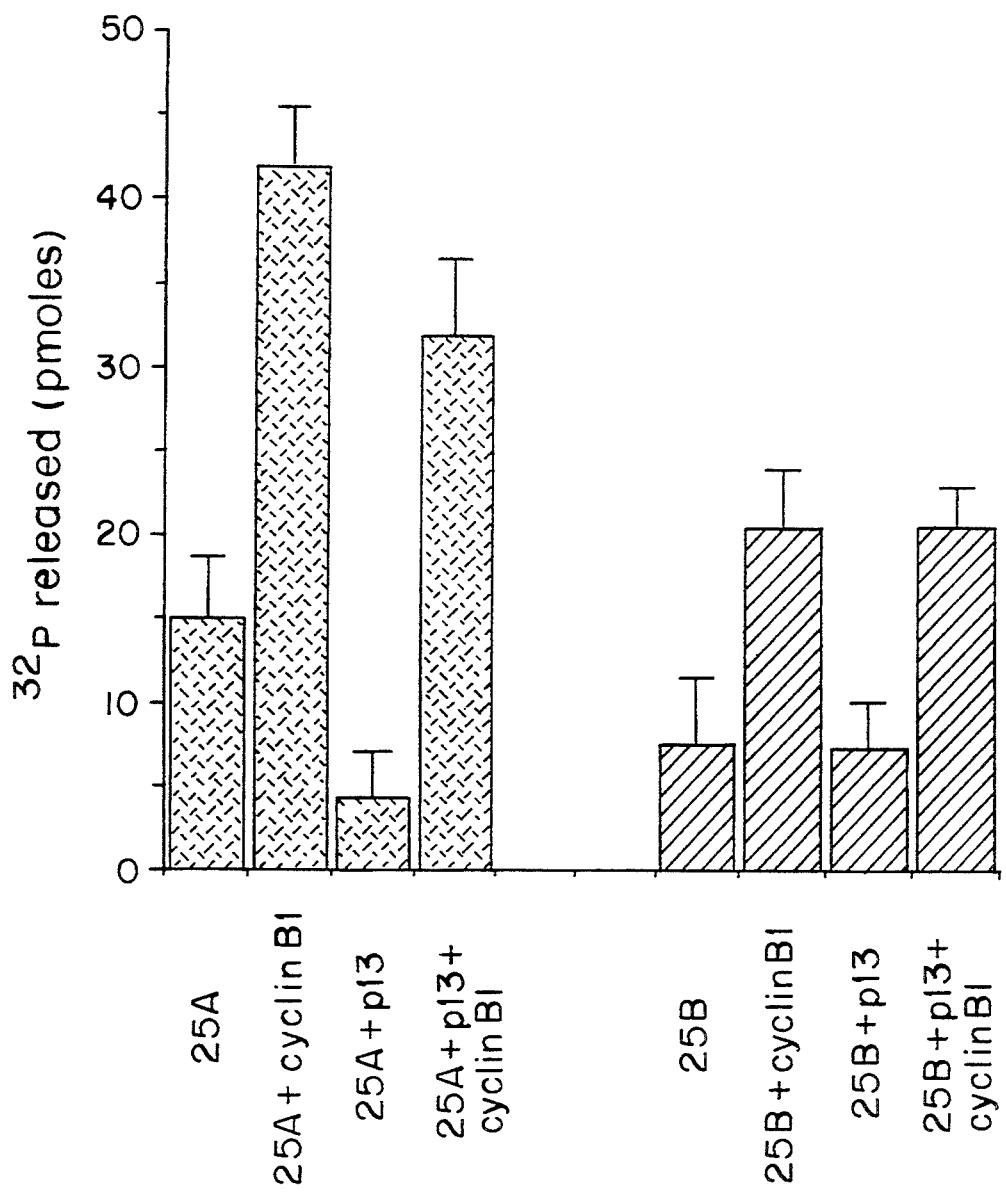
FIG. 7 shows inhibition of cdc25 phosphatase activity by p13 (Suc1). The phosphatase assay was performed as in FIG. 7 with the addition of p13 at a final concentration of 25 mM, with or without 0.5 mM (10 pmoles) cyclin B1. In the left panel, cdc25 A (10 pmoles) and right panel, cdc25 B (10 pmoles) was used. Bars indicate the standard error in three independent experiments.

Selective Inhibition by p13 p13 is an essential subunit of the cdc2 protein kinase. An excess of p13 can, however, inhibit activation of pre-MPF (see introduction and discussion). We tested whether p13 could directly influence the phosphatase activity of either of the human cdc25 proteins. In the case of cdc25 A, a 2–3-fold inhibition of the endogenous phosphatase activity was observed by adding p13 at 25 mM (FIG. 7). This concentration is far higher than that of the cdc25 protein itself (0.3 mM) but is similar to that required to prevent pre-MPF activation in vivo or in vitro (Dunphy, W. et al., *Cell* 54:423–431 (1988); Dunphy, W. and J. W. Newport, *Cell* 58:181–431 (1989)). Addition of cyclin B1 is equimolar concentration to the phosphatase, was able to substantially negate the inhibitory effect of p13, causing an eight-fold activation (FIG. 7). The behavior of cdc25 B was quite different. In preliminary experiments, we found that the pH optimum for this phosphatase is 8.8 (as opposed to 8.0 for cdc25 A). At this pH, cyclin B1 could activate cdc25 B to a similar degree to cdc25 A. However, we observed no effect of p13 on the activity of cdc25 B, either in the presence or absence of cyclin B (FIG. 7).

EXPERIMENTAL PROCEDURES

The following experimental procedures were used in the work described in Examples 7–13.

Oocyte and Extract Preparation

Xenopus laevis prophase oocytes were prepared as described (Jessus, C. et al., *FEBS Letters* 266:4–8 (1987)) and were induced to mature by 1 mM progesterone. Xenopus metaphase unfertilized eggs were activated in 1 mM HEPES pH=7.4, 8.8 mM NAGl, 10 mM CaCl$_2$, 33 mM Ca(NO$_3$)$_2$, 0.1 mM KCl, 82 mM MgSO$_4$, 5 mg/ml Ca$^{2+}$-ionophore A-23187 (Sigma) and 100 mg/ml cycloheximide (Sigma). After 40 min, eggs were either homogenized and referred as "activated eggs" or washed, transferred to incubation buffer (Jessus., C. et al., *FEBS Letters* 266:4–8 (1987)) and homogenized at different times. to prepare extracts, oocytes were washed extensively in extraction buffer EB (Cyert, M. S. and M. W. Kirschner, *Cell* 53:185–195 (1988)) 80 mM b-glycerophosphate pH=7.3, 20 mM EGTA, 15 mM MgCl$_2$1 mM DTT), then lysed at 4° C. in one volume of EB with protease inhibitors (25 mg/ml leupeptin, 25 mg/ml aprotinin, 1 mM benzamidine, 10 mg/ml pepstatin, 10 mg/ml soybean trypsin inhibitor and 1 mM PMSF) and centrifuged for 1 h at 100,000×g at 4° C. The supernatant was then filtered through 0.22 mm Millex-GV filters (Millipore) before use.

Preparation and Use of p13-Seharose Beads

P13 was purified and conjugated to sepharose as previously described (Brizuela, L. et al., *EMBO J.* 6:3507–3514 (1987)). After preincubation for 1 h with Sepharose CL-6B and centrifugation to remove non-specific binding, 100 ml of oocyte extracts were incubated for 90 min at 4° C. under constant rotation with 400 ml of EB plus protease inhibitors and 20 ml of p13-Sepharose beads. p13-Sepharose beads were further washed three times in EB, then either resuspended in 80 ml of Laemmli sample buffer (Laemmli, U. K., *Nature* 227:680–685 (1970)) and boiled for 3 min or immediately used for histone H1 kinase assay.

Preparation of 0–33% Ammonium Sulfate Extracts

Prophase oocytes were rinsed extensively in EB, then lysed in one volume of EB with protease inhibitors at 4° C. and centrifuged at 41,000 rpm for 90 min at 4° C. in Ti.41 rotor (Beckman). The supernatant was removed and filtered through 0.22 mm Millex-GV filters (Millipore). Ammonium sulfate fractionation was carried out by addition of 0.5 volume of a saturated solution of ammonium sulfate in EB to the extract, incubation on ice for 45 min, centrifugation at 41,000 rpm for 90 min at 4° C. and resuspension of the pellet in one-tenth of the initial volume (to a final protein concentration of 15 mg/ml, as determined with the BioRad protein assay kit with q-globulin as the standard). This extract (termed 0–33% fraction) was dialyzed for 2 h at 4° C. against EB in the presence of protease inhibitors and stored at −70° C. until use. For activation, extracts were incubated at room temperature with 1 mM ATP, 50 mg/ml creatine phosphokinase (Boehringer Mannheim) and 10 mM creatine phosphate (Boehringer Mannheim).

Antibodies

Fission yeast cdc25 protein was produced in *Escherischia coli* expressing the full-length protein (Ducommun, B. et al., *Biochem. Biophys. Res. Comm.* 167:301–309 (1990)). Bacterially produced cdc25 protein was purified and solubilized as described by Kumagai and Dunphy (Kumagai, A. and W. G. Dunphy, *Cell* 64:903–914 (1991)). To purify B1 anti-cdc25 serum (Ducommun, B. et al., *Biochem. Bio. Res. Comm.* 167:301–309 (1990)), bacterially expressed cdc25 protein was subjected to SDS-polyacrylamide electrophoresis and extracted by incubation of the excised gel pieces in PBS (phosphate saline buffer)-0.1% SDS-0.5% b-mercaptoethanol at 37° C. for 16 h. After centrifugation, the protein was concentrated on Centricoh-10 microconcentrators (Amicon) and incubated with nitrocellulose (0.45 mm; Schleicher and Schuell) for 3 h at room temperature. After three ten minute washes in PBS-0.1% SDS, filters were blocked for 4 h at room temperature with PBS containing 1.5% BSA (bovine serum albumine, Boehringer Mannheim) and 0.5% Tween-20. After three ten minute washes in PBS-0.1% SDS, filters were incubated at room temperature for 16 h with B1 anti-cdc25 serum (Ducommun, B. et al., *Biochem. Biophys. Res. Comm.* 167:301–309 (1990)), diluted four times in PBS-1.5% BSA. Filters were then washed three times for 10 min with PBS-0.1% Tween-20 and once for 10 min with PBS. Purified anti-cdc25 antibody was eluted with 1 ml of 100 mM glycine pH-2.5, and 200 ml of 1M TRIS pH=8.0 was added after 1 min. After addition of 300 ml of PBS-10% BSA-0.5% NAN$_3$, the purified antibody was stored at 4° C. until use. For some control experiments, the purified antibody was preadsorbed overnight at 4° C. with 10 m/ml purified bacterially expressed yeast cdc25 protein before Western blotting.

Anti-B2 cyclin antibody is a gift from J. Gautier (rabbit polyclonal purified antibody directed against Xenopus cyclin B2; Gautier, J. et al., *Cell* 60:487–494 (1990); Gautier, J. and J. Maller, *EMBO J.* 10:177–182 (1991)). Anti-cdc2 antibody is a rabbit polyclonal purified antibody directed against thr full-length Schizosaccharomyces pombe cdc2 (Draetta, G. et al., *Cell* 50:319–325 (1987)). Anti-phosphotyrosine antibody is a mouse IgG monoclonal antibody (Ab-1, Oncogene Science). The sensitivity of this anti-phosphotyrosine antibody ought to be sufficient to allow the detection of phosphotyrosine in the cdc25-associated cdc2, since a comparable amount of prophase cdc2 is easily recognized. Therefore, the absence of signal observed in metaphase cdc2 bound to cdc25 (FIG. 5A, lane 5) suggests that this population of cdc2 is not phosphorylated on tyrosine.

Immunoprecipitation and Western Blot Analysis 100 ml of oocyte extracts in EB were mixed with 400 ml of Eb and incubated for 1 h at 4° C. with 30 ml of protein A-agarose beads (Pierce). Anti-cdc25 antibody (dilution 1:100), anti-cyclin B2 antibody (dilution 1:50) or anti-cdc2 antibody (dilution 1:500) were then added to the supernatant and after a 5 h incubation at 4° C., 30 ml of protein A-agarose beads were added. After an additional 1 h incubation at 4° C., the beads were either washed four times in EB and then eluted by boiling for 30 min in 80 ml Laemmli sample buffer (1970) or resuspended in kinase buffer (50 mM TRIS pH=7.4, 10 mM MgCl$_2$, 5 mM EGTA, 1 mM DTT) for a subsequent histone H1 kinase assay.

To elute Xenopus cdc25 protein from immunoprecipitates, immunocomplexes were resuspended in 250 ml of 100 mM glycine pH-2.5. After a 2 min stirring, 50 ml of 1M TRIS pH=8.0 was added. The supernatant was recovered, concentrated on Centricon-10 microconcentrators (Amicon) and bovine serum albumine was added to a final concentration of 0.1%.

Electrophoresis and Western blot analysis with anti-cdc25 antibody (dilution 1:500), anti-cyclin B2 antibody (dilution 1:100) or anti-cdc2 antibody (dilution 1:000) were performed as previously described (Booher, R. N. et al., *Cell* 58:584–497 (1989)). By scanning immunoblots of initial extracts before anti-cdc25 immunoprecipitation, extracts after anti-cdc25 immunoprecipitation and anti-cdc25 immunoprecipitates (FujiX Bas 2000 Image Analyzer), we estimated that 70% of the full cellular amount of cdc25 is immunoprecipitated by the anti-cdc25 antibody. In a parallel way, we quantified the amount of p72 associated with cdc2 or cyclin B2 in immunoprecipitates by Image Analyzer (FujiX Bas 2000), by using anti-cdc25 immunoblots of crude extracts as a reference of the full cellular amount of cdc25. 20% of the total cellular amount of cdc25 was found either in anti-cdc2 immunoprecipitates or in anti-cyclin B2 immunoprecipitates. To quantify the amount of cdc2 or cyclin B2 associated with cdc25, equal amounts of oocyte extracts (from 10 oocytes, equivalent to 200 mg of proteins) were either precipitated on p13-Sepharose or immunoprecipitated with anti-cdc25 antibody. p13-Sepharose beads completely clear the extract of cdc2 and cyclin B2 as ascertained by Western blotting (data not shown) and, therefore, p13-precipitate represents the full cellular amount of cdc2 and cyclin B2. On the other hand, the anti-cdc25 immunoprecipitate contains only the cdc2 and the cyclin B2 that are associated with p72. Both p13-precipitates and anti-cdc25 immunoprecipitates (each the equivalent of 10 oocytes) were loaded on the same electrophoresis gel and blotted with the anti-cdc2 antibody or the anti-cyclin B2 antibody. The relative amounts of cdc2 and cyclin B2 detected in both extracts were determined by Phosphor-Imager (Molecular Dynamics) or Image Analyzer (FujiX Bas 2000). The amount of cdc2 present in p13-Sepharose precipitate is 20-fold higher than that detected in the anti-cdc25 immunoprecipitate. Thus, 5% of the total cdc2 is associated with p72. The amount of cyclin B2 present in p13-Sepharose precipitates is 6-fold higher than that detected in the anti-cdc25 immunoprecipitate. Thus, 17% of the total cyclin B2 is associated with p72.

Histone H1 Kinase Assay p13-precipitates or immunocomplexes were washed three times in kinase buffer and then resuspended in 50 ml of kinase buffer containing 0.2 mg/ml histone H1 (Boehringer Mannheim), 50 mM ATP and 1 mCi[q$^{32}$P]ATP (PB.10168, Amersham). After a 30 min incubation at 30° C., the reactions were terminated by the addition of 30 ml Laemmli sample buffer (Laemmli, U. K., *Nature* 227:680–685 (1970)). Samples were electrophoresed on a 12% polyacrylamide gel. After staining with coomassie blue and autoradiography, P incorporation into histone H1 was quantified by scintillation counting of excised gel pieces.

Protein samples from the 0–33% fraction (in a volume of 10 ml of EB) were mixed on ice with 40 ml of kinase buffer containing 0.2 mg/ml histone H1, 25 mM ATP, 2 m Ci[q$^{32}$P]ATP and 10 mM cAMP dependent protein kinase inhibitor peptide (P3294, Sigma). After incubation for 10 min at 30° C., samples were treated as previously described.

EXAMPLE 7 cdc25 Protein in Xenopus Oocytes

An anti-cdc25 serum directed against fission yeast cdc25 was used to determine whether a cdc25 protein is present in Xenopus oocytes. This serum, previously referred to as B1 (Ducommun, B. et al., *Biochem. Biophys. Res. Comm.* 167:301–309 (1990)), was affinity purified as described in the Experimental Procedures. It recognizes the full-length yeast cdc25 product expressed in *E. coli* but no signal is detectable in an *E. coli* lysate before transcriptional cdc25 induction of cdc25 (Ducommun, B. et al., *Biochem. Biophys. Res. Comm.* 167:301–309 (1990)).

Figures 9A, 9B, 9C:

Extracts were prepared from the following cells: meiotic prophase-blocked oocytes, meiotic metaphase unfertilized eggs, eggs activated in the presence of cycloheximide, that therefore lack cyclin and are blocked in an interphase state (Murray, A. W. and Kirschner, M. *Nature* 339:275–280 (1989)); see also FIG. 12A, lan3 3 and FIG. 9C, lane 4) and eggs after 120 min of activation (after completion of the first MPF cycle, also see FIG. 13 for the histone H1 kinase level at this stage). These extracts were probed with the affinity-purified serum in an immunoblot. A 72 kD polypeptide was detected in each lane (FIG. 9A, lanes 1–4). No signal was detected using the same procedure but with preimmune serum (not shown), or with the purified antibody preadsorbed with soluble bacterially-expressed yeast cdc25 protein (FIG. 9A, lanes 5–8). Furthermore, two other purified polyclonal antibodies directed against the yeast cdc25 protein were able to recognize the same 72 kD protein from Xenopus extracts. (Ducommun, B. et al., *Biochem. Biophys. Res.* 167:301–309 (1990)).

To test whether the 72 kD species might be immunoprecipitated by the anti-cdc25 antibody, extracts from prophase oocytes, metaphase unfertilized eggs and interphase eggs activated in the presence of cycloheximide were precipitated with the purified anti-cdc25 antibody and probed with the same purified serum in immunoblots. Again, a protein of 72 kD was specifically detected by the cdc25 antibody (FIG. 9B, lanes 1 to 3). In contrast, no signal was detected when the same procedure was used in the absence of Xenopus extract (FIG. 9B, lane 4), formally demonstrating that the 72 kD protein observed in the immunoprecipitates is not due to the presence of cdc25 protein in the antibody preparation (a contamination that could occur during immuno-affinity purification of the antibody).

To obtain soluble 72 kD polypeptide, proteins were eluted from anti-cdc25 immunoprecipitates at low pH (see Experimental Procedures) and the amount of 72 kD protein was determined by immunoblotting with the cdc25 antibody. Again, the same level of 72 kD protein was found in prophase oocytes, metaphase unfertilized eggs, interphase-blocked activated eggs and eggs after the completion of the first MPF cycle (FIG. 9B, lanes 5–8).

EXAMPLE 8

Demonstration That cdc25 Activates the M-phase Kinase

Human and Drosophilia cdc25 proteins are able to trigger activation of cdc2/cyclin B in vitro (Kumagai, A. and W. G. Dunphy, *Cell* 64:903–914 (1991); Strausfeld, U. et al., *Nature* 351:242–245 (1991)) by dephosphorylating cdc2 (Dunphy, W. G. and A. Kumagai, *Cell* 67:189–196 (1991); Gautier, J. et al., *Cell* 67:197–211 (1991)). As a further test that the anti-cdc25 antibody recognized Xenopus cdc25, we investigated whether the 72 kD protein eluted from immunocomplexes could stimulate inactive cdc2. To prepare inactive enzyme from prophase oocytes we used p13-Sepharose beads. Xenopus cdc2 protein binds strongly and quantitatively to fission yeast p13 (Dunphy, W. et al., *Cell* 54:423–431 (1988)). The p13-Sepharose bound cyclin B/cdc2 complex from prophase oocytes has a low histone H1 kinase activity (FIG. 9C, lane 1). Protein eluted from anti-cdc25 immunoprecipitates of either prophase oocytes or metaphase unfertilized eggs (as illustrated in FIG. 9B, lanes 5 and 6) was added to inactive prophase p13-bound cdc2. After a 30 min preincubation in the presence of cdc25-immunocomplex eluates, the p13-precipitate was extensively washed before assaying for histone HI kinase activity. Both prophase and metaphase cdc25 stimulated histone H1 kinase activity 12-fold (FIG. 9C, lanes 2 and 3). We have eliminated the possibility that some of the histone H1 kinase activity that is present in the anti-cdc25 immunocomplexes (see below) might be responsible for this increase of kinase activity. First, the p13-Sepharose precipitate was extensively washed after preincubation with the immunoeluted material and before assay of kinase activity. Second, the histone H1 kinase activity found associated with the eluted metaphase proteins is insufficient to account for the observed 12-fold stimulation of the p13-bound enzyme (approximately 500 units of final activity, FIG. 9C, lane 3). Third, the prophase immuno-eluted material is also able to activate cdc2, although it does not contain any kinase activity (see below, FIG. 11C, lane 1). We, therefore, conclude that an active Xenopus cdc25 protein was precipitated by the affinity-purified anti-cdc25 antibody from both prophase oocytes and metaphase eggs. It is surprising that active p72 could be extracted from Xenopus oocytes in which cdc2/cyclin B is inactive and tyrosine phosphorylated. This issue is addressed below (see discussion).

We further tested whether p72 from either prophase oocytes or metaphase unfertilized eggs could affect the activity of either fully activated cdc2/cyclin from metaphase unfertilized eggs or cdc2 that is inactive in the absence of cyclin (material extracted from eggs activated in the presence of cycloheximide). In neither case did p72 have any effect on the histone H1 kinase activity of cdc2 (FIG. 9C, lanes 4–9). The 135 units of activity found in lane 6 (FIG. 9C) is probably due to the basal activity of cdc2 from activated eggs (66 units, FIG. 9C, lane 4) combined with the kinase activity associated with metaphase cdc25 and therefore does not represent a real stimulation of cdc2. We conclude that p72 only acts on the tyrosine phosphorylated enzyme.

EXAMPLE 9

Demonstration That Activation of pre-MPF Requires cdc25

Xenopus prophase oocytes contain an inactive form of MPF that can be activated by a post-translational mechanism both in vivo (Wasserman, W. and Y. Masui, *Exp. Cell. Res.* 91:381–388 (1975); Gerhart, J. et al., *J. Cell Biol.* 98:1247–1255 (1984)) and in vitro (Cyert, M. S. and M. W. Kirschner, *Cell* 53:185–195 (1988); Dunphy, W. G. and J. W. Newport, *Cell* 58:181–191 (1989)). Addition of an ATP-regenerating system to a prophase oocyte extract (33% ammonium sulfate precipitated fraction) is sufficient to induce tyrosine dephosphorylation of cdc2 and stimulation of its latent activity (Cyert, M. S. and M. W. Kirschner, *Cell* 53:185–195 (1988); Dunphy, W. G. and J. W. Newport, *Cell* 58:181–191 (1989)). In order to determine if the endogenous p72 was required for this activation process, we explored the effect of adding anti-cdc25 antibody to the 0–33% ammonium sulfate fraction from prophase oocytes. Following the addition of an ATP-regenerating system to the extract, the histone H1 kinase was rapidly activated (FIG. 10). By contrast, a 15 min preincubation of the extract with anti-cdc25 antibody resulted in a prolonged inhibition of the activation process. Addition of the preimmune serum had no effect (FIG. 10). This result suggests that the endogenous p72 is required for histone H1 kinase activation and is inactivated after immunocomplexing with the antibody. We further found that bacterially-expressed cdc25 protein can overcome the inhibition caused by the anti-cdc25 antibody (FIG. 10), indicating that the antibody acts specifically on the endogenous cdc25 protein.

EXAMPLE 10

Demonstration of an Association Between cdc25 and cdc2 at M-phase

To further investigate the mechanism of cdc2 activation by cdc25, we tested the possibility that cdc25 might directly associate with the M-phase enzyme. Extracts of either prophase oocytes, metaphase unfertilized eggs or activated eggs were immunoprecipitated with an anti-cdc2 antibody and probed with the same anti-cdc2 antibody. As expected, a strong signal was obtained (FIG. 11A, lanes 1–3). Since the anti-cdc2 antibody recognizes a single 34 kD band (FIG. 11A), we assume that this antibody does not react with cdk2, a 32 kD cdc2-like protein encoded by the Xenopus Egl gene (Paris, J. et al., *Proc. Natl. Acad. Sci. USA* 88:1039–1043 (1991)). Similar anti-cdc2 immunoprecipitates were probed with the purified anti-cdc25 antibody A 72 kd band was observed in the metaphase unfertilized eggs, but not in the resting prophase oocytes or in the eggs activated in the presence of cycloheximide (FIG. 11B). In a control experiment in which the purified anti-cdc25 antibody was preadsorbed with bacterially expressed cdc25 protein before immunoblotting, no signal was detected. These results indicate that cdc25 stably associates with cdc2 at M-phase.

Figure 11D:

To further test the existence of an association between cdc2 and cdc25 we performed the converse experiment. Cdc25 was immunoprecipitated from prophase oocytes, metaphase unfertilized eggs and activated eggs using the purified anti-cdc25 antibody. An equal amount of cdc25 was precipitated in each case (FIG. 9B, lanes 1–3). We then probed the anti-cdc25 immunoprecipitates with the anti-cdc2 antibody. A 34 kD protein was detected in the metaphase unfertilized eggs, but not in the prophase oocytes or in the activated eggs (FIG. 11C). To confirm that the 34 kD protein detected in this experiment is indeed cdc2, prophase oocyte, metaphase unfertilized egg and activated egg extracts were first depleted of the cdc2/cyclin B complex by preincubation with p13-Sepharose and then immunoprecipitated with the purified anti-cdc25 antibody. Immunoblotting these immunocomplexes with anti-cdc2 antibody revealed complete depletion of the 24 kD protein (FIG. 11D). We therefore conclude that the 34 kD protein is cdc2. Moreover, cdc2, which is present at the same level in prophase oocytes, metaphase eggs and interphase eggs was not recognized in an immunoblot by the purified anti-cdc25 antibody (FIG. 11B), indicating that there is no cross-reactivity between cdc2 and the anti-cdc25 antibody. By quantifying the signal in immunoblots (see Experimental Procedures), we estimate that the amount of cdc2 present in anti-cdc25 immunoprecipitates represents approximately 5% of the total cellular cdc2 at metaphase and that the amount of cdc25 present in anti-cdc2 immunoprecipitates represents 20% of the cellular content of cdc25 (see Discussion).

EXAMPLE 11

Demonstration That Cyclin B is Associated with cdc2 and cdc25 at M-Rhase

Figure 12A:
Figure 12B:
Figure 12C:
Figure 12D:

Since the active cdc2 from M-phase is associated with cyclin (Brizuela, L. et al., *Proc. Natl. Acad. Sci. USA* 86:4362–4366 (1989); Draetta, G. et al., *Cell* 56:829–838 (1989); Gautier, J. et al., *Cell* 60:487–494 (1990)), we further investigated whether cyclin B is present in association with cdc2 and cdc25 at M-phase. Extracts of either prophase oocytes, metaphase unfertilized eggs or activated eggs were precipitated with p13-Sepharose and probed with an anti-cyclin B2 antibody. Cyclin B2 was present in both prophase oocytes and metaphase unfertilized eggs (FIG. 12A, lanes 1 and 2). As already noted (Gautier, J. and J. Maller, *EMBO J.* 10:177–182 (1991); Kobayashi, A. H. et al., *J. Cell Biol.* 114:755–765 (1991)), two immunoreactive bands of cyclin B2 are detectable (FIG. 12A), of which the upper band is a phosphorylated form appearing during meiotic maturation. In contrast, cyclin B2 was not detectable in eggs activated in the presence of cycloheximide (FIG. 12A, lane 3). The same extracts were immunoprecipitated with the anti-cyclin B2 antibody and then probed with the purified anti-cdc25 antibody. The 72 kD protein was detected in associated with cyclin B2 in the metaphase eggs but not in the prophase oocytes or in the interphase eggs (FIG. 12B). The converse experiment was then performed. The three types of cell extracts were immunoprecipitated with the purified anti-cdc25 antibody and probed with the anti-cyclin B2 antibody. Cyclin B2 was associated with cdc25 in metaphase unfertilized eggs, but not in resting prophase oocytes or activated eggs (FIG. 12C). The phosphorylated form of cyclin B2 (upper band) is predominantly associated with cdc25. As a control experiment, prophase oocyte, metaphase egg and activated egg extracts were first depleted of cdc2/cyclin B by incubation with p13-Sepharose and then immunoprecipitated with the anti-cdc25 antibody. No signal was detected after probing these extracts with the anti-cyclin B2 antibody (FIG. 12D), indicating that the 1 kD band previously detected (FIG. 12C, lane 2) was indeed cyclin. We therefore conclude that cdc25 binds to the cyclin B/cdc2 complex at metaphase. We estimate that the amount of cdc25 present in anti-cyclin B2 immunoprecipitates is the same as the proportion of cdc25 previously found in association with cdc2 (20% of the full cellular content of cdc25, see discussion). In contrast, we determined that cdc25-associated cyclin B2 represents 17% of the total population of cyclin B2, which is a higher percentage than the amount of cdc25-associated cdc2 (5%).

EXAMPLE 12 M-phase Kinase Associated with cdc25 is Active

At metaphase, cdc2 is predominantly tyrosine dephosphorylated and active as a histone H1 kinase. Since cdc2 is associated with cdc25 only at metaphase, we investigated the tyrosine phosphorylation state and the kinase activity of the complexed cdc2. By immunoblotting p13-Sepharose precipitates with an anti-phosphotyrosine antibody, we confirmed that cdc2 is heavily tyrosine phosphorylated in prophase oocytes and substantially dephosphorylated in metaphase unfertilized eggs (NB, different batches of metaphase eggs display a somewhat different degree of cdc2 tyrosine dephosphorylation) as previously demonstrated (Dunphy, W. G. and J. W. Newport, *Cell* 58:181–431 (1989); Jessus, C. et al., *FEBS Letters* 266:4–8 (1990). No tyrosine phosphorylation of cdc2 could be detected in eggs that are activated in the presence of cycloheximide and thus lack cyclin B. (See also Solomon, M. J. et al., *Cell* 63:1013–1024 (1991)). When anti-cdc25 immunocomplexes from prophase oocytes, metaphase unfertilized eggs or activated eggs were probed with the same anti-phosphotyrosine antibody, no phosphotyrosine-containing proteins were detected, despite the presence of abundant cdc2 in the immunocomplex from metaphase unfertilized eggs (FIG. 4C, lane 2). We were able to calculate (see Experimental Procedures) that if the cdc25-associated cdc2 were substantially tyrosine phosphorylated, a signal of sufficient strength would have developed in the immunoblot. This result suggests that the fraction of cdc2 associated with cdc25 in metaphase unfertilized eggs is likely to be active as a histone H1 kinase. This was found to be the case. The kinase activity in p13-Sepharose precipitates is very low in prophase oocytes, is increased 31-fold in metaphase unfertilized eggs and declines during activation in the presence of cycloheximide. Histone HI kinase activity was detected in anti-cdc25 immunoprecipitates from metaphase eggs. The activity detected in anti-cdc25 immunoprecipitates from prophase oocytes and activated eggs is comparable to the background levels (FIG. 5B, lanes 4 and 6), indicating that no cdc2 kinase is present in these extracts. By comparing the relative metaphase kinase activity in P-13 Sepharose precipitates and anti-cdc25 immunoprecipitates (approximately 20-fold different) we found that the specific activity of cdc2 is essentially identical.

EXAMPLE 13

Association Between cdc2/cyclin B and cdc25 is Periodic

The abundance of the Xenopus cdc25 protein appears not to vary during meiotic maturation or in the first embryonic cycle (FIG. 9A). However, the protein was only found in association with cdc2 and cyclin B in metaphase unfertilized eggs. To investigate this more closely, metaphase unfertilized eggs were parthenogenetically activated in the presence of $CA^{2+}$ ionophore and calcium and histone H1 kinase activity was assessed in p13-Sepharose precipitates during the first 150 min. The histone H1 kinase activity disappeared about 20 min after activation, reappeared between 60 and 90 min, at time of the first cleavage, declined again and finally peaked at time of the second mitotic cleavage (FIG. 13). Samples taken from the same cell extracts were immunoprecipitated with anti-cdc25 antibody and immunoblotted with anti-cdc2 serum to estimate the extent of association. The periodic interval of the association between cdc2/cyclin B complex and cdc25 was identical to the periodicity of the p13-bound enzyme activity (FIG. 13). However, a slight phase shift was noted. The association peaked slightly ahead of the overall histone H1 kinase. In repeated experiments (not shown), the pattern of association was always the same. However, in some cases the phase shift between the histone HI kinase activity and the association between cdc2/cyclin B and cdc25 was less obvious.

Equivalents

Those skilled in the art will recognize, or be able to ascertain using not more than routine experimentation, many equivalents to the specific embodiments of the invention described herein. Such equivalents are intended to be encompassed by the following claims.

We claim:

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 2419 base pairs
( B ) TYPE: nucleic acid (C) STRANDEDNESS: double
(D) TOPOLOGY: linear (ii) MOLECULE TYPE: DNA (genomic)
(A) NAME/KEY: CDS
(B) LOCATION: 460..2031

(xi) SEQUENCE DESCRIPTION: SEQ ID No:1:

| | | | | |
|---|---|---|---|---|
| CGAAAGGCCG GCCTTGGCTG CGACAGCCTG GGTAAGAGGT GTAGGTCGGC TTGGTTTTCT | | | | 60 |
| GCTACCCGGA GCTGGGCAAG CGGGTTGGGA GAACAGCGAA GACAGCGTGA GCCTGGGCCG | | | | 120 |
| TTGCCTCGAG GCTCTCGCCC GGCTTCTCTT GCCGACCCGC CACGTTTGTT TGGATTTAAT | | | | 180 |
| CTTACAGCTG GTTGCCGGCG CCCGCCCGCC CGCTGGCCTC GCGGTGTGAG AGGGAAGCAC | | | | 240 |
| CCGTGCCTGT GGCTGGTGGC TGGCGCCTGG AGGGTCCGCA CACCCGCCCG GCCGCGCCGC | | | | 300 |
| TTTGCCCGCG GCAGCCGCGT CCCTGAACCG CGGAGTCGTG TTTGTGTTTG ACCCGCGGGC | | | | 360 |
| GCCGGTGGCG CGCGGCCGAG GCCGGTGTCG GCGGGGCGGG GCGGTCGCGG CGGAGGCAGA | | | | 420 |
| GGAAGAGGGA GCGGGAGCTC TGCGAGGCCG GGCGCCGCC ATG GAA CTG GGC CCG | | | | 474 |
| | | | Met Glu Leu Gly Pro | |
| | | | 1 5 | |

```
AGC CCC GCA CCG CGC CGC CTG CTC TTC GCC TGC AGC CCC CCT CCC GCG    522
Ser Pro Ala Pro Arg Arg Leu Leu Phe Ala Cys Ser Pro Pro Pro Ala
             10              15                  20

TCG CAG CCC GTC GTG AAG GCG CTA TTT GGC GCT TCA GCC GCC GGG GGA    570
Ser Gln Pro Val Val Lys Ala Leu Phe Gly Ala Ser Ala Ala Gly Gly
         25              30                  35

CTG TCG CCT GTC ACC AAC CTG ACC GTC ACT ATG GAC CAG CTG CAG GGT    618
Leu Ser Pro Val Thr Asn Leu Thr Val Thr Met Asp Gln Leu Gln Gly
         40              45              50

CTG GGC AGT GAT TAT GAG CAA CCA CTG GAG GTG AAG AAC AAC AGT AAT    666
Leu Gly Ser Asp Tyr Glu Gln Pro Leu Glu Val Lys Asn Asn Ser Asn
     55              60              65

CTG CAG AGA ATG GGC TCC TCC GAG TCA ACA GAT TCA GGT TTC TGT CTA    714
Leu Gln Arg Met Gly Ser Ser Glu Ser Thr Asp Ser Gly Phe Cys Leu
 70              75              80              85

GAT TCT CCT GGG CCA TTG GAC AGT AAA GAA AAC CTT GAA AAT CCT ATG    762
Asp Ser Pro Gly Pro Leu Asp Ser Lys Glu Asn Leu Glu Asn Pro Met
             90              95              100

AGA AGA ATA CAT TCC CTA CCT CAA AAG CTG TTG GGA TGT AGT CCA GCT    810
Arg Arg Ile His Ser Leu Pro Gln Lys Leu Leu Gly Cys Ser Pro Ala
             105             110                 115

CTG AAG AGG AGC CAT TCT GAT TCT CTT GAC CAT GAC ATC TTT CAG CTC    858
Leu Lys Arg Ser His Ser Asp Ser Leu Asp His Asp Ile Phe Gln Leu
         120             125                 130

ATC GAC CCA GAT GAG AAC AAG GAA AAT GAA GCC TTT GAG TTT AAG AAG    906
Ile Asp Pro Asp Glu Asn Lys Glu Asn Glu Ala Phe Glu Phe Lys Lys
 135             140                 145

CCA GTA AGA CCT GTA TCT CGT GGC TGC CTG CAC TCT CAT GGA CTC CAG    954
Pro Val Arg Pro Val Ser Arg Gly Cys Leu His Ser His Gly Leu Gln
150             155                 160                 165

GAG GGT AAA GAT CTC TTC ACA CAG AGG CAG AAC TCT GCC CAG CTC GGA    1002
Glu Gly Lys Asp Leu Phe Thr Gln Arg Gln Asn Ser Ala Gln Leu Gly
         170             175                 180

ATG CTT TCC TCA AAT GAA AGA GAT AGC AGT GAA CCA GGG AAT TTC ATT    1050
Met Leu Ser Ser Asn Glu Arg Asp Ser Ser Glu Pro Gly Asn Phe Ile
             185                 190                 195

CCT CTT TTT ACA CCC CAG TCA CCT GTG ACA GCC ACT TTG TCT GAT GAG    1098
Pro Leu Phe Thr Pro Gln Ser Pro Val Thr Ala Thr Leu Ser Asp Glu
         200                 205                 210

GAT GAT GGC TTC GTG GAC CTT CTC GAT GGA GAG AAT CTG AAG AAT GAG    1146
Asp Asp Gly Phe Val Asp Leu Leu Asp Gly Glu Asn Leu Lys Asn Glu
 215                 220                 225
```

| | | | | | | | | | | | | | | | | |
|---|---|---|---|---|---|---|---|---|---|---|---|---|---|---|---|---|
| GAG | GAG | ACC | CCC | TCG | TGC | ATG | GCA | AGC | CTC | TGG | ACA | GCT | CCT | CTC | GTC | 1194 |
| Glu | Glu | Thr | Pro | Ser | Cys | Met | Ala | Ser | Leu | Trp | Thr | Ala | Pro | Leu | Val | |
| 230 | | | | 235 | | | | | 240 | | | | | | 245 | |
| ATG | AGA | ACT | ACA | AAC | CTT | GAC | AAC | CGA | TGC | AAG | CTG | TTT | GAC | TCC | CCT | 1242 |
| Met | Arg | Thr | Thr | Asn | Leu | Asp | Asn | Arg | Cys | Lys | Leu | Phe | Asp | Ser | Pro | |
| | | | | 250 | | | | 255 | | | | | | 260 | | |
| TCC | CTG | TGT | AGC | TCC | AGC | ACT | CGG | TCA | GTG | TTG | AAG | AGA | CCA | GAA | CGT | 1290 |
| Ser | Leu | Cys | Ser | Ser | Ser | Thr | Arg | Ser | Val | Leu | Lys | Arg | Pro | Glu | Arg | |
| | | | 265 | | | | | 270 | | | | 275 | | | | |
| TCT | CAA | GAG | GAG | TCT | CCA | CCT | GGA | AGT | ACA | AAG | AGG | AGG | AAG | AGC | ATG | 1338 |
| Ser | Gln | Glu | Glu | Ser | Pro | Pro | Gly | Ser | Thr | Lys | Arg | Arg | Lys | Ser | Met | |
| | | 280 | | | | | 285 | | | | | 290 | | | | |
| TCT | GGG | GCC | AGC | CCC | AAA | GAG | TCA | ACT | AAT | CCA | GAG | AAG | GCC | CAT | GAG | 1386 |
| Ser | Gly | Ala | Ser | Pro | Lys | Glu | Ser | Thr | Asn | Pro | Glu | Lys | Ala | His | Glu | |
| | 295 | | | | | 300 | | | | | 305 | | | | | |
| ACT | CTT | CAT | CAG | TCT | TTA | TCC | CTG | GCA | TCT | TCC | CCC | AAA | GGA | ACC | ATT | 1434 |
| Thr | Leu | His | Gln | Ser | Leu | Ser | Leu | Ala | Ser | Ser | Pro | Lys | Gly | Thr | Ile | |
| 310 | | | | | 315 | | | | | 320 | | | | | 325 | |
| GAG | AAC | ATT | TTG | GAC | AAT | GAC | CCA | AGG | GAC | CTT | ATA | GGA | GAC | TTC | TCC | 1482 |
| Glu | Asn | Ile | Leu | Asp | Asn | Asp | Pro | Arg | Asp | Leu | Ile | Gly | Asp | Phe | Ser | |
| | | | | 330 | | | | 335 | | | | | | 340 | | |
| AAG | GGT | TAT | CTC | TTT | CAT | ACA | GTT | GCT | GGG | AAA | CAT | CAG | GAT | TTA | AAA | 1530 |
| Lys | Gly | Tyr | Leu | Phe | His | Thr | Val | Ala | Gly | Lys | His | Gln | Asp | Leu | Lys | |
| | | | 345 | | | | | 350 | | | | | 355 | | | |
| TAC | ATC | TCT | CCA | GAA | ATT | ATG | GCA | TCT | GTT | TTG | AAT | GGC | AAG | TTT | GCC | 1578 |
| Tyr | Ile | Ser | Pro | Glu | Ile | Met | Ala | Ser | Val | Leu | Asn | Gly | Lys | Phe | Ala | |
| | | 360 | | | | | 365 | | | | | 370 | | | | |
| AAC | CTC | ATT | AAA | GAG | TTT | GTT | ATC | ATC | GAC | TGT | CGA | TAC | CCA | TAT | GAA | 1626 |
| Asn | Leu | Ile | Lys | Glu | Phe | Val | Ile | Ile | Asp | Cys | Arg | Tyr | Pro | Tyr | Glu | |
| | 375 | | | | | 380 | | | | | 385 | | | | | |
| TAC | GAG | GGA | GGC | CAC | ATC | AAG | GGT | GCA | GTG | AAC | TTG | CAC | ATG | GAA | GAA | 1674 |
| Tyr | Glu | Gly | Gly | His | Ile | Lys | Gly | Ala | Val | Asn | Leu | His | Met | Glu | Glu | |
| 390 | | | | | 395 | | | | | 400 | | | | | 405 | |
| GAG | GTT | GAA | GAC | TTC | TTA | TTG | AAG | AAG | CCC | ATT | GTA | CCT | ACT | GAT | GGC | 1722 |
| Glu | Val | Glu | Asp | Phe | Leu | Leu | Lys | Lys | Pro | Ile | Val | Pro | Thr | Asp | Gly | |
| | | | | 410 | | | | 415 | | | | | | 420 | | |
| AAG | CGT | GTC | ATT | GTT | GTG | TTT | CAC | TGC | GAG | TTT | TCT | TCT | GAG | AGA | GGT | 1770 |
| Lys | Arg | Val | Ile | Val | Val | Phe | His | Cys | Glu | Phe | Ser | Ser | Glu | Arg | Gly | |
| | | | 425 | | | | | 430 | | | | | 435 | | | |
| CCC | CGC | ATG | TGC | CGG | TAT | GTG | AGA | GAG | AGA | GAT | CGC | CTG | GGT | AAT | GAA | 1818 |
| Pro | Arg | Met | Cys | Arg | Tyr | Val | Arg | Glu | Arg | Asp | Arg | Leu | Gly | Asn | Glu | |
| | | 440 | | | | | 445 | | | | | 450 | | | | |
| TAC | CCC | AAA | CTC | CAC | TAC | CCT | GAG | CTG | TAT | GTC | CTG | AAG | GGG | GGA | TAC | 1866 |
| Tyr | Pro | Lys | Leu | His | Tyr | Pro | Glu | Leu | Tyr | Val | Leu | Lys | Gly | Gly | Tyr | |
| | 455 | | | | | 460 | | | | | 465 | | | | | |
| AAG | GAG | TTC | TTT | ATG | AAA | TGC | CAG | TCT | TAC | TGT | GAG | CCC | CCT | AGC | TAC | 1914 |
| Lys | Glu | Phe | Phe | Met | Lys | Cys | Gln | Ser | Tyr | Cys | Glu | Pro | Pro | Ser | Tyr | |
| 470 | | | | | 475 | | | | | 480 | | | | | 485 | |
| CGG | CCC | ATG | CAC | CAC | GAG | GAC | TTT | AAA | GAA | GAC | CTG | AAG | AAG | TTC | CGC | 1962 |
| Arg | Pro | Met | His | His | Glu | Asp | Phe | Lys | Glu | Asp | Leu | Lys | Lys | Phe | Arg | |
| | | | | 490 | | | | 495 | | | | | | 500 | | |
| ACC | AAG | AGC | CGG | ACC | TGG | GCA | GGG | GAG | AAG | AGC | AAG | AGG | GAG | ATG | TAC | 2010 |
| Thr | Lys | Ser | Arg | Thr | Trp | Ala | Gly | Glu | Lys | Ser | Lys | Arg | Glu | Met | Tyr | |
| | | | 505 | | | | | 510 | | | | | 515 | | | |
| AGT | CGT | CTG | AAG | AAG | CTC | TGAGGCGGC | AGGACCAGCC | AGCAGCAGCC | | | | | | | | 2058 |
| Ser | Arg | Leu | Lys | Lys | Leu | | | | | | | | | | | |
| | | 520 | | | | | | | | | | | | | | |

CAAGCTTCCC TCCATCCCCC TTTACCCTCT TTCCTGCAGA GAAACTTAAG CAAAGGGGAC 2118

AGCTGTGTGA CATTTGGAGA GGGGGCCTGG GACTTCCATG CCTTAAACCT ACCTCCCACA 2178

CTCCCAAGGT TGGAGCCCAG GGCATCTTGC TGGCTACGCC TCTTCTGTCC CTGTTAGACG 2238

|                |                |                |                |                |        |
|----------------|----------------|----------------|----------------|----------------|--------|
| TCCTCCGTCC     | ATATCAGAAC     | TGTGCCACAA     | TGCAGTTCTG     | AGCACCGTGT     | CAAGCTGCTC | 2298 |
| TGAGCCACAG     | TGGGATGAAC     | CAGCCGGGGC     | CTTATCGGGC     | TCCAGCATCT     | CATGAGGGGA | 2358 |
| GAGGAGACGG     | AGGGGAGTAG     | AGAAGTTTAC     | ACAGAAATGC     | TGCTGGCCAA     | ATAGCAAAGA | 2418 |
| G              |                |                |                |                |        | 2419 |

( 2 ) INFORMATION FOR SEQ ID NO:2:

( i ) SEQUENCE CHARACTERISTICS:
            ( A ) LENGTH: 523 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

Met Glu Leu Gly Pro Ser Pro Ala Pro Arg Arg Leu Leu Phe Ala Cys
1 5 10 15

Ser Pro Pro Pro Ala Ser Gln Pro Val Val Lys Ala Leu Phe Gly Ala
20 25 30

Ser Ala Ala Gly Gly Leu Ser Pro Val Thr Asn Leu Thr Val Thr Met
35 40 45

Asp Gln Leu Gln Gly Leu Gly Ser Asp Tyr Glu Gln Pro Leu Glu Val
50 55 60

Lys Asn Asn Ser Asn Leu Gln Arg Met Gly Ser Ser Glu Ser Thr Asp
65 70 75 80

Ser Gly Phe Cys Leu Asp Ser Pro Gly Pro Leu Asp Ser Lys Glu Asn
85 90 95

Leu Glu Asn Pro Met Arg Arg Ile His Ser Leu Pro Gln Lys Leu Leu
100 105 110

Gly Cys Ser Pro Ala Leu Lys Arg Ser His Ser Asp Ser Leu Asp His
115 120 125

Asp Ile Phe Gln Leu Ile Asp Pro Asp Glu Asn Lys Glu Asn Glu Ala
130 135 140

Phe Glu Phe Lys Lys Pro Val Arg Pro Val Ser Arg Gly Cys Leu His
145 150 155 160

Ser His Gly Leu Gln Glu Gly Lys Asp Leu Phe Thr Gln Arg Gln Asn
165 170 175

Ser Ala Gln Leu Gly Met Leu Ser Ser Asn Glu Arg Asp Ser Ser Glu
180 185 190

Pro Gly Asn Phe Ile Pro Leu Phe Thr Pro Gln Ser Pro Val Thr Ala
195 200 205

Thr Leu Ser Asp Glu Asp Asp Gly Phe Val Asp Leu Leu Asp Gly Glu
210 215 220

Asn Leu Lys Asn Glu Glu Glu Thr Pro Ser Cys Met Ala Ser Leu Trp
225 230 235 240

Thr Ala Pro Leu Val Met Arg Thr Thr Asn Leu Asp Asn Arg Cys Lys
245 250 255

Leu Phe Asp Ser Pro Ser Leu Cys Ser Ser Ser Thr Arg Ser Val Leu
260 265 270

Lys Arg Pro Glu Arg ser Gln Glu Glu Ser Pro Pro Gly Ser Thr Lys
275 280 285

Arg Arg Lys Ser Met Ser Gly Ala Ser Pro Lys Glu Ser Thr Asn Pro
290 295 300

Glu Lys Ala His Glu Thr Leu His Gln Ser Leu Ser Leu Ala Ser Ser
305 310 315 320

Pro Lys Gly Thr Ile Glu Asn Ile Leu Asp Asn Asp Pro Arg Asp Leu

```
                                  325 330 335

Ile Gly Asp Phe Ser Lys Gly Tyr Leu Phe His Thr Val Ala Gly Lys
                         340 345 350

His Gln Asp Leu Lys Tyr Ile Ser Pro Glu Ile Met Ala Ser Val Leu
                    355 360 365

Asn Gly Lys Phe Ala Asn Leu Ile Lys Glu Phe Val Ile Ile Asp Cys
             370 375 380

Arg Tyr Pro Tyr Glu Tyr Glu Gly Gly His Ile Lys Gly Ala Val Asn
385 390 395 400

Leu His Met Glu Glu Glu Val Glu Asp Phe Leu Leu Lys Lys Pro Ile
                         405 410 415

Val Pro Thr Asp Gly Lys Arg Val Ile Val Val Phe His Cys Glu Phe
                    420 425 430

Ser Ser Glu Arg Gly Pro Arg Met Cys Arg Tyr Val Arg Glu Arg Asp
             435 440 445

Arg Leu Gly Asn Glu Tyr Pro Lys Leu His Tyr Pro Glu Leu Tyr Val
         450 455 460

Leu Lys Gly Gly Tyr Lys Glu Phe Phe Met Lys Cys Gln Ser Tyr Cys
465 470 475 480

Glu Pro Pro Ser Tyr Arg Pro Met His His Glu Asp Phe Lys Glu Asp
                         485 490 495

Leu Lys Lys Phe Arg Thr Lys Ser Arg Thr Trp Ala Gly Glu Lys Ser
                    500 505 510

Lys Arg Glu Met Tyr Ser Arg Leu Lys Lys Leu
             515 520
```

( 2 ) INFORMATION FOR SEQ ID NO:3:

( i ) SEQUENCE CHARACTERISTICS:
            ( A ) LENGTH: 2940 base pairs
            ( B ) TYPE: nucleic acid
            ( C ) STRANDEDNESS: double
            ( D ) TOPOLOGY: linear ( i i ) MOLECULE TYPE: DNA (genomic)

( i x ) FEATURE:
            ( A ) NAME/KEY: CDS
            ( B ) LOCATION: 73..1773

( x i ) SEQUENCE DESCRIPTION: SEQ ID NO:3:

```
CTGCCCTGCG  CCCGGCCCTC  CAGCCAGCCT  GCCAGCTGTG  CCGGCGTTTG  TTGGTCTGCC                60

GGCCCCGCCG  CG ATG GAG GTG CCC CAG CCG GAG CCC GCG CCA GGC TCG                       108
              Met Glu Val Pro Gln Pro Glu Pro Ala Pro Gly Ser
                1               5                   10

GCT CTC AGT CCA GCA GGC GTG TGC GGT GGC GCC CAG CGT CCG GGC CAC                      156
Ala Leu Ser Pro Ala Gly Val Cys Gly Gly Ala Gln Arg Pro Gly His
            15                  20                  25

CTC CCG GGC CTC CTG CTG GGA TCT CAT GGC CTC CTG GGG TCC CCG GTG                      204
Leu Pro Gly Leu Leu Leu Gly Ser His Gly Leu Leu Gly Ser Pro Val
        30                  35                  40

CGG GCG GCC GCT TCC TCG CCG GTC ACC ACC CTC ACC CAG ACC ATG CAC                      252
Arg Ala Ala Ala Ser Ser Pro Val Thr Thr Leu Thr Gln Thr Met His
45                  50                  55                  60

GAC CTC GCC GGG CTC GGC AGC CGC AGC CGC CTG ACG CAC CTA TCC CTG                      300
Asp Leu Ala Gly Leu Gly Ser Arg Ser Arg Leu Thr His Leu Ser Leu
                65                  70                  75

TCT CGA CGG GCA TCC GAA TCC TCC CTG TCG TCT GAA TCC TCC GAA TCT                      348
Ser Arg Arg Ala Ser Glu Ser Ser Leu Ser Ser Glu Ser Ser Glu Ser
            80                  85                  90

TCT GAT GCA GGT CTC TGC ATG GAT TCC CCC AGC CCT ATG GAC CCC CAC                      396
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Ser | Asp | Ala  95 | Gly | Leu | Cys | Met | Asp  100 | Ser | Pro | Ser | Pro  105 | Met | Asp | Pro | His |  |

| ATG | GCG | GAG | CAG | ACG | TTT | GAA | CAG | GCC | ATC | CAG | GCA | GCC | AGC | CGG | ATC | 444 |
| --- | --- | --- | --- | --- | --- | --- | --- | --- | --- | --- | --- | --- | --- | --- | --- | --- |
| Met | Ala  110 | Glu | Gln | Thr | Phe | Glu  115 | Gln | Ala | Ile | Gln  120 | Ala | Ala | Ser | Arg | Ile |  |

| ATT | CGA | AAC | GAG | CAG | TTT | GCC | ATC | AGA | CGC | TTC | CAG | TCT | ATG | CCG | GTG | 492 |
| --- | --- | --- | --- | --- | --- | --- | --- | --- | --- | --- | --- | --- | --- | --- | --- | --- |
| Ile  125 | Arg | Asn | Glu | Gln | Phe  130 | Ala | Ile | Arg | Arg | Phe  135 | Gln | Ser | Met | Pro | Val  140 |  |

| AGG | CTG | CTG | GGC | CAC | AGC | CCC | GTG | CTT | CGG | AAC | ATC | ACC | AAC | TCC | CAG | 540 |
| --- | --- | --- | --- | --- | --- | --- | --- | --- | --- | --- | --- | --- | --- | --- | --- | --- |
| Arg | Leu | Leu | Gly | His  145 | Ser | Pro | Val | Leu | Arg  150 | Asn | Ile | Thr | Asn | Ser  155 | Gln |  |

| GCG | CCC | GAC | GGC | CGG | AGG | AAG | AGC | GAG | GCG | GGC | AGT | GGA | GCT | GCC | AGC | 588 |
| --- | --- | --- | --- | --- | --- | --- | --- | --- | --- | --- | --- | --- | --- | --- | --- | --- |
| Ala | Pro | Asp | Gly  160 | Arg | Arg | Lys | Ser | Glu  165 | Ala | Gly | Ser | Gly | Ala  170 | Ala | Ser |  |

| AGC | TCT | GGG | GAA | GAC | AAG | GAG | AAT | GAT | GGA | TTT | GTC | TTC | AAG | ATG | CCA | 636 |
| --- | --- | --- | --- | --- | --- | --- | --- | --- | --- | --- | --- | --- | --- | --- | --- | --- |
| Ser | Ser | Gly  175 | Glu | Asp | Lys | Glu | Asn  180 | Asp | Gly | Phe | Val | Phe  185 | Lys | Met | Pro |  |

| TGG | AAG | CCC | ACA | CAT | CCC | AGC | TCC | ACC | CAT | GCT | CTG | GCA | GAG | TGG | GCC | 684 |
| --- | --- | --- | --- | --- | --- | --- | --- | --- | --- | --- | --- | --- | --- | --- | --- | --- |
| Trp | Lys  190 | Pro | Thr | His | Pro | Ser  195 | Ser | Thr | His | Ala | Leu  200 | Ala | Glu | Trp | Ala |  |

| AGC | CGC | AGG | GAA | GCC | TTT | GCC | CAG | AGA | CCC | AGC | TCG | GCC | CCC | GAC | CTG | 732 |
| --- | --- | --- | --- | --- | --- | --- | --- | --- | --- | --- | --- | --- | --- | --- | --- | --- |
| Ser  205 | Arg | Arg | Glu | Ala | Phe  210 | Ala | Gln | Arg | Pro | Ser  215 | Ser | Ala | Pro | Asp | Leu  220 |  |

| ATG | TGT | CTC | AGT | CCT | GAC | CGG | AAG | ATG | GAA | GTG | GAG | GAG | CTC | AGC | CCC | 780 |
| --- | --- | --- | --- | --- | --- | --- | --- | --- | --- | --- | --- | --- | --- | --- | --- | --- |
| Met | Cys | Leu | Ser | Pro  225 | Asp | Arg | Lys | Met | Glu  230 | Val | Glu | Glu | Leu | Ser  235 | Pro |  |

| CTG | GCC | CTA | GGT | CGC | TTC | TCT | CTG | ACC | CCT | GCA | GAG | GGG | GAT | ACT | GAG | 828 |
| --- | --- | --- | --- | --- | --- | --- | --- | --- | --- | --- | --- | --- | --- | --- | --- | --- |
| Leu | Ala | Leu | Gly  240 | Arg | Phe | Ser | Leu | Thr  245 | Pro | Ala | Glu | Gly | Asp  250 | Thr | Glu |  |

| GAA | GAT | GAT | GGA | TTT | GTG | GAC | ATC | CTA | GAG | AGT | GAC | TTA | AAG | GAT | GAT | 876 |
| --- | --- | --- | --- | --- | --- | --- | --- | --- | --- | --- | --- | --- | --- | --- | --- | --- |
| Glu | Asp | Asp  255 | Gly | Phe | Val | Asp | Ile  260 | Leu | Glu | Ser | Asp | Leu  265 | Lys | Asp | Asp |  |

| GAT | GCA | GTT | CCC | CCA | GGC | ATG | GAG | AGT | CTC | ATT | AGT | GCC | CCA | CTG | GTC | 924 |
| --- | --- | --- | --- | --- | --- | --- | --- | --- | --- | --- | --- | --- | --- | --- | --- | --- |
| Asp | Ala  270 | Val | Pro | Pro | Gly | Met  275 | Glu | Ser | Leu | Ile | Ser  280 | Ala | Pro | Leu | Val |  |

| AAG | ACC | TTG | GAA | AAG | GAA | GAG | GAA | AAG | GAC | CTC | GTC | ATG | TAC | AGC | AAG | 972 |
| --- | --- | --- | --- | --- | --- | --- | --- | --- | --- | --- | --- | --- | --- | --- | --- | --- |
| Lys  285 | Thr | Leu | Glu | Lys | Glu  290 | Glu | Glu | Lys | Asp | Leu  295 | Val | Met | Tyr | Ser | Lys  300 |  |

| TGC | CAG | CGG | CTC | TTC | CGC | TCT | CCG | TCC | ATG | CCC | TGC | AGC | GTG | ATC | CGG | 1020 |
| --- | --- | --- | --- | --- | --- | --- | --- | --- | --- | --- | --- | --- | --- | --- | --- | --- |
| Cys | Gln | Arg | Leu | Phe  305 | Arg | Ser | Pro | Ser | Met  310 | Pro | Cys | Ser | Val | Ile  315 | Arg |  |

| CCC | ATC | CTC | AAG | AGG | CTG | GAG | CGG | CCC | CAG | GAC | AGG | GAC | ACG | CCC | GTG | 1068 |
| --- | --- | --- | --- | --- | --- | --- | --- | --- | --- | --- | --- | --- | --- | --- | --- | --- |
| Pro | Ile | Leu | Lys  320 | Arg | Leu | Glu | Arg | Pro  325 | Gln | Asp | Arg | Asp | Thr  330 | Pro | Val |  |

| CAG | AAT | AAG | CGG | AGG | CGG | AGC | GTG | ACC | CCT | CCT | GAG | GAG | CAG | CAG | GAG | 1116 |
| --- | --- | --- | --- | --- | --- | --- | --- | --- | --- | --- | --- | --- | --- | --- | --- | --- |
| Gln | Asn | Lys  335 | Arg | Arg | Arg | Ser | Val  340 | Thr | Pro | Pro | Glu | Glu  345 | Gln | Gln | Glu |  |

| GCT | GAG | GAA | CCT | AAA | GCC | CGC | GTC | CTC | CGC | TCA | AAA | TCA | CTG | TGT | CAC | 1164 |
| --- | --- | --- | --- | --- | --- | --- | --- | --- | --- | --- | --- | --- | --- | --- | --- | --- |
| Ala | Glu  350 | Glu | Pro | Lys | Ala | Arg  355 | Val | Leu | Arg | Ser | Lys  360 | Ser | Leu | Cys | His |  |

| GAT | GAG | ATC | GAG | AAC | CTC | CTG | GAC | AGT | GAC | CAC | CGA | GAG | CTG | ATT | GGA | 1212 |
| --- | --- | --- | --- | --- | --- | --- | --- | --- | --- | --- | --- | --- | --- | --- | --- | --- |
| Asp  365 | Glu | Ile | Glu | Asn | Leu  370 | Leu | Asp | Ser | Asp | His  375 | Arg | Glu | Leu | Ile | Gly  380 |  |

| GAT | TAC | TCT | AAG | GCC | TTC | CTC | CTA | CAG | ACA | GTA | GAC | GGA | AAG | CAC | CAA | 1260 |
| --- | --- | --- | --- | --- | --- | --- | --- | --- | --- | --- | --- | --- | --- | --- | --- | --- |
| Asp | Tyr | Ser | Lys | Ala  385 | Phe | Leu | Leu | Gln | Thr  390 | Val | Asp | Gly | Lys | His  395 | Gln |  |

| GAC | CTC | AAG | TAC | ATC | TCA | CCA | GAA | ACG | ATG | GTG | GCC | CTA | TTG | ACG | GGC | 1308 |
| --- | --- | --- | --- | --- | --- | --- | --- | --- | --- | --- | --- | --- | --- | --- | --- | --- |
| Asp | Leu | Lys | Tyr  400 | Ile | Ser | Pro | Glu | Thr  405 | Met | Val | Ala | Leu | Leu  410 | Thr | Gly |  |

| AAG | TTC | AGC | AAC | ATC | GTG | GAT | AAG | TTT | GTG | ATT | GTA | GAC | TGC | AGA | TAC | 1356 |
| --- | --- | --- | --- | --- | --- | --- | --- | --- | --- | --- | --- | --- | --- | --- | --- | --- |
| Lys | Phe | Ser  415 | Asn | Ile | Val | Asp | Lys  420 | Phe | Val | Ile | Val | Asp  425 | Cys | Arg | Tyr |  |

| | | | | | | | | | | | | | | | | |
|---|---|---|---|---|---|---|---|---|---|---|---|---|---|---|---|---|
|CCC|TAT|GAA|TAT|GAA|GGC|GGG|CAC|ATC|AAG|ACT|GCG|GTG|AAC|TTG|CCC|1404|
|Pro|Tyr|Glu|Tyr|Glu|Gly|Gly|His|Ile|Lys|Thr|Ala|Val|Asn|Leu|Pro| |
| |430| | | |435| | | |440| | | | | | | |
|CTG|GAA|CGC|GAC|GCC|GAG|AGC|TTC|CTA|CTG|AAG|AGC|CCC|ATC|GCG|CCC|1452|
|Leu|Glu|Arg|Asp|Ala|Glu|Ser|Phe|Leu|Leu|Lys|Ser|Pro|Ile|Ala|Pro| |
|445| | | | |450| | | |455| | | | | |460| |
|TGT|AGC|CTG|GAC|AAG|AGA|GTC|ATC|CTC|ATT|TTC|CAC|TGT|GAA|TTC|TCA|1500|
|Cys|Ser|Leu|Asp|Lys|Arg|Val|Ile|Leu|Ile|Phe|His|Cys|Glu|Phe|Ser| |
| | | | |465| | | | |470| | | | |475| | |
|TCT|GAG|CGT|GGG|CCC|CGC|ATG|TGC|CGT|TTC|ATC|AGG|GAA|CGA|GAC|CGT|1548|
|Ser|Glu|Arg|Gly|Pro|Arg|Met|Cys|Arg|Phe|Ile|Arg|Glu|Arg|Asp|Arg| |
| | | |480| | | | |485| | | | |490| | | |
|GCT|GTC|AAC|GAC|TAC|CCC|AGC|CTC|TAC|TAC|CCT|GAG|ATG|TAT|ATC|CTG|1596|
|Ala|Val|Asn|Asp|Tyr|Pro|Ser|Leu|Tyr|Tyr|Pro|Glu|Met|Tyr|Ile|Leu| |
| | |495| | | | |500| | | | |505| | | | |
|AAA|GGC|GGC|TAC|AAG|GAG|TTC|TTC|CCT|CAG|CAC|CCG|AAC|TTC|TGT|GAA|1644|
|Lys|Gly|Gly|Tyr|Lys|Glu|Phe|Phe|Pro|Gln|His|Pro|Asn|Phe|Cys|Glu| |
| |510| | | | |515| | | | |520| | | | | |
|CCC|CAG|GAC|TAC|CGG|CCC|ATG|AAC|CAC|GAG|GCC|TTC|AAG|GAT|GAG|CTA|1692|
|Pro|Gln|Asp|Tyr|Arg|Pro|Met|Asn|His|Glu|Ala|Phe|Lys|Asp|Glu|Leu| |
|525| | | | |530| | | | |535| | | | |540| |
|AAG|ACC|TTC|CGC|CTC|AAG|ACT|CGC|AGC|TGG|GCT|GGG|GAG|CGG|AGC|CGG|1740|
|Lys|Thr|Phe|Arg|Leu|Lys|Thr|Arg|Ser|Trp|Ala|Gly|Glu|Arg|Ser|Arg| |
| | | | |545| | | | |550| | | | |555| | |
|CGG|GAG|CTC|TGT|AGC|CGG|CTG|CAG|GAC|CAG|TGAGGGGCCT|GCGCCAGTCC| | | | |1790|
|Arg|Glu|Leu|Cys|Ser|Arg|Leu|Gln|Asp|Gln| | | | | | | |
| | | |560| | | | |565| | | | | | | | |

| | | | | |
|---|---|---|---|---|
|TGCTACCTCC|CTTGCCTTTC|GAGGCCTGAA|GCCAGCTGCC|CTATGGGCCT GCCGGGCTGA|1850|
|GGGCCTGCTG|GAGGCCTCAG|GTGCTGTCCA|TGGGAAAGAT|GGTGTGGTGT CCTGCCTGTC|1910|
|TGCCCCAGCC|CAGATTCCCC|TGTGTCATCC|CATCATTTTC|CATATCCTGG TGCCCCCCAC|1970|
|CCCTGGAAGA|GCCCAGTCTG|TTGAGTTAGT|TAAGTTGGGT|TAATACCAGC TTAAAGGCAG|2030|
|TATTTTGTGT|CCTCCAGGAG|CTTCTTGTTT|CCTTGTTAGG|GTTAACCCTT CATCTTCCTG|2090|
|TGTCCTGAAA|CGCTCCTTTG|TGTGTGTGTC|AGCTGAGGCT|GGGGAGAGCC GTGGTCCCTG|2150|
|AGGATGGGTC|AGAGCTAAAC|TCCTTCCTGG|CCTGAGAGTC|AGCTCTCTGC CCTGTGTACT|2210|
|TCCCGGGCCA|GGGCTGCCCC|TAATCTCTGT|AGGAACCGTG|GTATGTCTGC CATGTTGCCC|2270|
|CTTTCTCTTT|TCCCCTTTCC|TGTCCCACCA|TACGAGCACC|TCCAGCCTGA ACAGAAGCTC|2330|
|TTACTCTTTC|CTATTTCAGT|GTTACCTGTG|TGCTTGGTCT|GTTTGACTTT ACGCCCATCT|2390|
|CAGGACACTT|CCGTAGACTG|TTTAGGTTCC|CCTGTCAAAT|ATCAGTTACC CACTCGGTCC|2450|
|CAGTTTTGTT|GCCCCAGAAA|GGGATGTTAT|TATCCTTGGG|GCTCCCAGG CAAGGGTTA|2510|
|AGGCCTGAAT|CATGAGCCTG|CTGGAAGCCC|AGCCCTACT|GCTGTGAACC CTGGGGCCTG|2570|
|ACTGCTCAGA|ACTTGCTGCT|GTCTTGTTGC|GGATGGATGG|AAGGTTGGAT GGATGGGTGG|2630|
|ATGGCCGTGG|ATGGCCGTGG|ATGCGCAGTG|CCTTGCATAC|CCAAACCAGG TGGGAGCGTT|2690|
|TTGTTGAGCA|TGACACCTGC|AGCAGGAATA|TATGTGTGCC|TATTTGTGTG ACAAAAATA|2750|
|TTTACACTTA|GGGTTTGGAG|CTATTCAAGA|GGAAATGTCA|CAGAAGCAGC TAAACCAAGG|2810|
|ACTGAGCACC|CTCTGGATTC|TGAATCTCAA|GATGGGGGCA|GGGCTGTGCT TGAAGGCCCT|2870|
|GCTGAGTCAT|CTGTTAGGGC|CTTGGTTCAA|TAAAGCACTG|AGCAAGTTGA GAAAAAAAA|2930|
|AAAAAAAAAA| | | | |2940|

( 2 ) INFORMATION FOR SEQ ID NO:4:

( i ) SEQUENCE CHARACTERISTICS:
        ( A ) LENGTH: 566 amino acids (B) TYPE: amino acid
(D) TOPOLOGY: linear (ii) MOLECULE TYPE: protein (xi) SEQUENCE DESCRIPTION: SEQ ID NO:4:

| Met | Glu | Val | Pro | Gln | Pro | Glu | Pro | Ala | Pro | Gly | Ser | Ala | Leu | Ser | Pro |
| 1 | | | | 5 | | | | | 10 | | | | | 15 | |

| Ala | Gly | Val | Cys | Gly | Gly | Ala | Gln | Arg | Pro | Gly | His | Leu | Pro | Gly | Leu |
| | | | 20 | | | | | 25 | | | | | 30 | | |

| Leu | Leu | Gly | Ser | His | Gly | Leu | Leu | Gly | Ser | Pro | Val | Arg | Ala | Ala | Ala |
| | | 35 | | | | | 40 | | | | | 45 | | | |

| Ser | Ser | Pro | Val | Thr | Thr | Leu | Thr | Gln | Thr | Met | His | Asp | Leu | Ala | Gly |
| | 50 | | | | | 55 | | | | | 60 | | | | |

| Leu | Gly | Ser | Arg | Ser | Arg | Leu | Thr | His | Leu | Ser | Leu | Ser | Arg | Arg | Ala |
| 65 | | | | | 70 | | | | | 75 | | | | | 80 |

| Ser | Glu | Ser | Ser | Leu | Ser | Ser | Glu | Ser | Ser | Glu | Ser | Ser | Asp | Ala | Gly |
| | | | | 85 | | | | | 90 | | | | | 95 | |

| Leu | Cys | Met | Asp | Ser | Pro | Ser | Pro | Met | Asp | Pro | His | Met | Ala | Glu | Gln |
| | | | 100 | | | | | 105 | | | | | 110 | | |

| Thr | Phe | Glu | Gln | Ala | Ile | Gln | Ala | Ala | Ser | Arg | Ile | Ile | Arg | Asn | Glu |
| | | | 115 | | | | | 120 | | | | | 125 | | |

| Gln | Phe | Ala | Ile | Arg | Arg | Phe | Gln | Ser | Met | Pro | Val | Arg | Leu | Leu | Gly |
| | 130 | | | | | 135 | | | | | 140 | | | | |

| His | Ser | Pro | Val | Leu | Arg | Asn | Ile | Thr | Asn | Ser | Gln | Ala | Pro | Asp | Gly |
| 145 | | | | | 150 | | | | | 155 | | | | | 160 |

| Arg | Arg | Lys | Ser | Glu | Ala | Gly | Ser | Gly | Ala | Ala | Ser | Ser | Ser | Gly | Glu |
| | | | | 165 | | | | | 170 | | | | | 175 | |

| Asp | Lys | Glu | Asn | Asp | Gly | Phe | Val | Phe | Lys | Met | Pro | Trp | Lys | Pro | Thr |
| | | | 180 | | | | | 185 | | | | | 190 | | |

| His | Pro | Ser | Ser | Thr | His | Ala | Leu | Ala | Glu | Trp | Ala | Ser | Arg | Arg | Glu |
| | | 195 | | | | | 200 | | | | | 205 | | | |

| Ala | Phe | Ala | Gln | Arg | Pro | Ser | Ser | Ala | Pro | Asp | Leu | Met | Cys | Leu | Ser |
| | 210 | | | | | 215 | | | | | 220 | | | | |

| Pro | Asp | Arg | Lys | Met | Glu | Val | Glu | Glu | Leu | Ser | Pro | Leu | Ala | Leu | Gly |
| 225 | | | | | 230 | | | | | 235 | | | | | 240 |

| Arg | Phe | Ser | Leu | Thr | Pro | Ala | Glu | Gly | Asp | Thr | Glu | Glu | Asp | Asp | Gly |
| | | | | 245 | | | | | 250 | | | | | 255 | |

| Phe | Val | Asp | Ile | Leu | Glu | Ser | Asp | Leu | Lys | Asp | Asp | Asp | Ala | Val | Pro |
| | | | 260 | | | | | 265 | | | | | 270 | | |

| Pro | Gly | Met | Glu | Ser | Leu | Ile | Ser | Ala | Pro | Leu | Val | Lys | Thr | Leu | Glu |
| | | 275 | | | | | 280 | | | | | 285 | | | |

| Lys | Glu | Glu | Lys | Asp | Leu | Val | Met | Tyr | Ser | Lys | Cys | Gln | Arg | Leu |
| | 290 | | | | | 295 | | | | | 300 | | | | |

| Phe | Arg | Ser | Pro | Ser | Met | Pro | Cys | Ser | Val | Ile | Arg | Pro | Ile | Leu | Lys |
| 305 | | | | | 310 | | | | | 315 | | | | | 320 |

| Arg | Leu | Glu | Arg | Pro | Gln | Asp | Arg | Asp | Thr | Pro | Val | Gln | Asn | Lys | Arg |
| | | | | 325 | | | | | 330 | | | | | 335 | |

| Arg | Arg | Ser | Val | Thr | Pro | Pro | Glu | Glu | Gln | Gln | Glu | Ala | Glu | Glu | Pro |
| | | | 340 | | | | | 345 | | | | | 350 | | |

| Lys | Ala | Arg | Val | Leu | Arg | Ser | Lys | Ser | Leu | Cys | His | Asp | Glu | Ile | Glu |
| | | 355 | | | | | 360 | | | | | 365 | | | |

| Asn | Leu | Leu | Asp | Ser | Asp | His | Arg | Glu | Leu | Ile | Gly | Asp | Tyr | Ser | Lys |
| | 370 | | | | | 375 | | | | | 380 | | | | |

| Ala | Phe | Leu | Leu | Gln | Thr | Val | Asp | Gly | Lys | His | Gln | Asp | Leu | Lys | Tyr |
| 385 | | | | | 390 | | | | | 395 | | | | | 400 |

| | | | | | | | | | | | | | | |
|---|---|---|---|---|---|---|---|---|---|---|---|---|---|---|
| Ile | Ser | Pro | Glu | Thr<br>405 | Met | Val | Ala | Leu | Leu<br>410 | Thr | Gly | Lys | Phe | Ser<br>415 | Asn |
| Ile | Val | Asp | Lys<br>420 | Phe | Val | Ile | Val | Asp<br>425 | Cys | Arg | Tyr | Pro | Tyr<br>430 | Glu | Tyr |
| Glu | Gly | Gly<br>435 | His | Ile | Lys | Thr | Ala<br>440 | Val | Asn | Leu | Pro | Leu<br>445 | Glu | Arg | Asp |
| Ala | Glu<br>450 | Ser | Phe | Leu | Leu | Lys<br>455 | Ser | Pro | Ile | Ala | Pro<br>460 | Cys | Ser | Leu | Asp |
| Lys<br>465 | Arg | Val | Ile | Leu | Ile<br>470 | Phe | His | Cys | Glu | Phe<br>475 | Ser | Ser | Glu | Arg | Gly<br>480 |
| Pro | Arg | Met | Cys | Arg<br>485 | Phe | Ile | Arg | Glu | Arg<br>490 | Asp | Arg | Ala | Val | Asn<br>495 | Asp |
| Tyr | Pro | Ser | Leu<br>500 | Tyr | Tyr | Pro | Glu | Met<br>505 | Tyr | Ile | Leu | Lys | Gly<br>510 | Gly | Tyr |
| Lys | Glu | Phe<br>515 | Phe | Pro | Gln | His | Pro<br>520 | Asn | Phe | Cys | Glu | Pro<br>525 | Gln | Asp | Tyr |
| Arg | Pro<br>530 | Met | Asn | His | Glu | Ala<br>535 | Phe | Lys | Asp | Glu | Leu<br>540 | Lys | Thr | Phe | Arg |
| Leu<br>545 | Lys | Thr | Arg | Ser | Trp<br>550 | Ala | Gly | Glu | Arg | Ser<br>555 | Arg | Arg | Glu | Leu | Cys<br>560 |
| Ser | Arg | Leu | Gln | Asp<br>565 | Gln | | | | | | | | | | |

( 2 ) INFORMATION FOR SEQ ID NO:5:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

| | | | | | | | | | | | | | | |
|---|---|---|---|---|---|---|---|---|---|---|---|---|---|---|
| Leu<br>1 | Asp | Asn | Asp | Pro<br>5 | Arg | Asp | Leu | Ile | Gly<br>10 | Asp | Phe | Ser | Lys | Gly<br>15 | Tyr |
| Leu | Phe | His | Thr<br>20 | Val | Ala | Gly | Lys | His<br>25 | Gln | Asp | Leu | Lys | Tyr<br>30 | Ile | Ser |
| Pro | Glu | Ile<br>35 | Met | Ala | Ser | Val | Leu<br>40 | Asn | Gly | Lys | Phe | Ala<br>45 | Asn | Leu | Ile |
| Lys | Glu<br>50 | Phe | Val | Ile | Ile | Asp<br>55 | Cys | Arg | Tyr | Pro | Tyr<br>60 | Glu | Tyr | Glu | Gly |
| Gly<br>65 | His | Ile | Lys | Gly<br>70 | Ala | Val | Asn | Leu | His<br>75 | Met | Glu | Glu | Glu | Val<br>80 | Glu |
| Asp | Phe | Leu | Leu | Lys<br>85 | Lys | Pro | Ile | Val | Pro<br>90 | Xaa | Xaa | Xaa | Xaa | Xaa<br>95 | |
| Xaa | Xaa | Thr | Asp<br>100 | Gly | Lys | Arg | Val | Ile<br>105 | Val | Val | Phe | His<br>110 | Cys | Glu | Phe |
| Ser | Ser | Glu<br>115 | Arg | Gly | Pro | Arg | Met<br>120 | Cys | Arg | Tyr | Val | Arg<br>125 | Glu | Arg | Asp |
| Arg | Leu<br>130 | Gly | Asn | Glu | Xaa | Xaa<br>135 | Tyr | Pro | Lys | Leu | His<br>140 | Tyr | Pro | Glu | Leu |
| Tyr | Val<br>145 | Leu | Lys | Gly | Gly<br>150 | Tyr | Lys | Glu | Phe | Phe<br>155 | Met | Lys | Cys | Gln | Ser<br>160 |
| Tyr | Cys | Glu | Pro | Pro<br>165 | Ser | Tyr | Arg | Pro | Met<br>170 | His | His | Glu | Asp | Phe<br>175 | Lys |
| Glu | Asp | Leu | Lys<br>180 | Lys | Phe | Arg | Thr | Lys<br>185 | Ser | Arg | Thr | Trp | Ala<br>190 | Gly | Glu |
| Lys | Ser | Lys | Arg | Glu | Met | Tyr | Ser | Arg | Leu | Lys | Lys | Leu | | | |

```
                                           195                       200                      205
```

( 2 ) INFORMATION FOR SEQ ID NO:6:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Leu  Asp  Ser  Asp  His  Arg  Glu  Leu  Ile  Gly  Asp  Tyr  Ser  Lys  Ala  Phe
 1              5                  10                      15

Leu  Leu  Gln  Thr  Val  Asp  Gly  Lys  His  Gln  Asp  Leu  Lys  Tyr  Ile  Ser
         20                      25                      30

Pro  Glu  Thr  Val  Met  Ala  Leu  Leu  Thr  Gly  Lys  Phe  Ser  Asn  Ile  Val
         35                      40                      45

Asp  Lys  Phe  Val  Ile  Val  Asp  Cys  Arg  Tyr  Pro  Tyr  Glu  Tyr  Glu  Gly
    50                      55                      60

Gly  His  Ile  Lys  Thr  Ala  Val  Asn  Leu  Pro  Leu  Glu  Arg  Asp  Ala  Glu
65                      70                      75                       80

Ser  Phe  Leu  Leu  Lys  Ser  Pro  Ile  Ala  Pro  Cys  Xaa  Xaa  Xaa  Xaa  Xaa
                85                      90                      95

Xaa  Xaa  Ser  Leu  Asp  Lys  Arg  Val  Ile  Leu  Ile  Phe  His  Cys  Glu  Phe
              100                     105                     110

Ser  Ser  Glu  Arg  Gly  Pro  Arg  Met  Cys  Arg  Phe  Ile  Arg  Glu  Arg  Asp
              115                     120                     125

Arg  Ala  Val  Asn  Asp  Xaa  Xaa  Tyr  Pro  Ser  Leu  Tyr  Tyr  Pro  Glu  Met
         130                     135                     140

Tyr  Ile  Leu  Lys  Gly  Gly  Tyr  Lys  Glu  Phe  Phe  Pro  Gln  His  Pro  Asn
145                     150                     155                     160

Phe  Cys  Glu  Pro  Gln  Asp  Tyr  Arg  Pro  Met  Asn  His  Glu  Ala  Phe  Lys
                165                     170                     175

Asp  Glu  Leu  Lys  Thr  Phe  Arg  Leu  Lys  Thr  Arg  Ser  Trp  Ala  Gly  Glu
              180                     185                     190

Arg  Ser  Arg  Arg  Glu  Leu  Cys  Ser  Arg  Leu  Gln  Asp  Gln
              195                     200                     205
```

( 2 ) INFORMATION FOR SEQ ID NO:7:

( i ) SEQUENCE CHARACTERISTICS:
        ( A ) LENGTH: 208 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Glu  Asp  Ser  Asn  Gln  Gly  His  Leu  Ile  Gly  Asp  Phe  Ser  Lys  Val  Cys
 1              5                  10                      15

Ala  Leu  Pro  Thr  Val  Ser  Gly  Lys  His  Gln  Asp  Leu  Lys  Tyr  Val  Asn
         20                      25                      30

Pro  Glu  Thr  Val  Ala  Ala  Leu  Leu  Ser  Gly  Lys  Phe  Gln  Gly  Leu  Ile
         35                      40                      45

Glu  Lys  Phe  Tyr  Val  Ile  Asp  Cys  Arg  Tyr  Pro  Tyr  Glu  Tyr  Leu  Gly
    50                      55                      60

Gly  His  Ile  Gln  Gly  Ala  Leu  Asn  Leu  Tyr  Ser  Gln  Glu  Glu  Leu  Phe
65                      70                      75                       80

Asn  Phe  Phe  Leu  Lys  Lys  Pro  Ile  Val  Pro  Leu  Xaa  Xaa  Xaa  Xaa  Xaa
                85                      90                      95
```

```
Xaa  Xaa  Asp  Thr  Gln  Lys  Arg  Ile  Ile  Ile  Val  Phe  His  Cys  Glu  Phe
          100                      105                     110

Ser  Ser  Glu  Arg  Gly  Pro  Arg  Met  Cys  Arg  Cys  Leu  Arg  Glu  Glu  Asp
          115                      120                     125

Arg  Ser  Leu  Asn  Gln  Xaa  Xaa  Tyr  Pro  Ala  Leu  Tyr  Tyr  Pro  Glu  Leu
     130                 135                     140

Tyr  Ile  Leu  Lys  Gly  Gly  Tyr  Arg  Asp  Phe  Phe  Pro  Glu  Tyr  Met  Glu
145                      150                 155                          160

Leu  Cys  Glu  Pro  Gln  Ser  Tyr  Cys  Pro  Met  His  His  Gln  Asp  His  Lys
                    165                      170                     175

Thr  Glu  Leu  Leu  Arg  Cys  Arg  Ser  Gln  Ser  Lys  Val  Gln  Glu  Gly  Glu
                    180                      185                     190

Arg  Gln  Leu  Arg  Glu  Gln  Ile  Ala  Leu  Leu  Val  Lys  Asp  Met  Ser  Pro
               195                 200                     205
```

( 2 ) INFORMATION FOR SEQ ID NO:8:

( i ) SEQUENCE CHARACTERISTICS:
        ( A ) LENGTH: 211 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Glu  Asn  Arg  Asn  Glu  Pro  Glu  Leu  Ile  Gly  Asp  Phe  Ser  Lys  Ala  Tyr
1                   5                      10                      15

Ser  Leu  Pro  Leu  Met  Glu  Gly  Arg  His  Arg  Asp  Leu  Lys  Ser  Ile  Ser
               20                      25                      30

Ser  Glu  Thr  Val  Ala  Arg  Leu  Leu  Lys  Gly  Glu  Phe  Ser  Asp  Lys  Val
          35                      40                      45

Ala  Ser  Tyr  Arg  Ile  Ile  Asp  Cys  Arg  Tyr  Pro  Tyr  Glu  Phe  Glu  Gly
     50                      55                      60

Gly  His  Ile  Glu  Gly  Ala  Lys  Asn  Leu  Tyr  Thr  Thr  Glu  Gln  Ile  Leu
65                      70                      75                       80

Asp  Glu  Phe  Leu  Thr  Val  Gln  Gln  Thr  Glu  Leu  Gln  Gln  Gln  Gln  Asn
                    85                      90                       95

Ala  Glu  Ser  Gly  His  Lys  Arg  Asn  Ile  Ile  Ile  Phe  His  Cys  Glu  Phe
          100                     105                     110

Ser  Ser  Glu  Arg  Gly  Pro  Lys  Met  Ser  Arg  Gly  Leu  Arg  Asn  Leu  Asp
          115                     120                     125

Arg  Glu  Arg  Asn  Thr  Asn  Ala  Tyr  Pro  Ala  Leu  His  Tyr  Pro  Glu  Ile
     130                     135                     140

Tyr  Leu  Leu  His  Asn  Gly  Tyr  Lys  Glu  Phe  Phe  Glu  Ser  His  Val  Glu
145                     150                     155                      160

Leu  Cys  Glu  Pro  His  Ala  Tyr  Arg  Thr  Met  Leu  Asp  Pro  Ala  Tyr  Asn
                    165                     170                     175

Glu  Ala  Tyr  Arg  His  Phe  Arg  Ala  Lys  Ser  Lys  Ser  Xaa  Trp  Asn  Gly
               180                     185                     190

Asp  Gly  Leu  Gly  Gly  Ala  Thr  Gly  Arg  Leu  Lys  Lys  Ser  Arg  Ser  Arg
          195                     200                     205

Leu  Met  LeuG
          210
```

( 2 ) INFORMATION FOR SEQ ID NO:9:

( i ) SEQUENCE CHARACTERISTICS:
        ( A ) LENGTH: 211 amino acids
        ( B ) TYPE: amino acid ( D ) TOPOLOGY: linear ( i i ) MOLECULE TYPE: peptide ( x i ) SEQUENCE DESCRIPTION: SEQ ID NO:9:

| Ser<br>1 | Thr | Lys | Glu<br>5 | Ser | Glu | Arg | Phe | Ile<br>10 | Ser | His | Val | Glu | Asp<br>15 | Leu |
|---|---|---|---|---|---|---|---|---|---|---|---|---|---|---|
| Ser | Leu | Pro | Cys<br>20 | Phe | Ala | Val | Lys | Glu<br>25 | Asp | Ser | Leu | Lys | Arg<br>30 | Ile | Thr |
| Gln | Glu | Thr<br>35 | Leu | Leu | Gly | Leu | Leu<br>40 | Asp | Gly | Lys | Phe | Lys<br>45 | Asp | Ile | Phe |
| Asp | Lys<br>50 | Cys | Ile | Ile | Ile<br>55 | Asp | Cys | Arg | Phe | Glu<br>60 | Tyr | Glu | Tyr | Leu | Gly |
| Gly<br>65 | His | Ile | Ser | Thr<br>70 | Ala | Val | Asn | Leu | Asn<br>75 | Thr | Lys | Gln | Ala | Ile<br>80 | Val |
| Asp | Ala | Phe | Leu | Ser<br>85 | Lys | Pro | Leu | Thr | Xaa<br>90 | Xaa | Xaa | Xaa | Xaa | Xaa<br>95 | Xaa |
| Xaa | Xaa | Xaa | Xaa<br>100 | His | Val | Arg | Ala | Xaa<br>105 | Leu | Val | Phe | His | Cys<br>110 | Glu | His |
| Ser | Ala | His<br>115 | Arg | Ala | Pro | His | Leu<br>120 | Ala | Leu | His | Phe | Arg<br>125 | Asn | Thr | Asp |
| Arg | Arg<br>130 | Met | Asn | Ser | His | Arg<br>135 | Tyr | Pro | Phe | Leu | Tyr<br>140 | Tyr | Pro | Glu | Val |
| Tyr<br>145 | Ile | Leu | His | Gly | Gly<br>150 | Tyr | Lys | Ser | Phe | Tyr<br>155 | Glu | Asn | His | Lys | Asn<br>160 |
| Arg | Cys | Asp | Pro | Ile<br>165 | Asn | Tyr | Val | Pro | Met<br>170 | Asn | Asp | Arg | Ser | His<br>175 | Val |
| Asn | Thr | Cys | Thr<br>180 | Lys | Ala | Met | Asn | Asn<br>185 | Phe | Lys | Arg | Xaa | Asn<br>190 | Ala | Thr |
| Phe | Met | Arg<br>195 | Thr | Lys | Ser | Tyr | Thr<br>200 | Phe | Trp | Pro | Lys | Cys<br>205 | Val | Ser | Phe |
| Pro | Arg | Arg<br>210 | | | | | | | | | | | | | |

( 2 ) INFORMATION FOR SEQ ID NO:10:

( i ) SEQUENCE CHARACTERISTICS:
( A ) LENGTH: 75 amino acids
( B ) TYPE: amino acid
( D ) TOPOLOGY: linear ( i i ) MOLECULE TYPE: peptide ( x i ) SEQUENCE DESCRIPTION: SEQ ID NO:10:

| Thr<br>1 | Asp | Gly | Lys | Arg<br>5 | Val | Ile | Val | Val | Phe<br>10 | His | Cys | Glu | Phe | Ser<br>15 | Ser |
|---|---|---|---|---|---|---|---|---|---|---|---|---|---|---|---|
| Glu | Arg | Gly | Pro<br>20 | Arg | Met | Cys | Arg | Tyr<br>25 | Val | Arg | Glu | Arg | Asp<br>30 | Arg | Leu |
| Gly | Asn | Glu<br>35 | Xaa | Xaa | Tyr | Pro | Lys<br>40 | Leu | His | Tyr | Pro | Glu<br>45 | Leu | Tyr | Val |
| Leu | Lys<br>50 | Gly | Gly | Tyr | Lys<br>55 | Glu | Phe | Phe | Met | Lys<br>60 | Cys | Gln | Ser | Tyr | Cys |
| Glu<br>65 | Pro | Pro | Ser | Tyr | Arg<br>70 | Pro | Met | His | His | Glu<br>75 |

( 2 ) INFORMATION FOR SEQ ID NO:11:

( i ) SEQUENCE CHARACTERISTICS:
( A ) LENGTH: 75 amino acids
( B ) TYPE: amino acid
( D ) TOPOLOGY: linear ( i i ) MOLECULE TYPE: peptide ( x i ) SEQUENCE DESCRIPTION: SEQ ID NO:11:

| Ser | Leu | Asp | Lys | Arg | Val | Ile | Leu | Ile | Phe | His | Cys | Glu | Phe | Ser | Ser |
|---|---|---|---|---|---|---|---|---|---|---|---|---|---|---|---|
| 1 | | | | 5 | | | | | 10 | | | | | 15 | |

| Glu | Arg | Gly | Pro | Arg | Met | Cys | Arg | Phe | Ile | Arg | Glu | Arg | Asp | Arg | Ala |
|---|---|---|---|---|---|---|---|---|---|---|---|---|---|---|---|
| | | | 20 | | | | | 25 | | | | | 30 | | |

| Val | Asn | Asp | Xaa | Xaa | Tyr | Pro | Ser | Leu | Tyr | Tyr | Pro | Glu | Met | Tyr | Ile |
|---|---|---|---|---|---|---|---|---|---|---|---|---|---|---|---|
| | | 35 | | | | | 40 | | | | | 45 | | | |

| Leu | Lys | Gly | Gly | Tyr | Lys | Glu | Phe | Phe | Pro | Gln | His | Pro | Asn | Phe | Cys |
|---|---|---|---|---|---|---|---|---|---|---|---|---|---|---|---|
| | 50 | | | | | 55 | | | | | 60 | | | | |

| Glu | Pro | Gln | Asp | Tyr | Arg | Pro | Met | Asn | His | Glu |
|---|---|---|---|---|---|---|---|---|---|---|
| 65 | | | | | 70 | | | | | 75 |

( 2 ) INFORMATION FOR SEQ ID NO:12:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

| Asp | Thr | Gln | Lys | Arg | Ile | Ile | Ile | Val | Phe | His | Cys | Glu | Phe | Ser | Ser |
|---|---|---|---|---|---|---|---|---|---|---|---|---|---|---|---|
| 1 | | | | 5 | | | | | 10 | | | | | 15 | |

| Glu | Arg | Gly | Pro | Arg | Met | Cys | Arg | Cys | Leu | Arg | Glu | Glu | Asp | Arg | Ser |
|---|---|---|---|---|---|---|---|---|---|---|---|---|---|---|---|
| | | | 20 | | | | | 25 | | | | | 30 | | |

| Leu | Asn | Gln | Xaa | Xaa | Tyr | Pro | Ala | Leu | Tyr | Tyr | Pro | Glu | Leu | Tyr | Ile |
|---|---|---|---|---|---|---|---|---|---|---|---|---|---|---|---|
| | | 35 | | | | | 40 | | | | | 45 | | | |

| Leu | Lys | Gly | Gly | Tyr | Arg | Asp | Phe | Phe | Pro | Glu | Tyr | Met | Glu | Leu | Cys |
|---|---|---|---|---|---|---|---|---|---|---|---|---|---|---|---|
| | 50 | | | | | 55 | | | | | 60 | | | | |

| Glu | Pro | Gln | Ser | Tyr | Cys | Pro | Met | His | His | Gln |
|---|---|---|---|---|---|---|---|---|---|---|
| 65 | | | | | 70 | | | | | 75 |

( 2 ) INFORMATION FOR SEQ ID NO:13:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

| Ser | Gly | His | Lys | Arg | Asn | Ile | Ile | Ile | Phe | His | Cys | Glu | Phe | Ser | Ser |
|---|---|---|---|---|---|---|---|---|---|---|---|---|---|---|---|
| 1 | | | | 5 | | | | | 10 | | | | | 15 | |

| Glu | Arg | Gly | Pro | Lys | Met | Ser | Arg | Gly | Leu | Arg | Asn | Leu | Asp | Arg | Glu |
|---|---|---|---|---|---|---|---|---|---|---|---|---|---|---|---|
| | | | 20 | | | | | 25 | | | | | 30 | | |

| Arg | Asn | Thr | Asn | Ala | Tyr | Pro | Ala | Leu | His | Tyr | Pro | Glu | Ile | Tyr | Leu |
|---|---|---|---|---|---|---|---|---|---|---|---|---|---|---|---|
| | | 35 | | | | | 40 | | | | | 45 | | | |

| Leu | His | Asn | Gly | Tyr | Lys | Glu | Phe | Phe | Glu | Ser | His | Val | Glu | Leu | Cys |
|---|---|---|---|---|---|---|---|---|---|---|---|---|---|---|---|
| | 50 | | | | | 55 | | | | | 60 | | | | |

| Glu | Pro | His | Ala | Tyr | Arg | Thr | Met | Leu | Asp | Pro |
|---|---|---|---|---|---|---|---|---|---|---|
| 65 | | | | | 70 | | | | | 75 |

( 2 ) INFORMATION FOR SEQ ID NO:14:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

| Xaa | Xaa | His | Val | Arg | Ala | Xaa | Leu | Val | Phe | His | Cys | Glu | His | Ser | Ala |
|---|---|---|---|---|---|---|---|---|---|---|---|---|---|---|---|
| 1 | | | | 5 | | | | | 10 | | | | | 15 | |

| His | Arg | Ala | Pro | His | Leu | Ala | Leu | His | Phe | Arg | Asn | Thr | Asp | Arg | Arg |
|---|---|---|---|---|---|---|---|---|---|---|---|---|---|---|---|
| | | | 20 | | | | | 25 | | | | | 30 | | |

| Met | Asn | Ser | His | Arg | Tyr | Pro | Phe | Leu | Tyr | Tyr | Pro | Glu | Val | Tyr | Ile |
|---|---|---|---|---|---|---|---|---|---|---|---|---|---|---|---|
| | | 35 | | | | | 40 | | | | | 45 | | | |

| Leu | His | Gly | Gly | Tyr | Lys | Ser | Phe | Tyr | Glu | Asn | His | Lys | Asn | Arg | Cys |
|---|---|---|---|---|---|---|---|---|---|---|---|---|---|---|---|
| | 50 | | | | | 55 | | | | | 60 | | | | |

| Asp | Pro | Ile | Asn | Tyr | Val | Pro | Met | Asn | Asp | Arg |
|---|---|---|---|---|---|---|---|---|---|---|
| 65 | | | | 70 | | | | | 75 | |

( 2 ) INFORMATION FOR SEQ ID NO:15:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

| Xaa | Xaa | Xaa | Xaa | Asn | Glu | Pro | Val | Leu | Val | His | Cys | Ala | Ala | Gly | Val |
|---|---|---|---|---|---|---|---|---|---|---|---|---|---|---|---|
| 1 | | | | 5 | | | | | 10 | | | | | 15 | |

| Asn | Arg | Ser | Gly | Ala | Met | Ile | Leu | Ala | Xaa | Xaa | Xaa | Xaa | Tyr | Leu | Met |
|---|---|---|---|---|---|---|---|---|---|---|---|---|---|---|---|
| | | | 20 | | | | | 25 | | | | | 30 | | |

| Ser | Lys | Asn | Lys | Glu | Ser | Leu | Pro | Met | Leu | Tyr | Phe | Leu | Tyr | Val | Tyr |
|---|---|---|---|---|---|---|---|---|---|---|---|---|---|---|---|
| | | 35 | | | | | 40 | | | | | 45 | | | |

| His | Ser | Met | Arg | Asp | Leu | Arg | Xaa | Gly | Ala | Phe | Val | Glu | Asn | Pro | Ser |
|---|---|---|---|---|---|---|---|---|---|---|---|---|---|---|---|
| | 50 | | | | | 55 | | | | | 60 | | | | |

| Phe | Lys | Arg | Xaa | Xaa | Xaa | Xaa | Gln | Ile | Ile | Glu |
|---|---|---|---|---|---|---|---|---|---|---|
| 65 | | | | 70 | | | | | 75 | |

( 2 ) INFORMATION FOR SEQ ID NO:16:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

| Leu | Ser | Pro | Glu | Asn | Gly | Pro | Ile | Val | Val | His | Cys | Ser | Ala | Gly | Ile |
|---|---|---|---|---|---|---|---|---|---|---|---|---|---|---|---|
| 1 | | | | 5 | | | | | 10 | | | | | 15 | |

| Gly | Arg | Ser | Gly | Thr | Phe | Cys | Leu | Ala | Asp | Thr | Cys | Leu | Leu | Leu | Met |
|---|---|---|---|---|---|---|---|---|---|---|---|---|---|---|---|
| | | | 20 | | | | | 25 | | | | | 30 | | |

| Asp | Lys | Arg | Lys | Asp | Pro | Ser | Ser | Val | Asp | Xaa | Ile | Lys | Lys | Val | Leu |
|---|---|---|---|---|---|---|---|---|---|---|---|---|---|---|---|
| | | 35 | | | | | 40 | | | | | 45 | | | |

| Leu | Glu | Met | Arg | Arg | Phe | Arg | Met | Gly | Xaa | Leu | Ile | Gln | Thr | Ala | Asp |
|---|---|---|---|---|---|---|---|---|---|---|---|---|---|---|---|
| | 50 | | | | | 55 | | | | | 60 | | | | |

| Gln | Leu | Arg | Phe | Ser | Tyr | Leu | Ala | Val | Ile | Glu |
|---|---|---|---|---|---|---|---|---|---|---|
| 65 | | | | 70 | | | | | 75 | |

( 2 ) INFORMATION FOR SEQ ID NO:17:

( i ) SEQUENCE CHARACTERISTICS:
        ( A ) LENGTH: 75 amino acids
        ( B ) TYPE: amino acid
        ( D ) TOPOLOGY: linear (ii) MOLECULE TYPE: peptide (xi) SEQUENCE DESCRIPTION: SEQ ID NO:17:

| Leu | Ser | Pro | Glu | His | Gly | Pro | Val | Val | His | Cys | Ser | Ala | Gly | Ile |
|---|---|---|---|---|---|---|---|---|---|---|---|---|---|---|
| 1 |  |  |  | 5 |  |  |  |  | 10 |  |  |  |  | 15 |
| Gly | Arg | Ser | Gly | Thr | Phe | Cys | Leu | Ala | Asp | Thr | Cys | Leu | Leu | Met |
|  |  |  | 20 |  |  |  |  | 25 |  |  |  |  | 30 |  |
| Asp | Lys | Arg | Lys | Asp | Pro | Ser | Ser | Val | Asp | Xaa | Leu | Lys | Lys | Val | Leu |
|  |  | 35 |  |  |  |  | 40 |  |  |  |  | 45 |  |  |  |
| Leu | Glu | Met | Arg | Lys | Phe | Arg | Met | Gly | Xaa | Leu | Ile | Gln | Thr | Ala | Asp |
|  | 50 |  |  |  |  | 55 |  |  |  |  | 60 |  |  |  |  |
| Gln | Leu | Arg | Phe | Ser | Tyr | Leu | Ala | Val | Ile | Glu |
| 65 |  |  |  |  | 70 |  |  |  |  | 75 |

(2) INFORMATION FOR SEQ ID NO:18:

(i) SEQUENCE CHARACTERISTICS:
(A) LENGTH: 75 amino acids
(B) TYPE: amino acid
(D) TOPOLOGY: linear (ii) MOLECULE TYPE: peptide (xi) SEQUENCE DESCRIPTION: SEQ ID NO:18:

| Leu | Asn | Pro | Asp | His | Gly | Pro | Ala | Val | Ile | His | Cys | Ser | Ala | Gly | Ile |
|---|---|---|---|---|---|---|---|---|---|---|---|---|---|---|---|
| 1 |  |  |  | 5 |  |  |  |  | 10 |  |  |  |  | 15 |  |
| Gly | Arg | Ser | Gly | Thr | Phe | Ser | Leu | Val | Asp | Thr | Cys | Leu | Val | Leu | Met |
|  |  |  | 20 |  |  |  |  | 25 |  |  |  |  | 30 |  |  |
| Glu | Lys | Gly | Asp | Asp | Ile | Asn | Xaa | Xaa | Xaa | Xaa | Ile | Lys | Gln | Val | Leu |
|  |  | 35 |  |  |  |  | 40 |  |  |  |  | 45 |  |  |  |
| Leu | Asn | Met | Arg | Lys | Tyr | Arg | Met | Gly | Xaa | Leu | Ile | Gln | Thr | Pro | Asp |
|  | 50 |  |  |  |  | 55 |  |  |  |  | 60 |  |  |  |  |
| Gln | Leu | Arg | Phe | Ser | Tyr | Met | Ala | Ile | Ile | Glu |
| 65 |  |  |  |  | 70 |  |  |  |  | 75 |

(2) INFORMATION FOR SEQ ID NO:19:

(i) SEQUENCE CHARACTERISTICS:
(A) LENGTH: 75 amino acids
(B) TYPE: amino acid
(D) TOPOLOGY: linear (ii) MOLECULE TYPE: peptide (xi) SEQUENCE DESCRIPTION: SEQ ID NO:19:

| Leu | Ala | Val | Asn | Asp | Val | Asp | Ala | Glu | Asp | Gly | Ala | Asp | Pro | Asn | Leu |
|---|---|---|---|---|---|---|---|---|---|---|---|---|---|---|---|
| 1 |  |  |  | 5 |  |  |  |  | 10 |  |  |  |  | 15 |  |
| Cys | Ser | Glu | Tyr | Val | Lys | Asp | Ile | Tyr | Ala | Tyr | Leu | Arg | Gln | Leu | Glu |
|  |  |  | 20 |  |  |  |  | 25 |  |  |  |  | 30 |  |  |
| Glu | Glu | Gln | Ala | Val | Arg | Pro | Lys | Tyr | Leu | Leu | Gly | Arg | Glu | Val | Thr |
|  |  | 35 |  |  |  |  | 40 |  |  |  |  | 45 |  |  |  |
| Gly | Asn | Met | Arg | Ala | Ile | Leu | Ile | Asp | Trp | Leu | Val | Gln | Xaa | Xaa | Val |
|  | 50 |  |  |  |  | 55 |  |  |  |  | 60 |  |  |  |  |
| Gln | Met | Lys | Phe | Arg | Leu | Leu | Gln | Xaa | Xaa | Glu |
| 65 |  |  |  |  | 70 |  |  |  |  | 75 |

(2) INFORMATION FOR SEQ ID NO:20:

(i) SEQUENCE CHARACTERISTICS:
(A) LENGTH: 75 amino acids
(B) TYPE: amino acid
(D) TOPOLOGY: linear (ii) MOLECULE TYPE: peptide ( x i ) SEQUENCE DESCRIPTION: SEQ ID NO:20:

| Ile | His | Val | Lys | Asp | Val | Asp | Ala | Asp | Asp | Gly | Asn | Pro | Met | Leu |
|---|---|---|---|---|---|---|---|---|---|---|---|---|---|---|
| 1 | | | | 5 | | | | | 10 | | | | | 15 |

| Cys | Ser | Glu | Tyr | Val | Lys | Asp | Ile | Tyr | Ala | Tyr | Leu | Arg | Ser | Leu | Glu |
|---|---|---|---|---|---|---|---|---|---|---|---|---|---|---|---|
| | | | 20 | | | | | 25 | | | | | 30 | | |

Asp Ala Gln Ala Val Arg Gln Asn Tyr Leu His Gly Gln Glu Val Thr
              35                    40                 45

Gly Asn Met Arg Ala Ile Leu Ile Asp Trp Leu Val Gln Xaa Xaa Val
      50                  55                  60

Gln Met Arg Phe Arg Leu Leu Gln Xaa Xaa Glu
65              70                75

( 2 ) INFORMATION FOR SEQ ID NO:21:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Thr Ser Val Glu Asp Ile Asp Ala Asp Asp Gly Gly Asn Pro Gln Leu
1               5                   10                  15

Cys Ser Asp Tyr Val Met Asp Ile Tyr Asn Tyr Leu Lys Gln Leu Glu
              20                  25                  30

Val Gln Gln Ser Val His Pro Cys Tyr Leu Glu Gly Lys Glu Ile Asn
          35              40              45

Glu Arg Met Arg Ala Ile Leu Val Asp Trp Leu Val Gln Xaa Xaa Val
        50              55                  60

His Ser Arg Phe Gln Leu Leu Gln Xaa Xaa Glu
65              70              75

( 2 ) INFORMATION FOR SEQ ID NO:22:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Leu Cys Cys Glu Val Glu Thr Ile Arg Arg Ala Tyr Pro Asp Ala Asn
1               5                   10                  15

Leu Leu Asn Asp Arg Val Leu Arg Ala Met Leu Lys Ala Glu Glu Thr
              20                  25                  30

Cys Ala Pro Ser Val Ser Tyr Phe Lys Cys Val Gln Lys Glu Val Leu
          35              40              45

Pro Ser Met Arg Lys Ile Val Ala Thr Trp Met Leu Glu Xaa Xaa Val
      50              55                  60

Cys Glu Glu Gln Lys Cys Glu Glu Xaa Xaa Glu
65              70              75

( 2 ) INFORMATION FOR SEQ ID NO:23:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

| Met | Ser | Ile | Val | Leu | Glu | Asp | Glu | Lys | Pro | Val | Ser | Val | Asn | Glu | Val |
|---|---|---|---|---|---|---|---|---|---|---|---|---|---|---|---|
| 1 | | | | 5 | | | | | 10 | | | | | 15 | |

| Pro | Asp | Tyr | His | Glu | Asp | Ile | His | Thr | Tyr | Leu | Arg | Glu | Met | Glu | Val |
|---|---|---|---|---|---|---|---|---|---|---|---|---|---|---|---|
| | | | 20 | | | | 25 | | | | | 30 | | | |

| Lys | Cys | Lys | Pro | Lys | Val | Gly | Tyr | Met | Lys | Lys | Gln | Pro | Asp | Ile | Thr |
|---|---|---|---|---|---|---|---|---|---|---|---|---|---|---|---|
| | | 35 | | | | | 40 | | | | 45 | | | | |

| Asn | Ser | Met | Arg | Ala | Ile | Leu | Val | Asp | Trp | Leu | Val | Glu | Xaa | Xaa | Val |
|---|---|---|---|---|---|---|---|---|---|---|---|---|---|---|---|
| | 50 | | | | | 55 | | | | | 60 | | | | |

| Gly | Glu | Glu | Tyr | Lys | Leu | Gln | Asn | Xaa | Xaa | Glu |
|---|---|---|---|---|---|---|---|---|---|---|
| 65 | | | | | 70 | | | | | 75 |

( 2 ) INFORMATION FOR SEQ ID NO:24:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

| Ile | Ile | Asp | Cys | Arg | Thr | Phe | Pro | Glu | Tyr | Glu |
|---|---|---|---|---|---|---|---|---|---|---|
| 1 | | | | 5 | | | | | 10 | |

( 2 ) INFORMATION FOR SEQ ID NO:25:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

| Ala | Thr | Ile | Ala | Thr | Ile | Gly | Ala | Thr | Thr | Gly | Cys | Cys | Gly | Ile | Thr |
|---|---|---|---|---|---|---|---|---|---|---|---|---|---|---|---|
| 1 | | | | 5 | | | | | 10 | | | | | 15 | |

| Ala | Thr | Cys | Cys | Cys | Ile | Thr | Ala | Cys | Thr | Gly | Ala |
|---|---|---|---|---|---|---|---|---|---|---|---|
| | | | 20 | | | | | 25 | | | |

( 2 ) INFORMATION FOR SEQ ID NO:26:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

| Ala | Thr | Ile | Ala | Thr | Ile | Gly | Ala | Thr | Thr | Gly | Cys | Cys | Gly | Ile | Thr |
|---|---|---|---|---|---|---|---|---|---|---|---|---|---|---|---|
| 1 | | | | 5 | | | | | 10 | | | | | 15 | |

| Ala | Thr | Cys | Gly | Ala | Ile | Thr | Ala | Cys | Thr | Gly | Ala |
|---|---|---|---|---|---|---|---|---|---|---|---|
| | | | 20 | | | | | 25 | | | |

( 2 ) INFORMATION FOR SEQ ID NO:27:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

ATAGAACTTC AGCAAGTGAG AAAGTA                                      26

( 2 ) INFORMATION FOR SEQ ID NO:28:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:28:

Cys Gln Gly Ala Leu Asn Leu Tyr Ser Gln Glu Glu Leu Phe
1               5                   10

( 2 ) INFORMATION FOR SEQ ID NO:29:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:29:

Cys Lys Gly Ala Val Asn Leu His Met Glu Glu Glu Val Glu
1               5                   10

( 2 ) INFORMATION FOR SEQ ID NO:30:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:30:

Cys Lys Lys Lys Val Glu Lys Ile Gly Glu Gly Thr Tyr Gly Val Val
1               5                   10                  15

Tyr Lys ( 2 ) INFORMATION FOR SEQ ID NO:31:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:31:

Leu Val Phe His Cys Glu Xaa Xaa Xaa Xaa Arg
1               5                   10

1. Purified CDC25A protein which is of human origin.

2. Purified CDC25 B protein which is of human origin.

3. An antibody which specifically binds human CDC25 A protein.

4. An antibody which specifically binds human CDC25 B protein.

5. An antibody which specifically binds the CDC25A protein represented in SEQ ID NO: 2.

6. An antibody which specifically binds the CDC25B protein represented in SEQ ID NO: 4.

7. Recombinant CDC25 phosphatase comprising the amino acid sequence represented by SEQ ID NO: 2.

8. The recombinant phosphatase of claim 7, which recombinant phosphatase is a fusion protein.

9. The recombinant phosphatase of claim 8, wherein the fusion protein further includes a glutathione-S-transferase amino acid sequence.

10. The recomdinant phosphatase of claim 7, which recombinant phosphatase hydrolyzes p-nitrophenylphosphate.

11. Recombinant CDC25 phosphatase comprising the amino acid sequence represented by SEQ ID NO: 4.

12. The recombinant phosphatase of claim 11, which recombinant phosphatase is a fusion protein.

13. The recombinant phosphatase of claim 12, wherein the fusion protein further includes a glutathione-S-transferase amino acid sequence.

14. The recombinant phosphatase of claim 11, which recombinant phosphatase hydrolyzes p-nitrophenyl-phosphate.

15. The recombinant phosphatase of claim 7, which recombinant phosphatase rescues a mutant cdc25-22 strain of fission yeast.

16. The recombinant phosphatase of claim 11, which recombinant phosphatase rescues a mutant cdc25-22 strain of fission yeast.

17. The recombinant phosphatase of claim 7, which recombinant phosphatase possesses an endogenous tyrosine phosphatase activity.

18. The recombinant phosphatase of claim 17, which endogenous tyrosine phosphatase activity dephosphorylates a phosphorylated catalytic subunit of an M-phase kinase.

19. The recombinant phosphatase of claim 17, which endogenous tyrosine phosphatase activity dephosphorylates a phosphorylated CDC2 kinase.

20. The recombinant phosphatase of claim 11, which recombinant phosphatase possesses an endogenous tyrosine phosphatase activity.

21. The recombinant phosphatase of claim 20, which endogenous tyrosine phosphatase activity dephosphorylates a phosphorylated catalytic subunit of an M-phase kinase.

22. The recombinant phosphatase of claim 20, which endogenous tyrosine phosphatase activity dephosphorylates a phosphorylated CDC2 kinase.

* * * * *